(12) United States Patent
Handique

(10) Patent No.: US 8,709,787 B2
(45) Date of Patent: Apr. 29, 2014

(54) MICROFLUIDIC CARTRIDGE AND METHOD OF USING SAME

(75) Inventor: Kalyan Handique, Ypsilanti, MI (US)

(73) Assignee: Handylab, Inc., Franklin Lakes, NJ (US)

( * ) Notice: Subject to any disclaimer, the term of this patent is extended or adjusted under 35 U.S.C. 154(b) by 0 days.

(21) Appl. No.: 11/940,310

(22) Filed: Nov. 14, 2007

(65) Prior Publication Data
US 2009/0047713 A1 Feb. 19, 2009

Related U.S. Application Data

(60) Provisional application No. 60/859,284, filed on Nov. 14, 2006, provisional application No. 60/959,437, filed on Jul. 13, 2007.

(51) Int. Cl.
*C12Q 1/68* (2006.01)
*C12P 19/34* (2006.01)
*B01L 99/00* (2010.01)

(52) U.S. Cl.
USPC ............... 435/283.1; 435/91.2; 435/288.2; 435/288.5; 422/501; 422/537

(58) Field of Classification Search
USPC .......................... 435/283.1, 6, 6.12
See application file for complete search history.

(56) References Cited

U.S. PATENT DOCUMENTS

| | | |
|---|---|---|
| 1,434,314 A | 10/1922 | Raich |
| 1,616,419 A | 2/1927 | Wilson |
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |

(Continued)

FOREIGN PATENT DOCUMENTS

| | | |
|---|---|---|
| CA | 2294819 | 1/1999 |
| DE | 19929734 | 12/1999 |

(Continued)

OTHER PUBLICATIONS

International Search Report and Written Opinion dated Sep. 11, 2008 for PCT/US2007/084730.

(Continued)

*Primary Examiner* — Betty Forman
(74) *Attorney, Agent, or Firm* — Knobbe Martens Olson & Bear LLP

(57) ABSTRACT

The present technology provides for a microfluidic substrate configured to carry out PCR on a number of polynucleotide-containing samples in parallel. The substrate can be a single-layer substrate in a microfluidic cartridge. Also provided are a method of making a microfluidic cartridge comprising such a substrate. Still further disclosed are a microfluidic valve suitable for use in isolating a PCR chamber in a microfluidic substrate, and a method of making such a valve.

22 Claims, 47 Drawing Sheets

(56) References Cited

U.S. PATENT DOCUMENTS

| | | |
|---|---|---|
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |

(56) References Cited

U.S. PATENT DOCUMENTS

| | | |
|---|---|---|
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | Macleod et al. |

(56) References Cited

U.S. PATENT DOCUMENTS

| | | |
|---|---|---|
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Lines et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Torelli et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | Mcreynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | Mcreynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |

(56) References Cited

U.S. PATENT DOCUMENTS

| | | |
|---|---|---|
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeiser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Shinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | Mcreynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| 7,727,371 B2 | 6/2010 | Kennedy et al. |
| 7,727,477 B2 | 6/2010 | Boronkay et al. |
| 7,744,817 B2 * | 6/2010 | Bui .............................. 422/68.1 |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 | 8/2011 | Handique et al. |
| 8,088,616 B2 | 1/2012 | Handique |
| 8,105,783 B2 * | 1/2012 | Handique .................... 435/6.12 |
| 8,133,671 B2 | 3/2012 | Williams et al. |
| 8,182,763 B2 | 5/2012 | Duffy et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0015667 A1 | 2/2002 | Chow |
| 2002/0021983 A1 | 2/2002 | Comte et al. |
| 2002/0037499 A1 | 3/2002 | Quake et al. |

(56) References Cited

U.S. PATENT DOCUMENTS

| | | |
|---|---|---|
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1* | 6/2002 | Mathies et al. ............ 435/287.2 |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Tetsumasa Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0799081 | 10/2003 | Wilding et at |
| 2003/0211517 A1 | 11/2003 | Carulli et al. |
| 2004/0014238 A1 | 1/2004 | Krug et al. |
| 2004/0018119 A1 | 1/2004 | Massaro |
| 2004/0029258 A1* | 2/2004 | Heaney et al. ............ 435/287.2 |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur, Jr. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0235154 A1* | 11/2004 | Oh et al. ............ 435/303.1 |
| 2004/0240097 A1 | 12/2004 | Evans |
| 2005/0009174 A1 | 1/2005 | Nikiforov et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1* | 3/2006 | Kim ............................. 435/6 |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0207944 A1 | 9/2006 | Siddiqi |
| 2006/0210435 A1 | 9/2006 | Alavie et al. |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1* | 3/2008 | McNeely ........................ 422/63 |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0189089 A1 | 7/2009 | Bedingham et al. |
| 2010/0173393 A1 | 7/2010 | Handique et al. |
| 2011/0008825 A1 | 1/2011 | Ingber et al. |
| 2011/0027151 A1 | 2/2011 | Handique et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0160826 A1 | 6/2012 | Handique |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0217013 A1 | 8/2013 | Steel et al. |

(56) References Cited

U.S. PATENT DOCUMENTS

| | | |
|---|---|---|
| 2013/0217102 A1 | 8/2013 | Ganesan et al. |
| 2013/0251602 A1 | 9/2013 | Handique et al. |
| 2013/0280131 A1 | 10/2013 | Handique et al. |

FOREIGN PATENT DOCUMENTS

| | | |
|---|---|---|
| EP | 0766256 | 4/1997 |
| EP | 1541237 A2 | 6/2005 |
| EP | 2372367 A1 | 10/2011 |
| FR | 2672301 | 8/1992 |
| FR | 2795426 | 12/2000 |
| JP | 58212921 A | 12/1983 |
| JP | H07-290706 | 11/1995 |
| JP | 2001-509437 | 7/2001 |
| JP | 2001-515216 | 9/2001 |
| JP | A-2001-527220 | 12/2001 |
| JP | 2002-503331 | 1/2002 |
| JP | 2002-215241 | 7/2002 |
| JP | A-2003-500674 | 1/2003 |
| JP | 2005-514718 | 5/2005 |
| JP | 2005-518825 | 6/2005 |
| JP | A-2005-204661 | 8/2005 |
| JP | 2005-291954 A | 10/2005 |
| JP | 2005-532043 | 10/2005 |
| WO | WO 88/06633 | 9/1988 |
| WO | WO 90/12350 | 10/1990 |
| WO | WO 92/05443 | 4/1992 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/49548 | 11/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 2004/007081 | 1/2004 |
| WO | WO 2004/055522 | 7/2004 |
| WO | WO 2004/074848 | 9/2004 |
| WO | WO 2005/011867 | 2/2005 |
| WO | WO 2005011867 A2 * | 2/2005 |
| WO | WO 2005/108620 | 11/2005 |
| WO | WO 2006/079082 | 7/2006 |
| WO | WO 2006/119280 | 11/2006 |
| WO | WO 2007/044917 | 4/2007 |
| WO | WO 2007/050327 | 5/2007 |
| WO | WO 2008/030914 | 3/2008 |
| WO | WO 2008/060604 | 5/2008 |
| WO | WO 2009/012185 | 1/2009 |
| WO | WO 2010/118541 | 10/2010 |

OTHER PUBLICATIONS

Mascini et al., "DNA electrochemical biosensors", Fresenius J. Anal. Chem., 369: 15-22, (2001).
Nakagawa et al., Fabrication of amino silane-coated microchip for DNA extraction from whole blood, J of Biotechnology, Mar. 2, 2005, vol. 116, pp. 105-111.
Plambeck et al., "Electrochemical Studies of Antitumor Antibiotics", J. Electrochem Soc.: Electrochemical Science and Technology (1984), 131(11): 2556-2563.
Wang, "Survey and Summary, from DNA Biosensors to Gene Chips", Nucleic Acids Research, 28(16):3011-3016, (2000).
Bollet, C. et al., "A simple method for the isolation of chromosomal DNA from Gram positive or acid-fast bacteria", Nucleic Acids Research, vol. 19, No. 8 (1991), p. 1955.
Brahmassandra, et al., On-Chip DNA Detection in Microfabricated Separation Systems, Part of the SPIE Conference on Microfludic Devices and Systems, 1998, Santa Clara, California, vol. 3515, pp. 242-251.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles, et al., "Sample Filtration, Concentration, and Separation Integrated on Microfluidic Devices" Analytical Chemistry (American Chemical Society), vol. 75 No. 11: pp. 2761-2767.
Burns et al., "An Integrated Nanoliter DNA Analysis Device", Science 282:484-487 (1998).
Carlen et al., "Paraffin Actuated Surface Micromachined Valve," in IEEE MEMS 2000 Conference, p. 381-385, Miyazaki, Japan, Jan. 2000.
Chung, Y. et al., "Microfluidic chip for high efficiency DNA extraction", Miniaturisation for Chemistry, Biology & Bioengineering, vol. 4, No. 2 (Apr. 2004), pp. 141-147.
Handique K., et al., On-Chip Thermopneumatic Pressure for Discrete Drop Pumping, Analytical Chemistry, American Chemical Society, Apr. 15, 2001, vol. 73, No. 8, 1831-1838.
Handique, K. et al, "Microflidic flow control using selective hydrophobic patterning", SPIE, vol. 3224, pp. 185-194 (1997).
Handique, K. et al., "Nanoliter-vol. discrete drop injection and pumping in microfabricated chemical analysis systems", Solid-State Sensor and Actuator Workshop (Hilton Head, South Carolina, Jun. 8-11, 1998) pp. 346-349.
Handique, K. et al., "Mathematical Modeling of Drop Mixing in a Slit-Type Micochannel", J. Micromech. Microeng., 11:548-554 (2001).
Handique, K. et al., "Nanoliter Liquid Metering in Microchannels Using Hydrophobic Patterns", Anal. Chem., 72:4100-4109 (2000).
He, et al., Microfabricated Filters for Microfludic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, vol. 70, No. 9, pp. 2013-2017.
Khandurina, et al., Microfabricated Porous Membrane Structure for Sample Concentraction and Electrophoretic Analysis, Analytical Chemistry American Chemical Society, 1999, vol. 71, No. 9, pp. 1815-1819.
Kopp, et al., Chemical Amplification: Continuous-Flow PCR on a Chip, www.sciencemag.org, 1998, vol. 280, pp. 1046-1048.
Kutter, et al., Solid Phase Extraction on Microfludic Devices, J. Microcolumn Separations, John Wiley & Sons, Inc., 2000, vol. 12, No. 2, pp. 93-97.
Lagally, et al., Single-Molecule DNA Amplification and Analysis in an Integrated Microfluidic Device, Analytical Chemistry, American Chemical Society, 2001, vol. 73, No. 3 pp. 565-570.
Livache, T. et al., "Polypyrrole DNA chip on a Silicon Device: Example of Hepatitis C Virus Genotyping", Analytical Biochemistry, vol. 255 (1998), pp. 188-194.
Northrup, et al., A Miniature Analytical Instrument for Nucleic Acids Based on Micromachined Silicon Reaction Chambers, Analytical Chemistry, American Chemical Society, 1998, vol. 70, No. 5, pp. 918-922.
Oleschuk, et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.
Orchid BioSciences, Inc., www.orchid.com, Jul. 6, 2001.

(56) References Cited

OTHER PUBLICATIONS

Roche, et al. "Ectodermal commitment of insulin-producing cells derived from mouse embryonic stem cells" Faseb J (2005) 19: 1341-1343.

Ross, et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner, M. A. et al., Chip PCR.I. Surface Passivation of Microfabricated Silicon-Glass Chips for PCR, Nucleic Acids Research, Oxford University Press, 1996, vol. 24, No. 2, 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Waters, et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl, et al., Microfluidic Diffusion-Based Separation and Detection, www.sciencemag.org, 1999, vol. 283, pp. 346-347.

Yoza, Brandon et al., DNA extraction using bacterial magnetic particles modified with hyperbranched polyamidoamine dendrimer, Mar. 20, 2003, vol. 101, No. 3, 219-228.

Yoza, et al., "Fully Automated DNA Extraction fro Blood Using Magnetic Particles Modified with a Hyperbranched Polyamidomine Dendrimer", Journal of Bioscience and Bioengineering, 95(1):21-26, 2003.

* cited by examiner

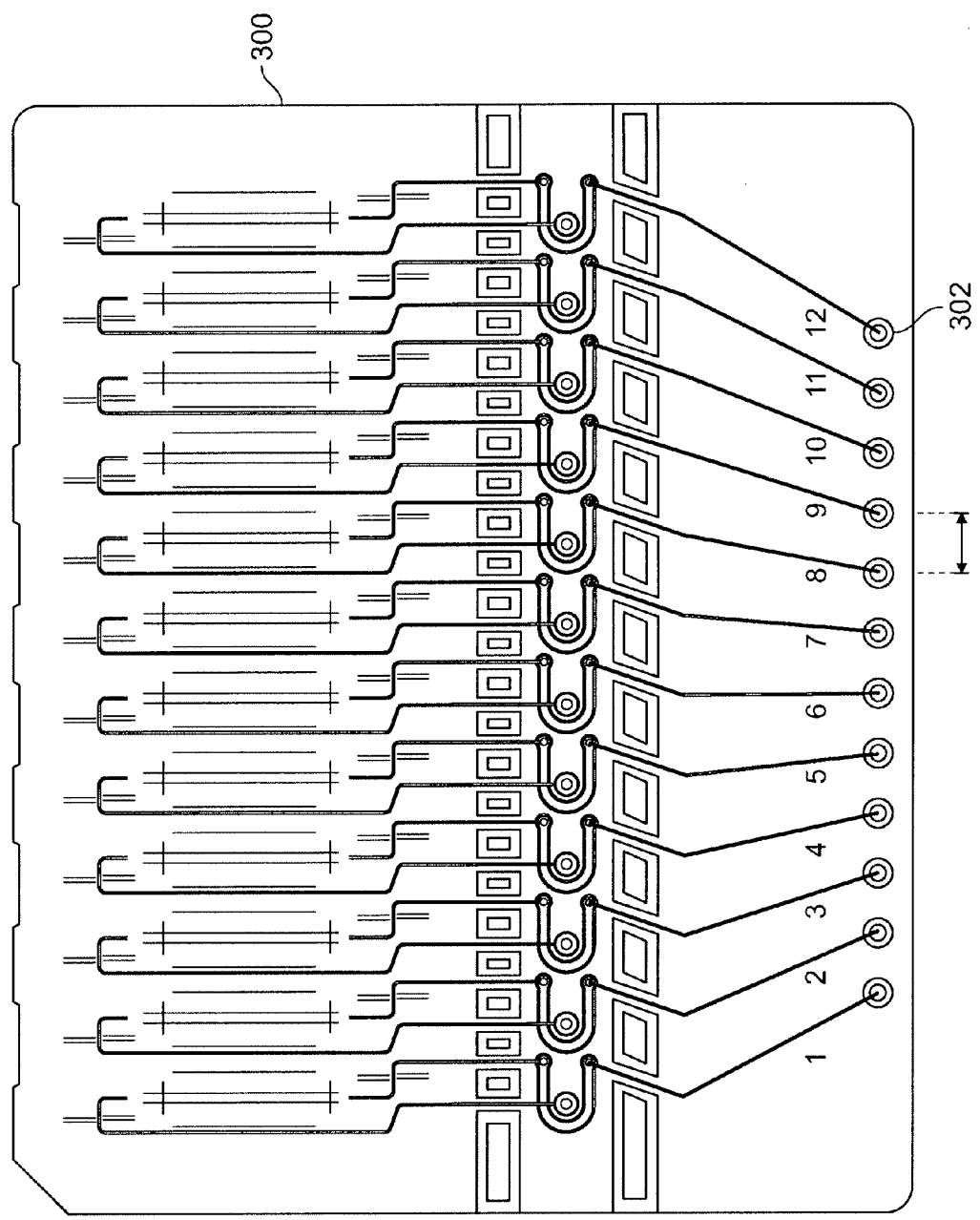

Capillary action of controlled volume of wax causes it to fill up the Wax up to the right interface without blocking the liquid flowable microchannel

MICROFLUIDIC CARTRIDGE AND METHOD OF USING SAME

CLAIM OF PRIORITY

The instant application claims the benefit of priority to U.S. provisional applications having Ser. Nos. 60/859,284, filed Nov. 14, 2006, and 60/959,437, filed Jul. 13, 2007, the specifications of both of which are incorporated herein by reference in their entireties.

TECHNICAL FIELD

The technology described herein generally relates to microfluidic cartridges. The technology more particularly relates to microfluidic cartridges that are configured to carry out PCR on nucleotides of interest, particularly from several biological samples in parallel, within microfluidic channels in the cartridge, and permit detection of those nucleotides.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mix-up. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using polymerase chain reaction (PCR) to amplify a vector of interest. Once amplified, the presence or absence of a nucleotide of interest from the sample needs to be determined unambiguously. Sample preparation is a process that is susceptible to automation but is also relatively routinely carried out in almost any location. By contrast, steps such as PCR and nucleotide detection have customarily only been within the compass of specially trained individuals having access to specialist equipment.

There is therefore a need for a method and apparatus of carrying out PCR on prepared biological samples and detecting amplified nucleotides, preferably with high throughput. In particular there is a need for an easy-to-use device that can deliver a diagnostic result on several samples in a short time.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present technology includes methods and devices for detecting polynucleotides in samples, particularly from biological samples. In particular, the technology relates to microfluidic devices that carry out PCR on nucleotides of interest within microfluidic channels, and permit detection of those nucleotides.

In particular, the present technology provides for a microfluidic cartridge, comprising: a first PCR reaction chamber; a second PCR reaction chamber; a first inlet, in fluid communication with the first PCR reaction chamber; a second inlet, in fluid communication with the second PCR reaction chamber; a first set of microfluidic valves configured to control motion of a sample from the first inlet to the first PCR reaction chamber; and a second set of microfluidic valves configured to control motion of a sample from the second inlet to the second PCR reaction chamber.

The present technology includes a process for carrying out PCR on a plurality of polynucleotide-containing samples, the method comprising: introducing the plurality of samples into a microfluidic cartridge, wherein the cartridge has a plurality of PCR reaction chambers configured to permit thermal cycling of the plurality of samples independently of one another; moving the plurality of samples into the respective plurality of PCR reaction chambers; and amplifying polynucleotides contained with the plurality of samples, by application of successive heating and cooling cycles to the PCR reaction chambers.

The present technology further comprises a number of other embodiments, as set forth herein.

A microfluidic substrate, comprising: a first PCR reaction chamber; a second PCR reaction chamber; a first inlet, in fluid communication with the first PCR reaction chamber; a second inlet, in fluid communication with the second PCR reaction chamber; a first set of microfluidic valves configured to isolate the first reaction chamber from the first inlet; and a second set of microfluidic valves configured to isolate the second PCR reaction chamber from the second inlet.

A microfluidic substrate, comprising: a plurality of sample lanes, wherein each of the plurality of sample lanes comprises a microfluidic network having, in fluid communication with one another: an inlet; a first valve and a second valve; a first channel leading from the inlet, via the first valve, to a reaction chamber; and a second channel leading from the reaction chamber, via the second valve, to a vent.

A microfluidic cartridge having a plurality of microfluidic networks, wherein each of the microfluidic networks, including a PCR reaction chamber, an inlet hole, and the valves for isolating the PCR reaction chamber, is defined in a single substrate.

A method of carrying out PCR independently on a plurality of polynucleotide-containing samples, the method comprising: introducing the plurality of samples in to a microfluidic cartridge, wherein the cartridge has a plurality of PCR reaction chambers configured to permit thermal cycling of the plurality of samples independently of one another; moving the plurality of samples into the respective plurality of PCR reaction chambers; isolating the plurality of PCR reaction chambers; and amplifying polynucleotides contained with the plurality of samples, by application of successive heating and cooling cycles to the PCR reaction chambers.

A microfluidic valve, comprising: a first chamber, connected to a first load channel; a second chamber, connected to a second load channel; and a flow channel, wherein the first and second load channels are each connected to the flow channel, and wherein the first and second load channels each contain a thermally responsive substance that, upon actuation of the valve, flows into the flow channel thereby sealing it, and wherein the flow channel is constricted along a length either side of the first and second load channels.

A microfluidic valve, comprising: a chamber, connected to a load channel; and a flow channel, wherein the load channel is connected to the flow channel, and wherein the load channel contains a thermally responsive substance that, upon actuation of the valve, flows into the flow channel thereby sealing it, and wherein the flow channel is constricted along a length either side of the load channel.

A method of making a microfluidic valve, the method comprising: directing a dispensing head over an inlet hole in a microfluidic substrate; propelling a quantity of thermally responsive substance from the dispensing head into the inlet hole; and maintaining a temperature of the microfluidic substrate so that the thermally responsive substance flows by capillary action from the inlet hole into a microfluidic channel in communication with the inlet hole.

The microfluidic cartridge described herein can be configured for use with an apparatus comprising: a chamber configured to receive the microfluidic cartridge; at least one heat source thermally coupled to the cartridge and configured to apply heat and cooling cycles that carry out PCR on one or more microdroplets of polynucleotide-containing sample in the cartridge; a detector configured to detect presence of one or more polynucleotides in the one or more samples; and a processor coupled to the detector and the heat source, configured to control heating of one or more regions of the microfluidic cartridge.

The details of one or more embodiments of the technology are set forth in the accompanying drawings and further description herein. Other features, objects, and advantages of the technology will be apparent from the description and drawings, and from the claims.

BRIEF DESCRIPTION OF THE DRAWINGS

FIG. 3 shows a plan of microfluidic circuitry and inlets in an exemplary multi-lane cartridge;

DETAILED DESCRIPTION

Microfluidic Cartridge

Figure 1:
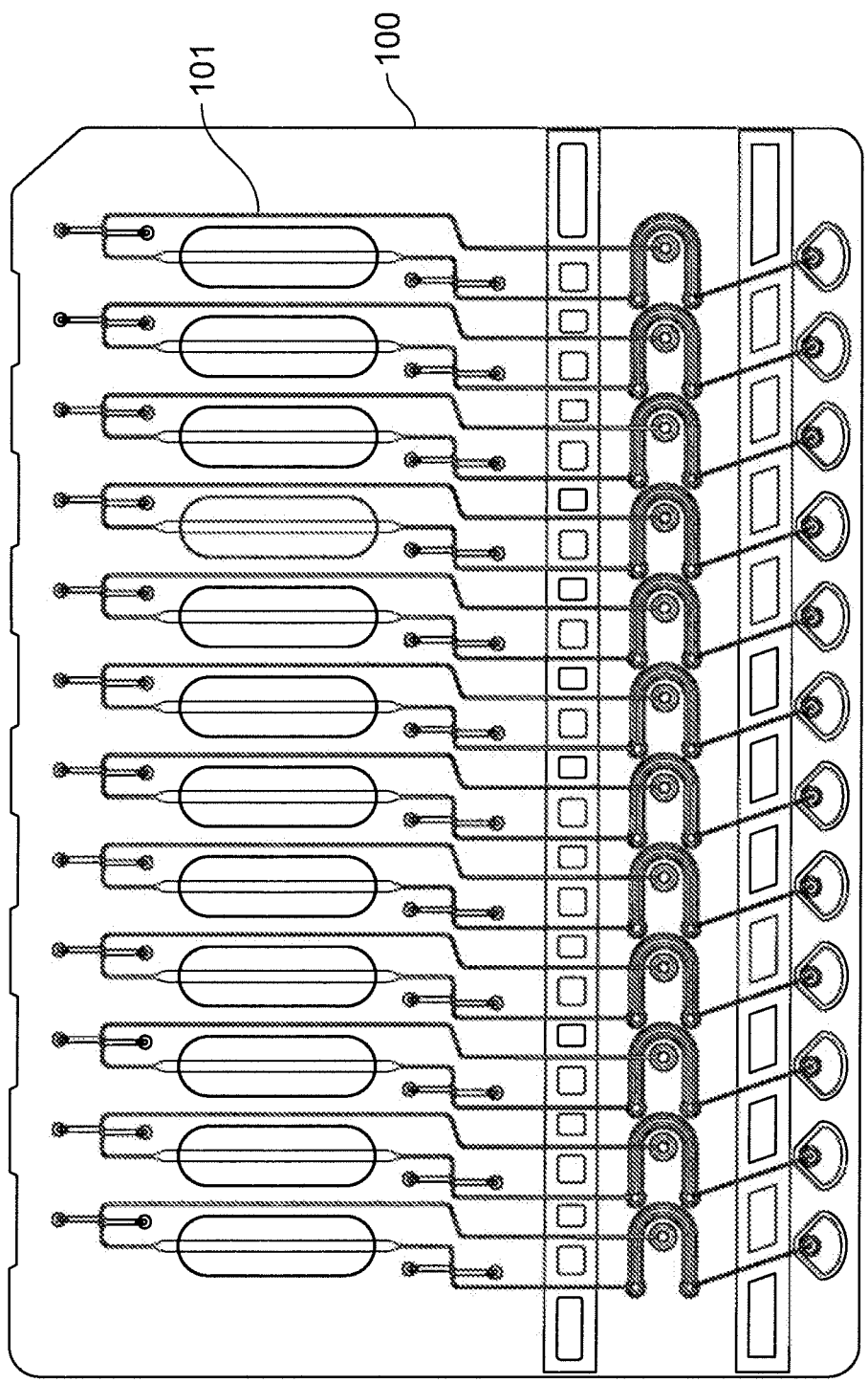
FIG. 1 shows a plan view of an exemplary multi-lane microfluidic cartridge.

The present technology comprises a microfluidic cartridge that is configured to carry out an amplification, such as by PCR, of one or more polynucleotides from one or more samples. It is to be understood that, unless specifically made clear to the contrary, where the term PCR is used herein, any variant of PCR including but not limited to real-time and quantitative, and any other form of polynucleotide amplification is intended to be encompassed. The microfluidic cartridge need not be self-contained and can be designed so that it receives thermal energy from one or more heating elements present in an external apparatus with which the cartridge is in thermal communication. An exemplary such apparatus is further described herein; additional embodiments of such a system are found in U.S. patent application Ser. No. 11/985,577, entitled "Microfluidic System for Amplifying and Detecting Polynucleotides in Parallel", and filed on even date herewith, the specification of which is incorporated herein by reference.

By cartridge is meant a unit that may be disposable, or reusable in whole or in part, and that is configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 µl to about 999 µl, such as from 1-100 µl, or from 2-25 µl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide. Certain embodiments herein can also function with nanoliter volumes (in the range of 10-500 nanoliters, such as 100 nanoliters).

One aspect of the present technology relates to a microfluidic cartridge having two or more sample lanes arranged so that analyses can be carried out in two or more of the lanes in parallel, for example simultaneously, and wherein each lane is independently associated with a given sample.

A sample lane is an independently controllable set of elements by which a sample can be analyzed, according to methods described herein as well as others known in the art. A sample lane comprises at least a sample inlet, and a microfluidic network having one or more microfluidic components, as further described herein.

In various embodiments, a sample lane can include a sample inlet port or valve, and a microfluidic network that comprises, in fluidic communication one or more components selected from the group consisting of: at least one thermally actuated valve, a bubble removal vent, at least one thermally actuated pump, a gate, mixing channel, positioning element, microreactor, a downstream thermally actuated valve, and a PCR reaction chamber. The sample inlet valve can be configured to accept a sample at a pressure differential compared to ambient pressure of between about 70 and 100 kilopascals.

The cartridge can therefore include a plurality of microfluidic networks, each network having various components, and each network configured to carry out PCR on a sample in which the presence or absence of one or more polynucleotides is to be determined.

A multi-lane cartridge is configured to accept a number of samples in series or in parallel, simultaneously or consecutively, in particular embodiments 12 samples, wherein the samples include at least a first sample and a second sample, wherein the first sample and the second sample each contain one or more polynucleotides in a form suitable for amplification. The polynucleotides in question may be the same as, or different from one another, in different samples and hence in different lanes of the cartridge. The cartridge typically processes each sample by increasing the concentration of a polynucleotide to be determined and/or by reducing the concentration of inhibitors relative to the concentration of polynucleotide to be determined.

The multi-lane cartridge comprises at least a first sample lane having a first microfluidic network and a second lane having a second microfluidic network, wherein each of the first microfluidic network and the second microfluidic network is as elsewhere described herein, and wherein the first microfluidic network is configured to amplify polynucleotides in the first sample, and wherein the second microfluidic network is configured to amplify polynucleotides in the second sample.

In various embodiments, the microfluidic network can be configured to couple heat from an external heat source to a sample mixture comprising PCR reagent and neutralized polynucleotide sample under thermal cycling conditions suitable for creating PCR amplicons from the neutralized polynucleotide sample.

At least the external heat source may operate under control of a computer processor, configured to execute computer readable instructions for operating one or more components of each sample lane, independently of one another, and for receiving signals from a detector that measures fluorescence from one or more of the PCR reaction chambers.

For example, FIG. 1 shows a plan view of a microfluidic cartridge 100 containing twelve independent sample lanes 101 capable of simultaneous or successive processing. The microfluidic network in each lane is typically configured to carry out amplification, such as by PCR, on a PCR-ready sample, such as one containing nucleic acid extracted from a sample using other methods as further described herein. A PCR-ready sample is thus typically a mixture comprising the PCR reagents and the neutralized polynucleotide sample, suitable for subjecting to thermal cycling conditions that create PCR amplicons from the neutralized polynucleotide sample. For example, a PCR-ready sample can include a PCR reagent mixture comprising a polymerase enzyme, a positive control plasmid, a fluorogenic hybridization probe selective for at least a portion of the plasmid and a plurality of nucleotides, and at least one probe that is selective for a polynucleotide sequence. Exemplary probes are further described herein. Typically, the microfluidic network is configured to couple heat from an external heat source with the mixture comprising the PCR reagent and the neutralized polynucleotide sample under thermal cycling conditions suitable for creating PCR amplicons from the neutralized polynucleotide sample.

In various embodiments, the PCR reagent mixture can include a positive control plasmid and a plasmid fluorogenic hybridization probe selective for at least a portion of the plasmid, and the microfluidic cartridge can be configured to allow independent optical detection of the fluorogenic hybridization probe and the plasmid fluorogenic hybridization probe.

In various embodiments, the microfluidic cartridge can accommodate a negative control polynucleotide, wherein the microfluidic network can be configured to independently carry out PCR on each of a neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide. Each lane of a multi-lane cartridge as described herein can perform two reactions when used in conjunction with two fluorescence detection systems per lane. A variety of combinations of reactions can be performed in the cartridge, such as two sample reactions in one lane, a positive control and a negative control in two other lanes; or a sample reaction and an internal control in one lane and a negative control in a separate lane.

Figure 2A:
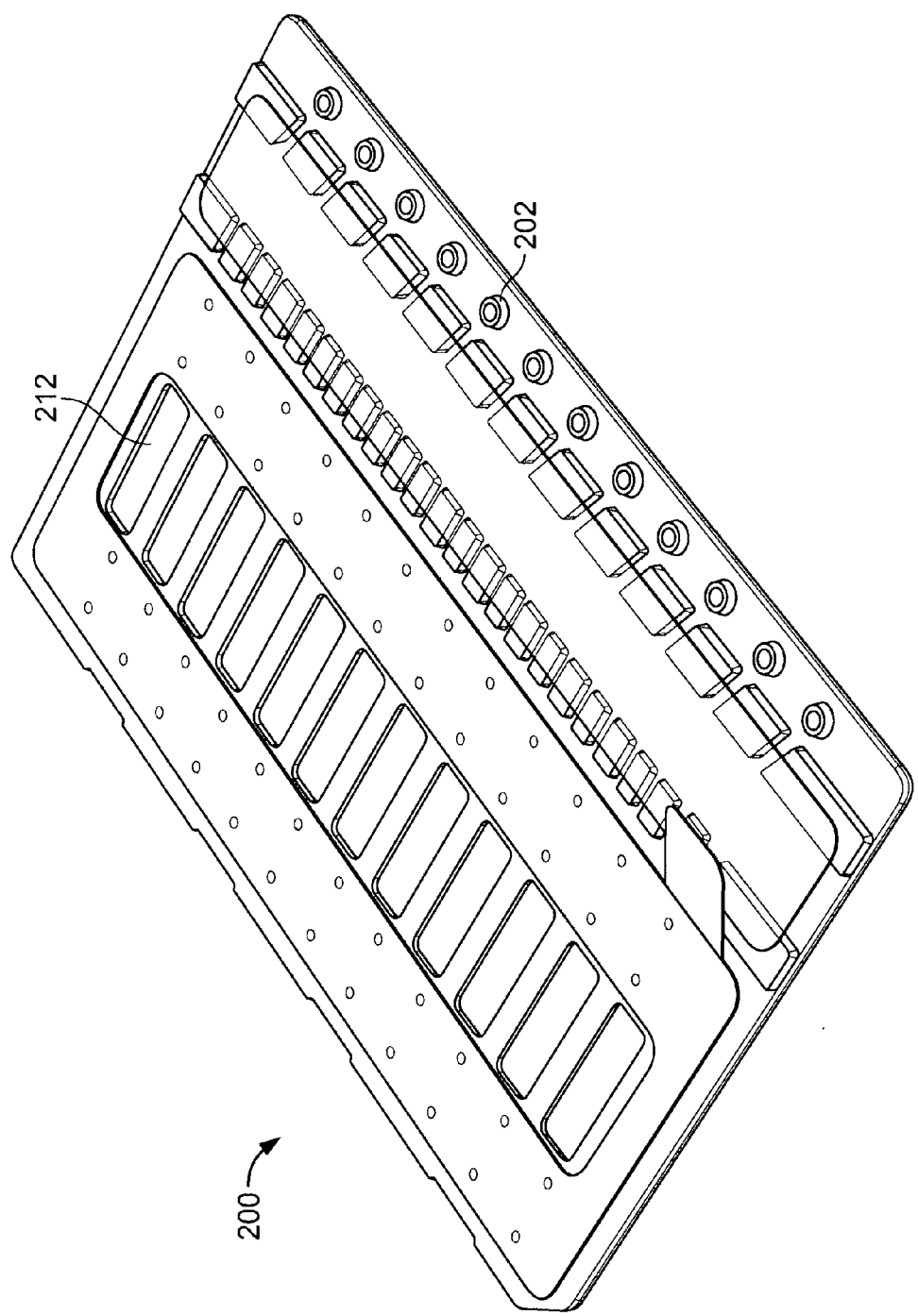
FIG. 2A shows an exemplary multi-lane cartridge.
Figure 2B:
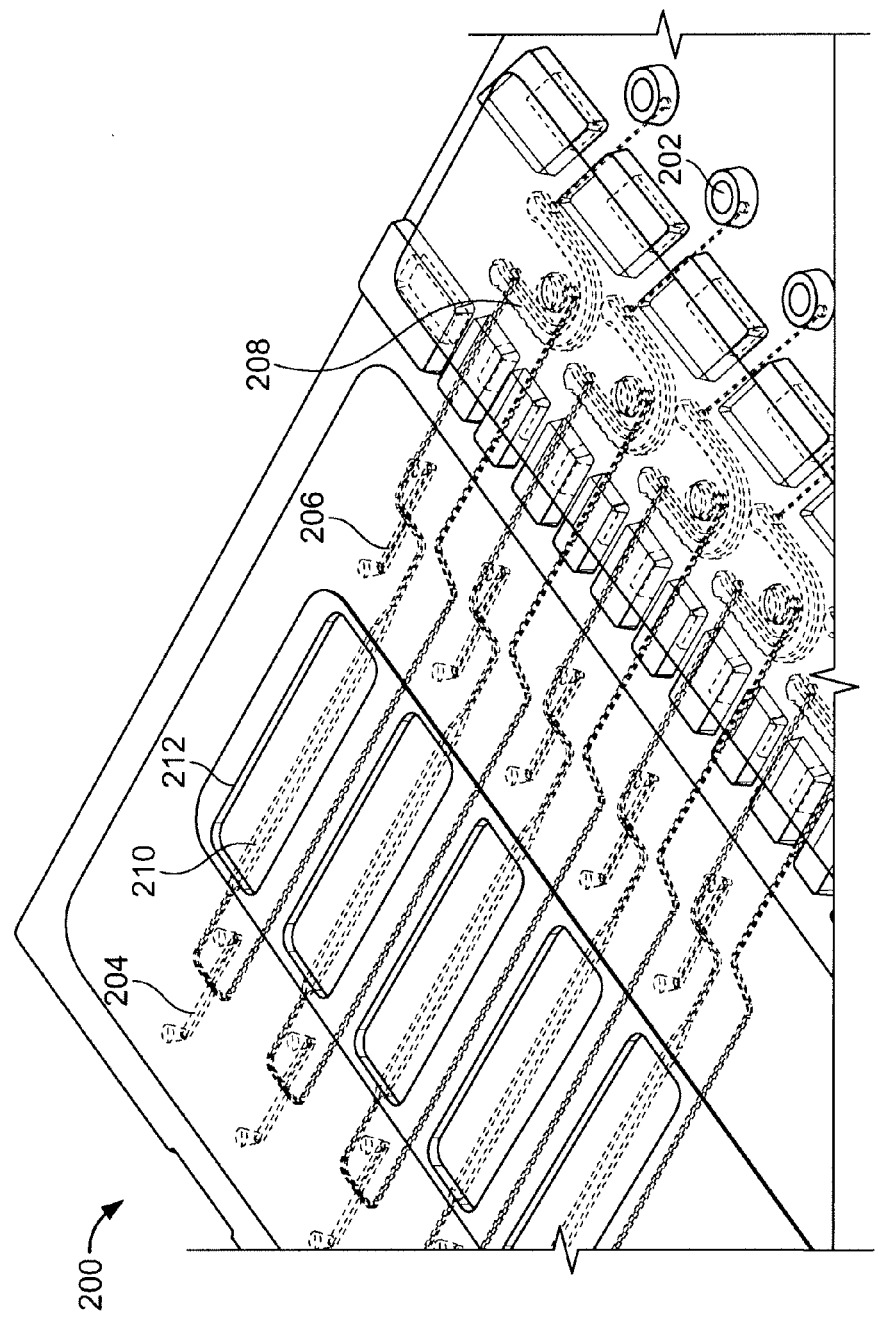
FIG. 2B shows a portion of an exemplary multi-lane cartridge of FIG. 2A.

FIG. 2A shows a perspective view of a portion of an exemplary microfluidic cartridge 200 according to the present technology. FIG. 2B shows a close-up view of a portion of the cartridge 200 of FIG. 2A illustrating various representative components. The cartridge 200 may be referred to as a multi-lane PCR cartridge with dedicated sample inlets 202. For example sample inlet 202 is configured to accept a liquid transfer member (not shown) such as a syringe, a pipette, or a PCR tube containing a PCR ready sample. More than one inlet 202 is shown in FIGS. 2A, 2B, wherein one inlet operates in conjunction with a single sample lane. Various components of microfluidic circuitry in each lane are also visible. For example, microvalves 204, and 206, and hydrophobic vents 208 for removing air bubbles, are parts of microfluidic circuitry in a given lane. Also shown is an ultrafast PCR reactor 210, which, as further described herein, is a microfluidic channel in a given sample lane that is long enough to permit PCR to amplify polynucleotides present in a sample. Above each PCR reactor 210 is a window 212 that permits detection of fluorescence from a fluorescent substance in PCR reactor 210 when a detector is situated above window 212. It is to be understood that other configurations of windows are possible including, but not limited to, a single window that straddles each PCR reactor across the width of cartridge 200.

In preferred embodiments, the multi-sample cartridge has a size substantially the same as that of a 96-well plate as is customarily used in the art. Advantageously, then, such a cartridge may be used with plate handlers used elsewhere in the art.

The sample inlets of adjacent lanes are reasonably spaced apart from one another to prevent any contamination of one sample inlet from another sample when a user introduces a sample into any one cartridge. In an embodiment, the sample inlets are configured so as to prevent subsequent inadvertent introduction of sample into a given lane after a sample has already been introduced into that lane. In certain embodiments, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes can be manufactured conical in shape with an appropriate conical angle so that industry-standard pipette tips (2 µl, 20 µl, 200 µl, volumes, etc.) fit snugly therein. The cartridge herein may be adapted to suit other, later-arising, industry standards not otherwise described herein, as would be understood by one of ordinary skill in the art.

FIG. 3 shows a plan view of an exemplary microfluidic cartridge 300 having 12 sample lanes. The inlet ports 302 in this embodiment have a 6 mm spacing, so that, when used in conjunction with an automated sample loader having 4 heads, spaced equidistantly at 18 mm apart, the inlets can be loaded in three batches of four inlets: e.g., inlets 1, 4, 7, and 10 together, followed by 2, 5, 8, and 11, then finally 3, 6, 9, and 12, wherein the 12 inlets are numbered consecutively from one side of the cartridge to the other as shown.

A microfluidic cartridge as used herein may be constructed from a number of layers. Accordingly, one aspect of the present technology relates to a microfluidic cartridge that comprises a first, second, third, fourth, and fifth layers wherein one or more layers define a plurality of microfluidic networks, each network having various components configured to carry out PCR on a sample in which the presence or absence of one or more polynucleotides is to be determined. In various embodiments, one or more such layers are optional.

Figure 4A:
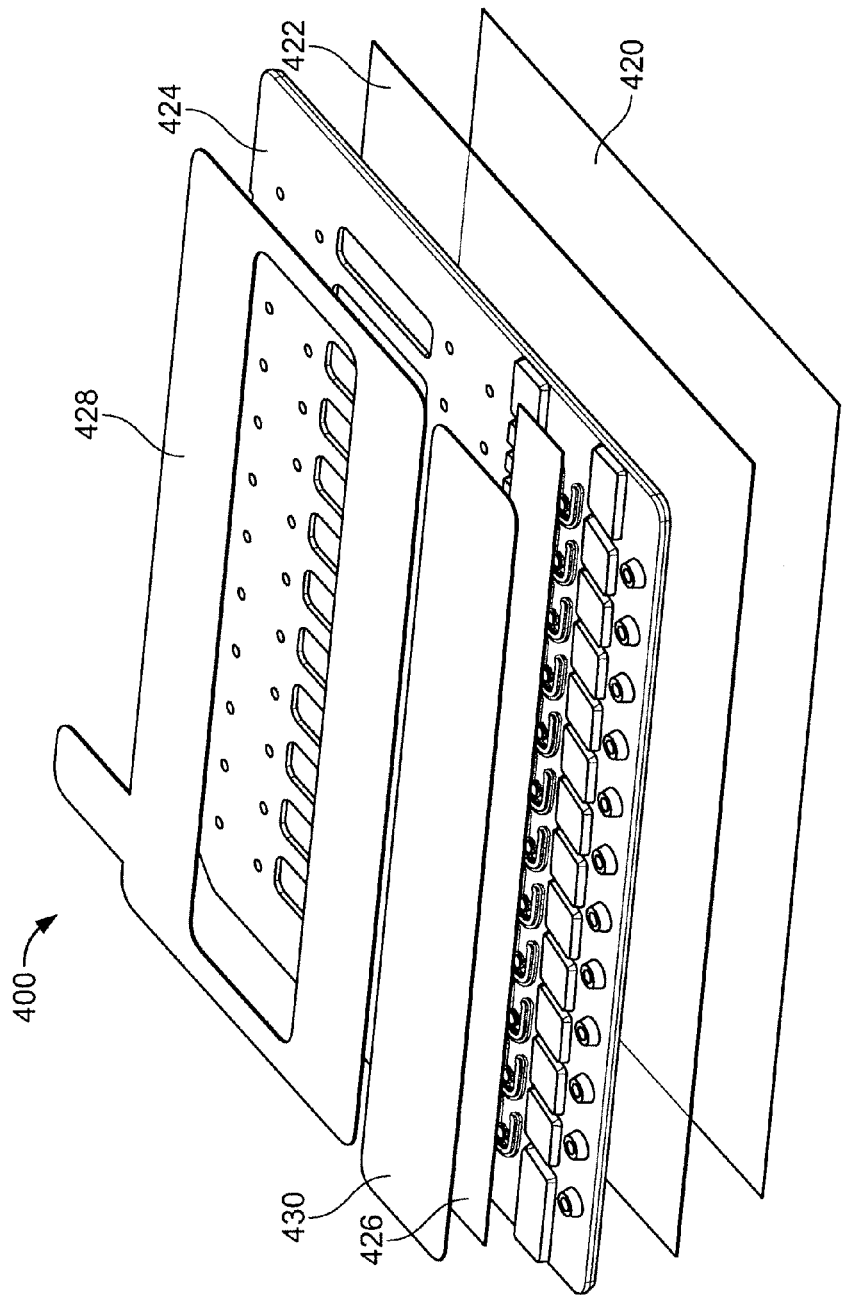
FIGS. 4A-4C show layer construction, and cross section of an exemplary microfluidic cartridge.
Figure 4B:
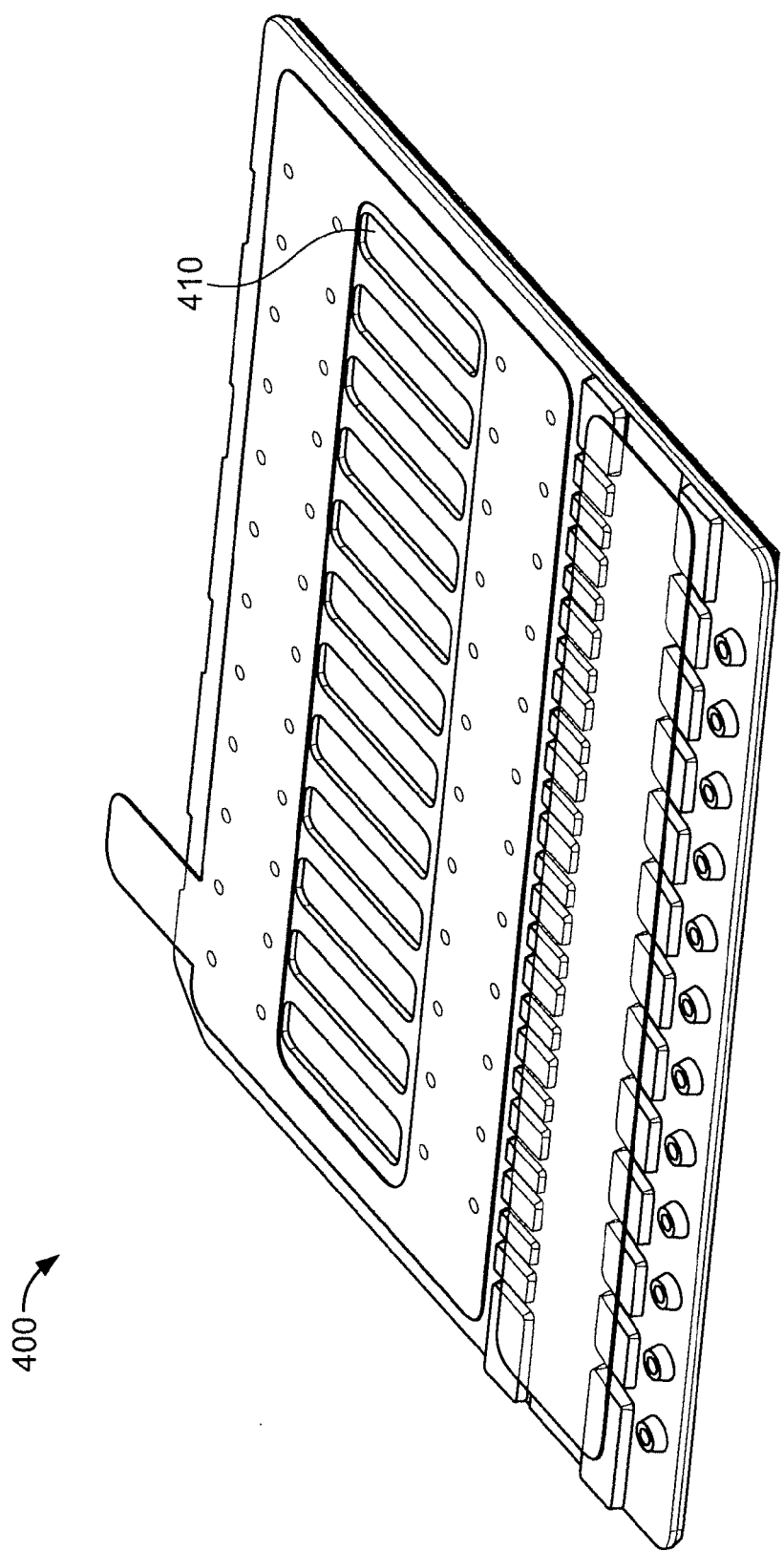
Figure 4C:
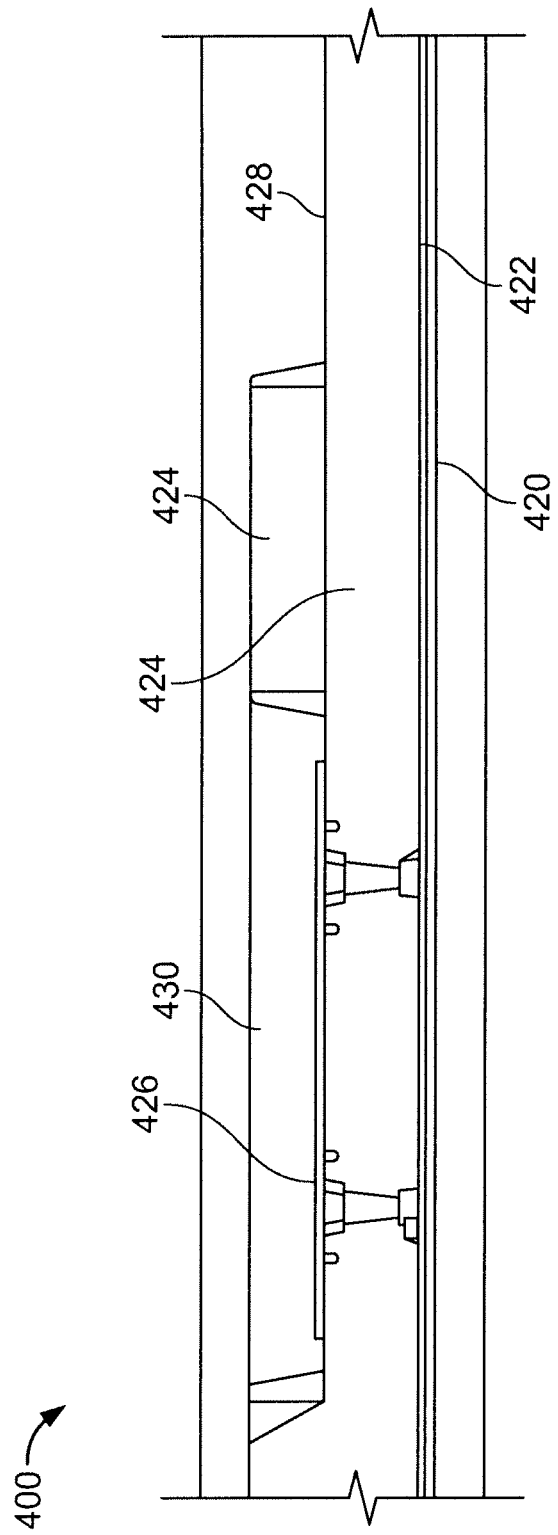

FIGS. 4A-C show various views of a layer structure of an exemplary microfluidic cartridge comprising a number of layers, as further described herein. FIG. 4A shows an exploded view; FIG. 4B shows a perspective view; and FIG. 4C shows a cross-sectional view of a sample lane in the exemplary cartridge. Referring to FIGS. 4A-C, an exemplary microfluidic cartridge 400 includes first 420, second 422, third 424, fourth 426, and fifth layers in two non-contiguous parts 428, 430 (as shown) that enclose a microfluidic network having various components configured to process multiple samples in parallel that include one or more polynucleotides to be determined.

Microfluidic cartridge 400 can be fabricated as desired. The cartridge can include a microfluidic substrate layer 424, typically injection molded out of a plastic, such as a zeonor plastic (cyclic olefin polymer), having a PCR channel and valve channels on a first side and vent channels and various inlet holes, including wax loading holes and liquid inlet holes, on a second side (disposed toward hydrophobic vent membrane 426). It is advantageous that all the microfluidic network defining structures, such as PCR reactors, valves, inlet holes, and air vents, are defined on the same single substrate 424. This attribute facilitates manufacture and assembly of the cartridge. Additionally, the material from which this substrate is formed is rigid or non-deformable, non-venting to air and other gases, and has a low autofluorescence to facilitate detection of polynucleotides during an amplification reaction performed in the microfluidic circuitry defined therein. Rigidity is advantageous because it facilitates effective and uniform contact with a heat unit as further described herein. Use of a non-venting material is also advantageous because it reduces the likelihood that the concentration of various species in liquid form will change during analysis. Use of a material having low auto-fluorescence is also important so that background fluorescence does not detract from measurement of fluorescence from the analyte of interest.

The cartridge can further include, disposed on top of the substrate 424, an oleophobic/hydrophobic vent membrane layer 426 of a porous material, such as 0.2 to 1.0 micron pore-size membrane of modified polytetrafluorethylene, the membrane being typically between about 25 and about 100 microns thick, and configured to cover the vent channels of microfluidic substrate 424, and attached thereto using, for example, heat bonding.

Typically, the microfluidic cartridge further includes a layer 428, 430 of polypropylene or other plastic label with pressure sensitive adhesive (typically between about 50 and 150 microns thick) configured to seal the wax loading holes of the valves in substrate 424, trap air used for valve actuation, and serve as a location for operator markings. In FIG. 4A, this layer is shown in two separate pieces, 428, 430, though it would be understood by one of ordinary skill in the art that a single piece layer would be appropriate.

In various embodiments, the label is a computer-readable label. For example, the label can include a bar code, a radio frequency tag or one or more computer-readable characters. The label can be formed of a mechanically compliant material. For example, the mechanically compliant material of the label can have a thickness of between about 0.05 and about 2 millimeters and a Shore hardness of between about 25 and about 100. The label can be positioned such that it can be read by a sample identification verifier as further described herein.

The cartridge can further include a heat sealable laminate layer 422 (typically between about 100 and about 125 microns thick) attached to the bottom surface of the microfluidic substrate 424 using, for example, heat bonding. This layer serves to seal the PCR channels and vent channels in substrate 424. The cartridge can further include a thermal interface material layer 420 (typically about 125 microns thick), attached to the bottom of the heat sealable laminate layer using, for example, pressure sensitive adhesive. The layer 420 can be compressible and have a higher thermal conductivity than common plastics, thereby serving to transfer heat across the laminate more efficiently. Typically, however, layer 420 is not present.

The application of pressure to contact the cartridge to the heater of an instrument that receives the cartridge generally assists in achieving better thermal contact between the heater and the heat-receivable parts of the cartridge, and also prevents the bottom laminate structure from expanding, as would happen if the PCR channel was only partially filled with liquid and the air entrapped therein would be thermally expanded during thermocycling.

In use, cartridge 400 is typically thermally associated with an array of heat sources configured to operate the components (e.g., valves, gates, actuators, and processing region 410) of the device. Exemplary such heater arrays are further described herein. Additional embodiments of heater arrays are described in U.S. patent application Ser. No. 11/940,315, entitled "Heater Unit for Microfluidic Diagnostic System" and filed on even date herewith, the specification of which is incorporated herein by reference in its entirety. In some embodiments, the heat sources are controlled by a computer processor and actuated according to a desired protocol. Processors configured to operate microfluidic devices are described in, e.g., U.S. application Ser. No. 09/819,105, filed Mar. 28, 2001, which application is incorporated herein by reference.

In various embodiments, during transport and storage, the microfluidic cartridge can be further surrounded by a sealed pouch. The microfluidic cartridge can be sealed in the pouch with an inert gas. The microfluidic cartridge can be disposable for example after one or more of its sample lanes have been used.

Highly Multiplexed Embodiments

Embodiments of the cartridge described herein may be constructed that have high-density microfluidic circuitry on a single cartridge that thereby permit processing of multiple samples in parallel, or in sequence, on a single cartridge. Preferred numbers of such multiple samples include 20, 24, 36, 40, 48, 50, 60, 64, 72, 80, 84, 96, and 100, but it would be understood that still other numbers are consistent with the apparatus and cartridge herein, where deemed convenient and practical.

Accordingly, different configurations of lanes, sample inlets, and associated heater networks than those explicitly depicted in the FIGs and examples that can facilitate processing such numbers of samples on a single cartridge are within the scope of the instant disclosure. Similarly, alternative configurations of detectors and heating elements for use in conjunction with such a highly multiplexed cartridge are also within the scope of the description herein.

It is also to be understood that the microfluidic cartridges described herein are not to be limited to rectangular shapes, but can include cartridges having circular, elliptical, triangular, rhombohedral, square, and other shapes. Such shapes may also be adapted to include some irregularity, such as a cut-out, to facilitate placement in a complementary apparatus as further described herein.

Figure 5:
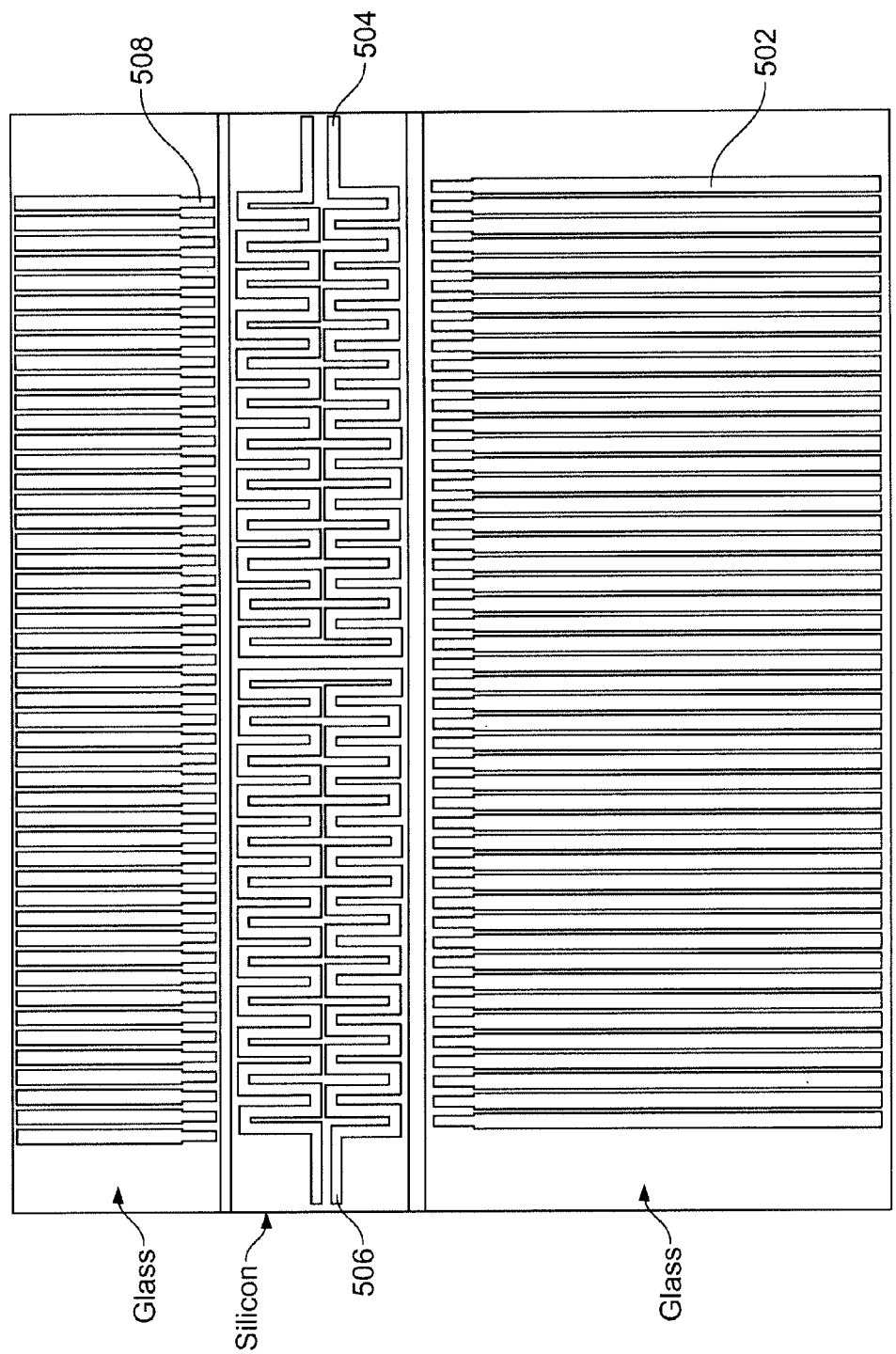
FIG. 5 shows a heater array for an exemplary highly-multiplexed microfluidic cartridge.

In an exemplary embodiment, a highly multiplexed cartridge has 48 sample lanes, and permits independent control of each valve in each lane by suitably configured heater circuitry, with 2 banks of thermocycling protocols per lane, as shown in FIG. 5. In the embodiment in FIG. 5, the heaters (shown superimposed on the lanes) are arranged in three arrays 502, 504, with 506, and 508. The heaters are themselves disposed within one or more substrates. Heater arrays 502, 508 in two separate glass regions only apply heat to valves in the microfluidic networks in each lane. Because of the low thermal conductivity of glass, the individual valves may be heated separately from one another. This permits samples to be loaded into the cartridge at different times, and passed to the PCR reaction chambers independently of one another. The PCR heaters 504, 506 are mounted on a silicon substrate—and are not readily heated individually, but thereby permit batch processing of PCR samples, where multiple samples from different lanes are amplified by the same set of heating/cooling cycles. It is preferable for the PCR heaters to be arranged in 2 banks (the heater arrays 506 on the left and right 508 are not in electrical communication with one another), thereby permitting a separate degree of sample control.

Figure 6:
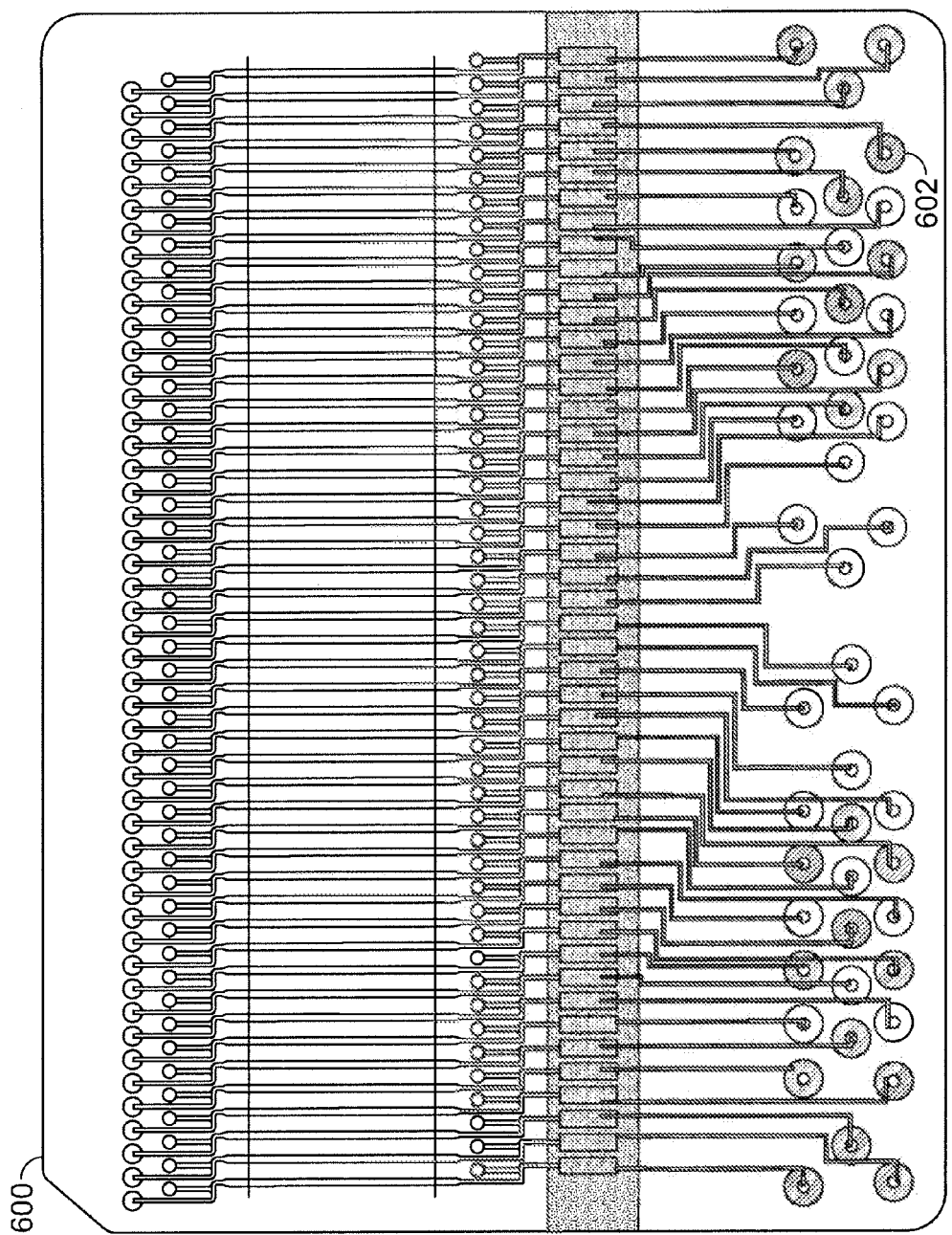
FIGS. 6-9 show various aspects of exemplary highly multiplexed microfluidic cartridges.

FIG. 6 shows a representative 48-sample cartridge 600 compatible with the heater arrays of FIG. 5, and having a configuration of inlets 602 different to that depicted o other cartridges herein. The inlet configuration is exemplary and has been designed to maximize efficiency of space usage on the cartridge. The inlet configuration can be compatible with an automatic pipetting machine that has dispensing heads situated at a 9 mm spacing. For example, such a machine having 4 heads can load 4 inlets at once, in 12 discrete steps, for the cartridge of FIG. 6. Other configurations of inlets though not explicitly described or depicted are compatible with the technology described herein.

Figure 7:
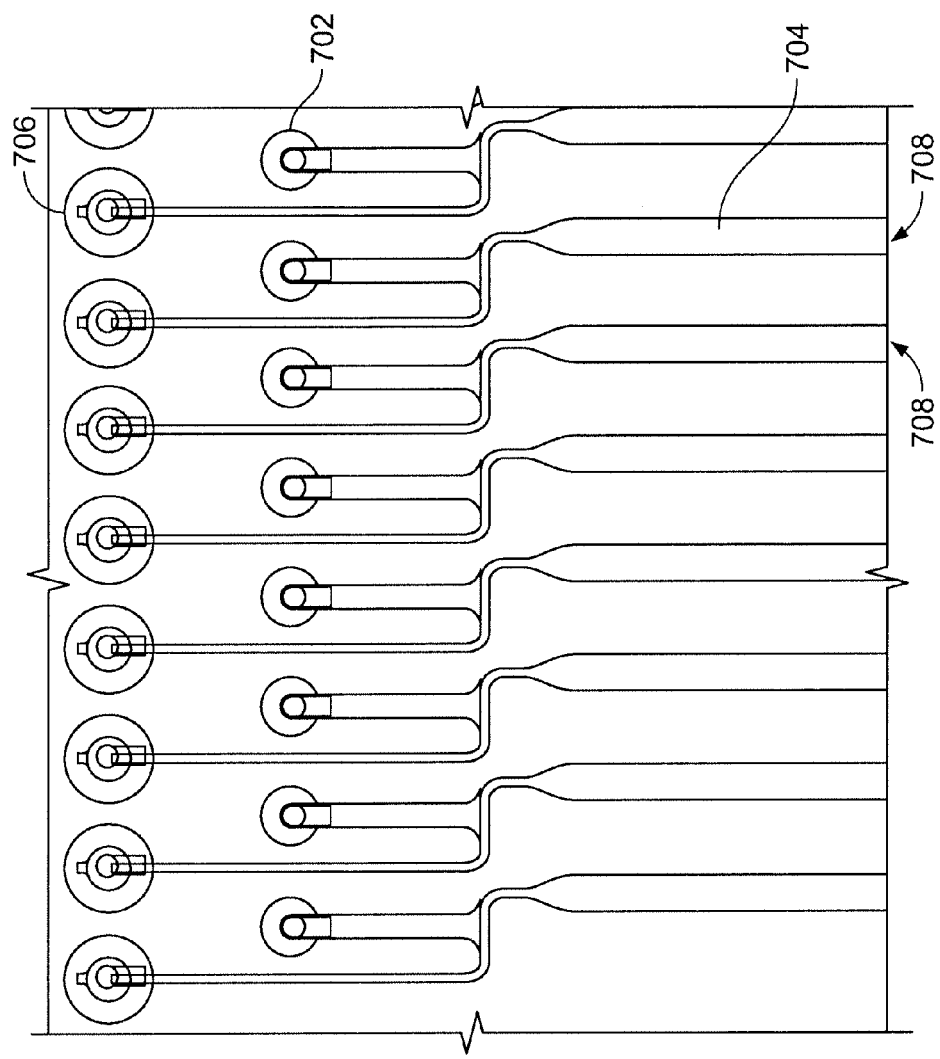

FIG. 7 shows, in close up, an exemplary spacing of valves 702, channels 704, and vents 706, in adjacent lanes 708 of a multi-sample microfluidic cartridge for example as shown in FIG. 6.

Figure 8:
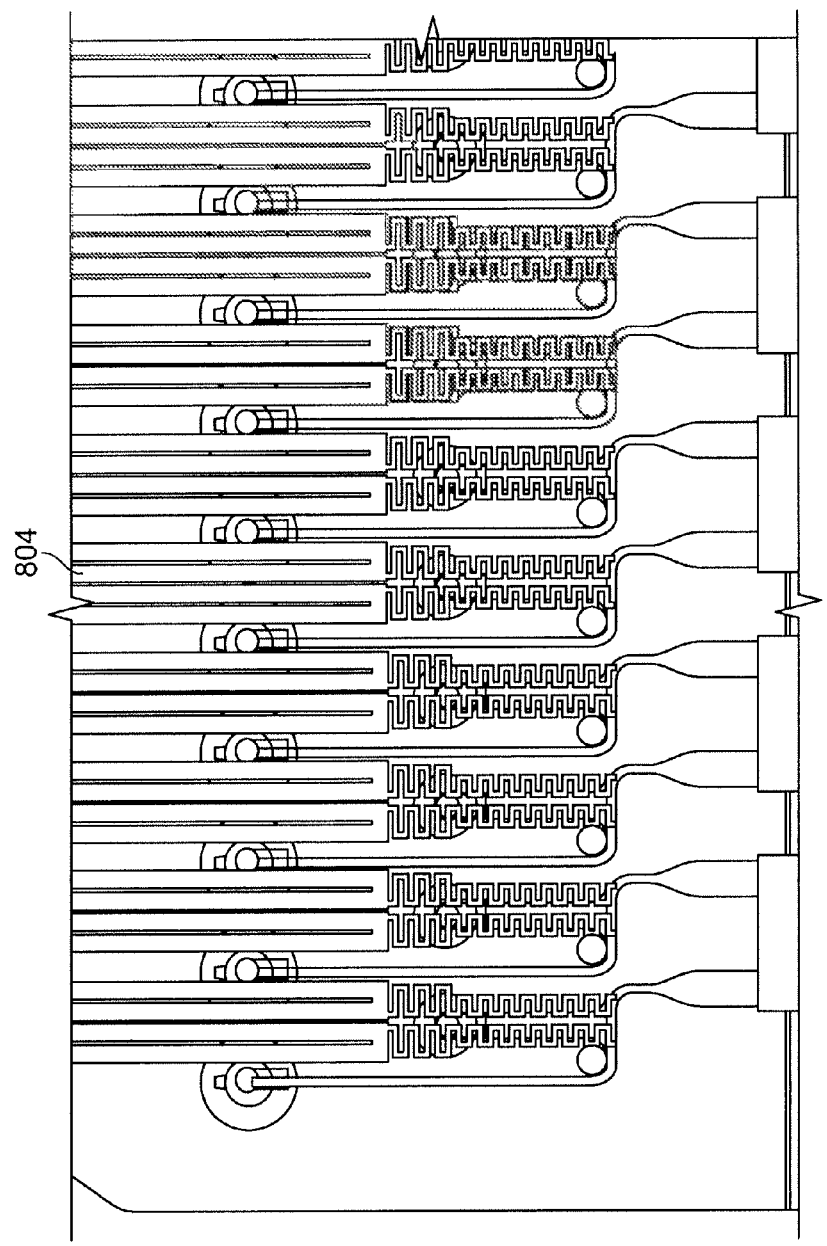
Figure 9:
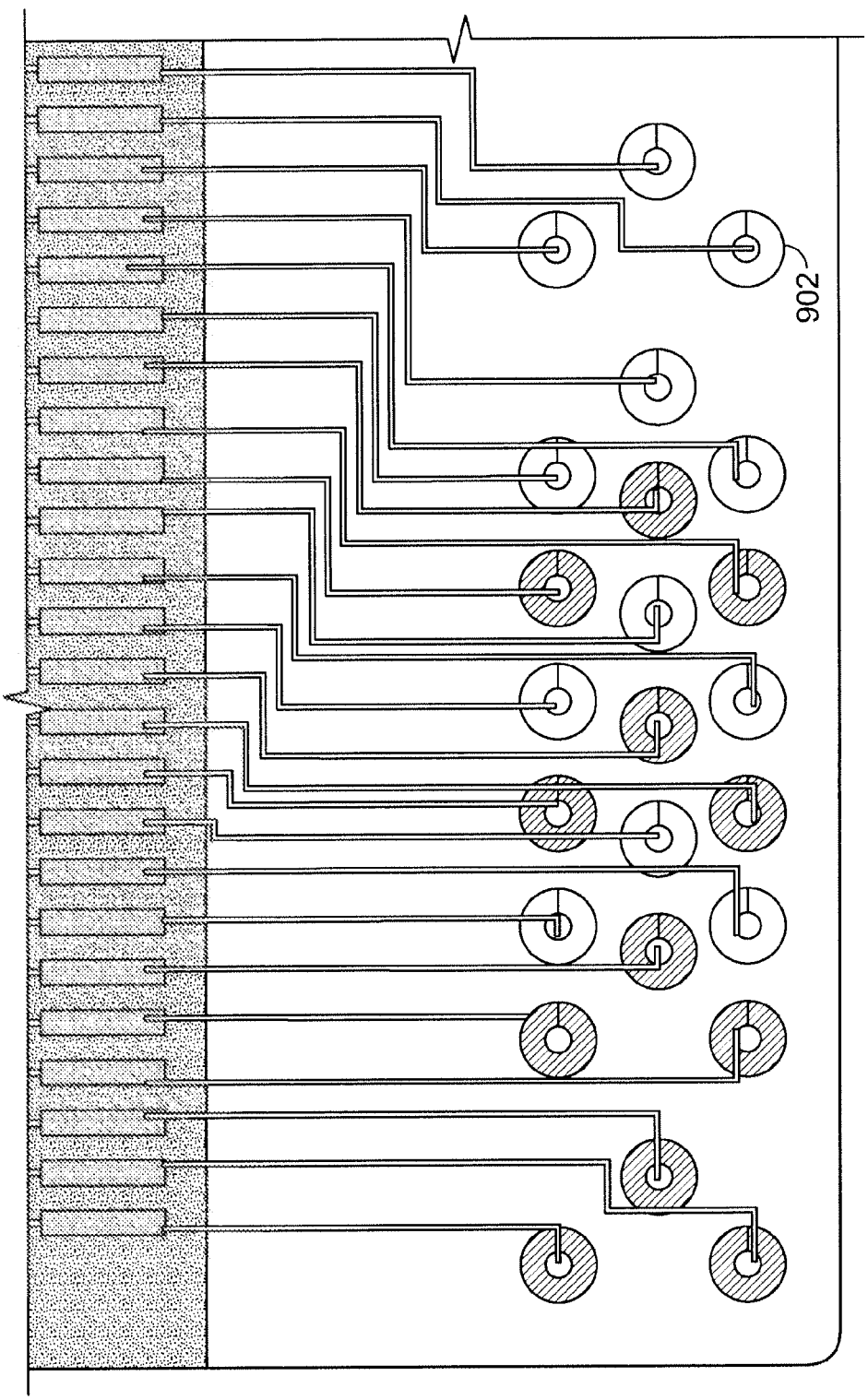

FIGS. 8 and 9 show close-ups of, respectively, heater arrays 804 compatible with, and inlets 902 on, the exemplary cartridge shown in FIG. 7.

Figure 10A:
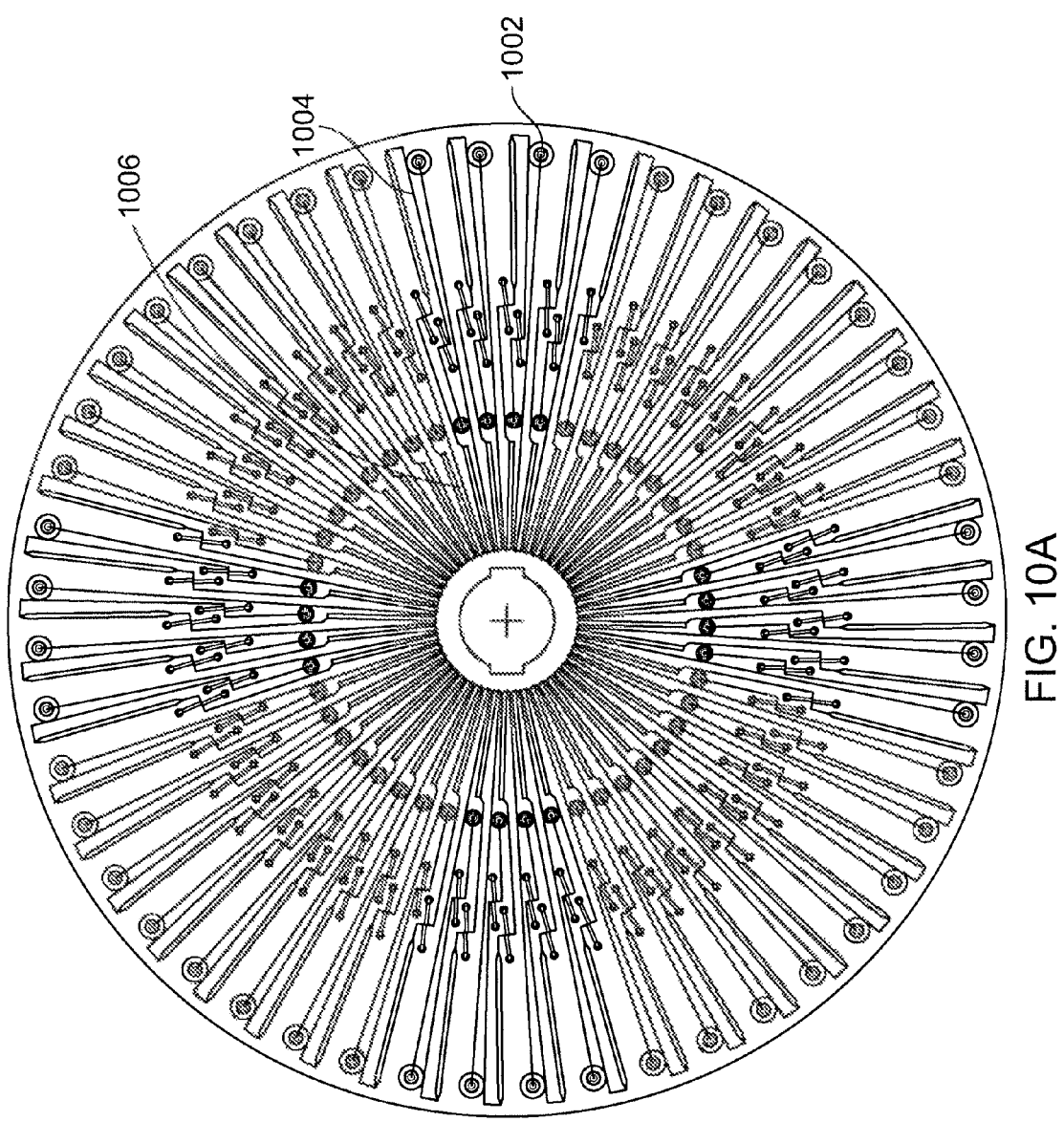
FIGS. 10A-10C show various aspects of a radially configured highly multiplexed microfluidic cartridge and associated heater array.
Figure 10B:
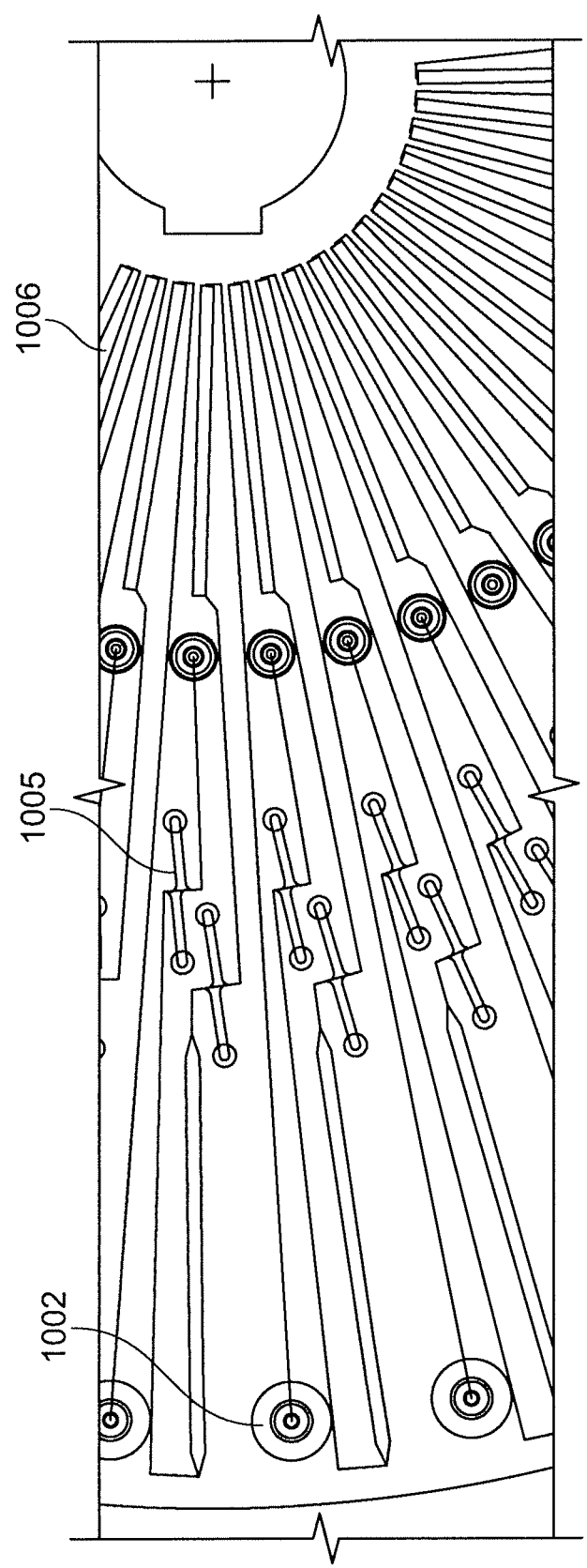
Figure 10C:
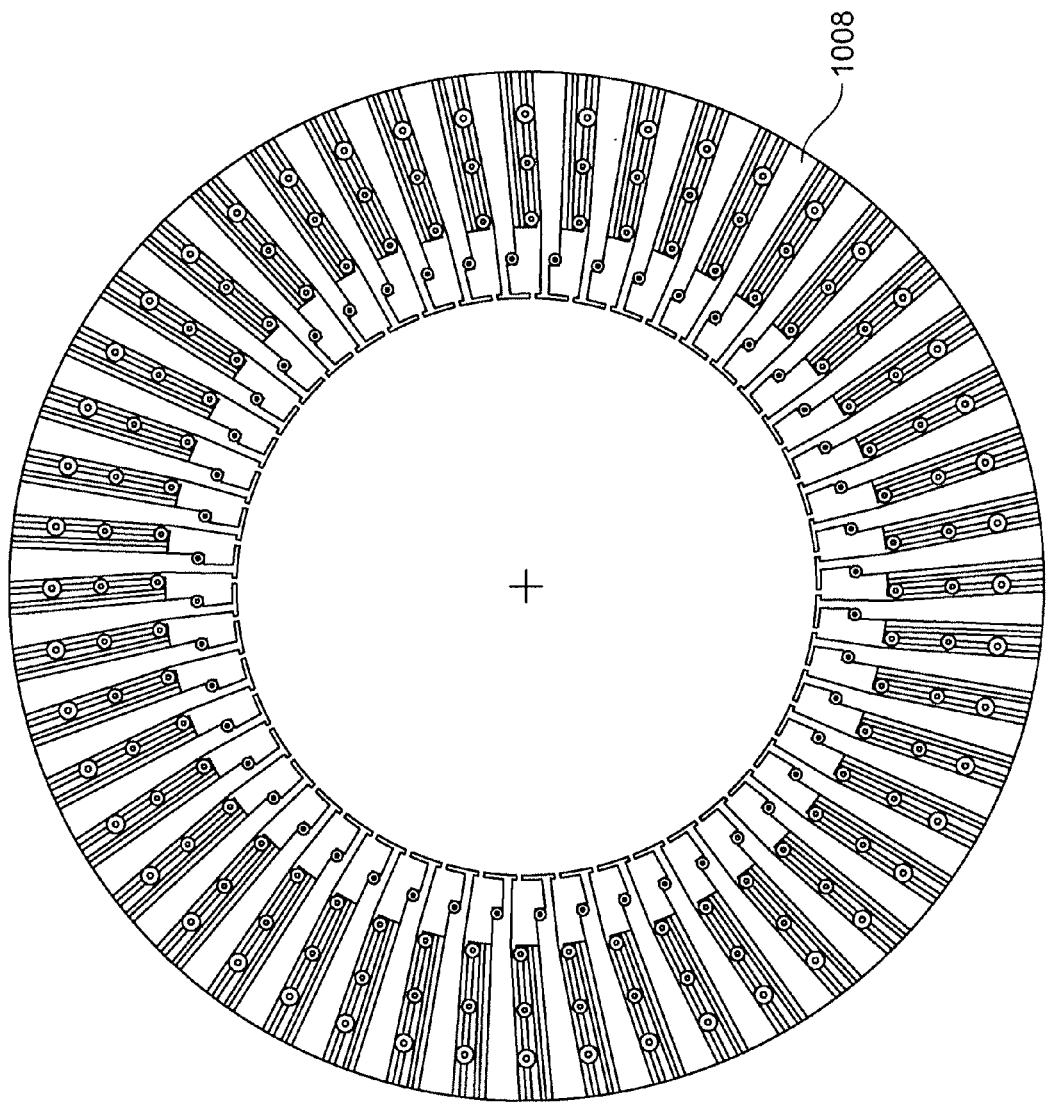

FIGS. 10A and 10B show various views of an embodiment of a radially-configured highly-multiplexed cartridge, having a number of inlets 1002, microfluidic lanes 1004, valves 1005, and PCR reaction chambers 1006. FIG. 10C shows an array of heater elements 1008 compatible with the cartridge layout of FIG. 10A.

The various embodiments shown in FIGS. 5-10C are compatible with liquid dispensers, receiving bays, and detectors that are configured differently from the other specific examples described herein.

During the design and manufacture of highly multiplexed cartridges, photolithographic processing steps such as etching, hole drilling/photo-chemical drilling/sand-blasting/ion-milling processes should be optimized to give well defined holes and microchannel pattern. Proper distances between channels should be identified and maintained to obtain good bonding between the microchannel substrate and the heat conducting substrate layer. In particular, it is desirable that minimal distances are maintained between pairs of adjacent microchannels to promote, reliable bonding of the laminate in between the channels.

The fabrication by injection molding of these complicated microfluidic structures having multiple channels and multiple inlet holes entails proper consideration of dimensional repeatability of these structures over multiple shots from the injection molding master pattern. Proper consideration is also attached to the placement of ejector pins to push out the structure from the mold without causing warp, bend or stretching of it. For example, impression of the ejector pins on the microfluidic substrate should not sink into the substrate thereby preventing planarity of the surface of the cartridge. The accurate placement of various inlet holes (such as sample inlet holes, valve inlet holes and vent holes) relative to adjacent microfluidic channels is also important because the presence of these holes can cause knit-lines to form that might cause unintended leak from a hole to a microchannel. Highly multiplexed microfluidic substrates may be fabricated in other materials such as glass, silicon.

The size of the substrate relative to the number of holes is also factor during fabrication because it is easy to make a substrate having just a simple microfluidic network with a few holes (maybe fewer than 10 holes) and a few microchannels, but making a substrate having over 24, or over 48, or over 72 holes, etc., is more difficult.

Microfluidic Networks

Particular components of exemplary microfluidic networks are further described herein.

Channels of a microfluidic network in a lane of cartridge typically have at least one sub-millimeter cross-sectional dimension. For example, channels of such a network may have a width and/or a depth of about 1 mm or less (e.g., about 750 microns or less, about 500 microns, or less, about 250 microns or less).

Figure 11:
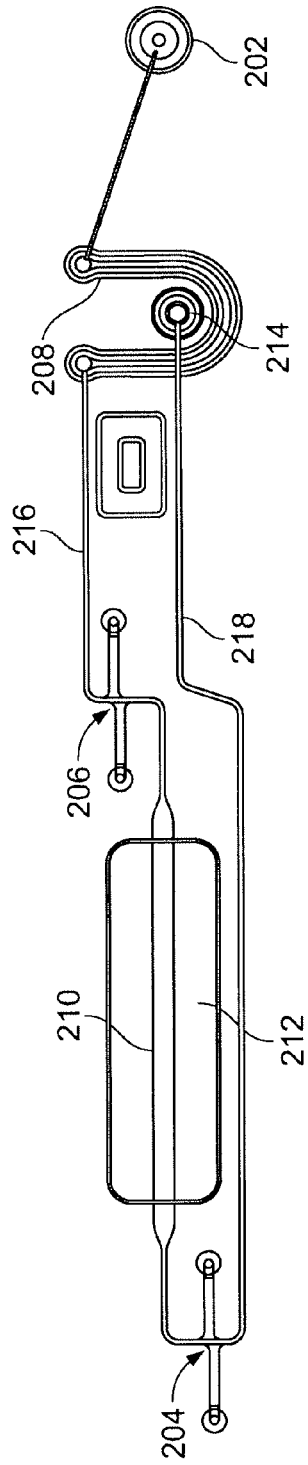
FIG. 11 shows an exemplary microfluidic network in a lane of a multi-lane cartridge such as that for FIG. 1 or 3.

FIG. 11 shows a plan view of a representative microfluidic circuit found in one lane of a multi-lane cartridge such as shown in FIGS. 2A and 2B. It would be understood by one skilled in the art that other configurations of microfluidic network would be consistent with the function of the cartridges and apparatus described herein. In operation of the cartridge, in sequence, sample is introduced through liquid inlet 202, optionally flows into a bubble removal vent channel 208 (which permits adventitious air bubbles introduced into the sample during entry, to escape), and continues along a channel 216. Typically, when using a robotic dispenser of liquid sample, the volume is dispensed accurately enough that formation of bubbles is not a significant problem, and the presence of vent channel 208 is not necessary. Thus, in certain embodiments, the bubble removal vent channel 208 is not present and sample flows directly into channel 216. Throughout the operation of cartridge 200, the fluid is manipulated as a microdroplet (not shown in FIG. 11). Valves 204 and 206 are initially both open, so that a microdroplet of sample-containing fluid can be pumped into PCR reactor channel 210 from inlet hole 202 under influence of force from the sample injection operation. Upon initiating of processing, the detector present on top of the PCR reactor 210 checks for the presence of liquid in the PCR channel, and then valves 204 and 206 are closed to isolate the PCR reaction mix from the outside. In one embodiment, the checking of the presence of liquid in the PCR channel is by measuring the heat ramp rate, such as by one or more temperature sensors in the heating unit. A channel with liquid absent will heat up faster than one in which, e.g., a sample, is present.

Both valves 204 and 206 are closed prior to thermocycling to prevent or reduce any evaporation of liquid, bubble generation, or movement of fluid from the PCR reactor. End vent 214 is configured to prevent a user from introducing an excess amount of liquid into the microfluidic cartridge, as well as playing a role of containing any sample from spilling over to unintended parts of the cartridge. A user may input sample volumes as small as an amount to fill the region from the bubble removal vent (if present) to the middle of the microreactor, or up to valve 204 or beyond valve 204. The use of microvalves prevents both loss of liquid or vapor thereby enabling even a partially filled reactor to successfully complete a PCR thermocycling reaction.

The reactor 210 is a microfluidic channel that is heated through a series of cycles to carry out amplification of nucleotides in the sample, as further described herein, and according to amplification protocols known to those of ordinary skill in the art. The inside walls of the channel in the PCR reactor are typically made very smooth and polished to a shiny finish (for example, using a polish selected from SPI A1, SPI A2, SPI A3, SPI B1, or SPI B2) during manufacture. This is in order to minimize any microscopic quantities of air trapped in the surface of the PCR channel, which would causing bubbling during the thermocycling steps. The presence of bubbles especially in the detection region of the PCR channel could also cause a false or inaccurate reading while monitoring progress of the PCR. Additionally, the PCR channel can be made shallow such that the temperature gradient across the depth of the channel is minimized.

The region of the cartridge 212 above PCR reactor 210 is a thinned down section to reduce thermal mass and autofluorescence from plastic in the cartridge. It permits a detector to more reliably monitor progress of the reaction and also to detect fluorescence from a probe that binds to a quantity of amplified nucleotide. Exemplary probes are further described herein. The region 212 can be made of thinner material than the rest of the cartridge so as to permit the PCR channel to be more responsive to a heating cycle (for example, to rapidly heat and cool between temperatures appropriate for denaturing and annealing steps), and so as to reduce glare, autofluorescence, and undue absorption of fluorescence.

After PCR has been carried out on a sample, and presence or absence of a polynucleotide of interest has been determined, it is preferred that the amplified sample remains in the cartridge and that the cartridge is either used again (if one or more lanes remain unused), or disposed of. Should a user wish to run a post amplification analysis, such as gel electrophoresis, the user may pierce a hole through the laminate of the cartridge, and recover an amount—typically about 1.5 microliter—of PCR product. The user may also place the individual PCR lane on a special narrow heated plate, maintained at a temperature to melt the wax in the valve, and then aspirate the reacted sample from the inlet hole of that PCR lane.

In various embodiments, the microfluidic network can optionally include at least one reservoir configured to contain waste.

Table 1 outlines typical volumes, pumping pressures, and operation times associated with various components of a microfluidic cartridge described herein.

TABLE 1

| Operation | Pumping Pressure | Displacement Volume | Time of Operation |
|---|---|---|---|
| Moving valve wax plugs | ~1-2 psi | <1 µl | 5-15 seconds |
| Operation | Pump Used | Pump Design | Pump Actuation |
| Moving valve wax plugs | Thermopneumatic pump | 1 µl of trapped air | Heat trapped air to ~70-90 C. |

Valves

A valve (sometimes referred to herein as a microvalve) is a component in communication with a channel, such that the valve has a normally open state allowing material to pass along a channel from a position on one side of the valve (e.g., upstream of the valve) to a position on the other side of the valve (e.g., downstream of the valve). Upon actuation of the valve, the valve transitions to a closed state that prevents material from passing along the channel from one side of the valve to the other. For example, in one embodiment, a valve can include a mass of a thermally responsive substance (TRS) that is relatively immobile at a first temperature and more mobile at a second temperature. The first and second temperatures are insufficiently high to damage materials, such as polymer layers of a microfluidic cartridge in which the valve is situated. A mass of TRS can be an essentially solid mass or an agglomeration of smaller particles that cooperate to obstruct the passage when the valve is closed. Examples of TRS's include a eutectic alloy (e.g., a solder), wax (e.g., an olefin), polymers, plastics, and combinations thereof. The TRS can also be a blend of variety of materials, such as an emulsion of thermoelastic polymer blended with air microbubbles (to enable higher thermal expansion, as well as reversible expansion and contraction), polymer blended with expancel material (offering higher thermal expansion), polymer blended with heat conducting microspheres (offering faster heat conduction and hence, faster melting profiles), or a polymer blended with magnetic microspheres (to permit magnetic actuation of the melted thermoresponsive material).

Generally, for such a valve, the second temperature is less than about 90° C. and the first temperature is less than the second temperature (e.g., about 70° C. or less). Typically, a chamber is in gaseous communication with the mass of TRS. The valve is in communication with a source of heat that can be selectively applied to the chamber of air and to the TRS. Upon heating gas (e.g., air) in the chamber and heating the mass of TRS to the second temperature, gas pressure within the chamber due to expansion of the volume of gas, forces the mass to move into the channel, thereby obstructing material from passing therealong.

Figure 12A:
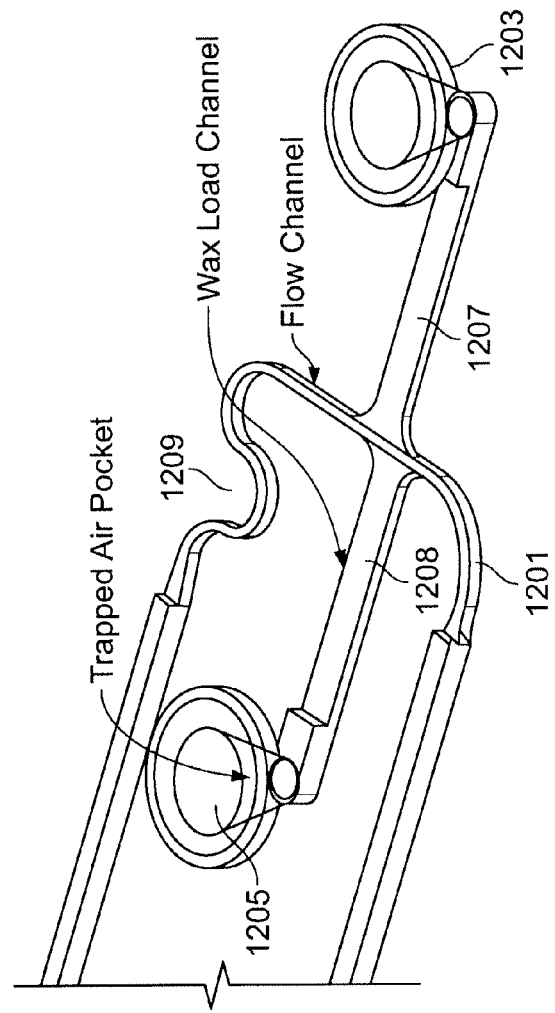
FIGS. 12A-12C show exemplary microfluidic valves, and a gate FIG. 12D.

An exemplary valve is shown in FIG. 12A. The valve of FIG. 12A has two chambers of air 1203, 1205 in contact with, respectively, each of two channels 1207, 1208 containing TRS. The air chambers also serve as loading ports for TRS during manufacture of the valve, as further described herein. In order to make the valve sealing very robust and reliable, the flow channel 1201 (along which, e.g., sample passes) at the valve junction is made narrow (typically 150 µm wide, and 150 µm deep or narrower), and the constricted portion of the flow channel is made at least 0.5 or 1 mm long such that the TRS seals up a long narrow channel thereby reducing any leakage through the walls of the channel. In the case of a bad seal, there may be leakage of fluid around walls of channel, past the TRS, when the valve is in the closed state. In order to minimize this, the flow channel is narrowed and elongated as much as possible. In order to accommodate such a length of channel on a cartridge where space may be at a premium, the flow channel can incorporate one or more curves 1209 as shown in FIG. 12A. The valve operates by heating air in the TRS-loading port, which forces the TRS forwards into the flow-channel in a manner so that it does not come back to its original position. In this way, both air and TRS are heated during operation.

Figure 12B:
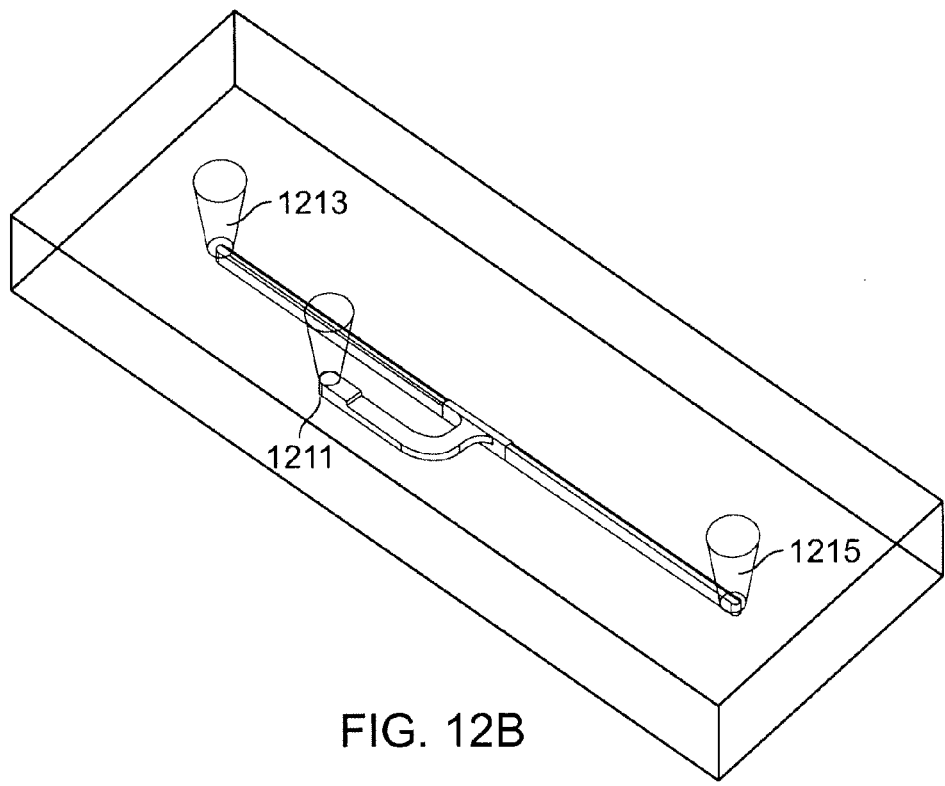

In various other embodiments, a valve for use with a microfluidic network in a microfluidic cartridge herein can be a bent valve as shown in FIG. 12B. Such a configuration reduces the footprint of the valve and hence reduces cost per part for highly dense microfluidic cartridges. A single valve loading hole 1211 is positioned in the center, that serves as an inlet for thermally responsive substance. The leftmost vent 1213 can be configured to be an inlet for, e.g., sample, and the rightmost vent 1215 acts as an exit for, e.g., air. This configuration can be used as a prototype for testing such attributes as valve and channel geometry and materials.

Figure 12C:
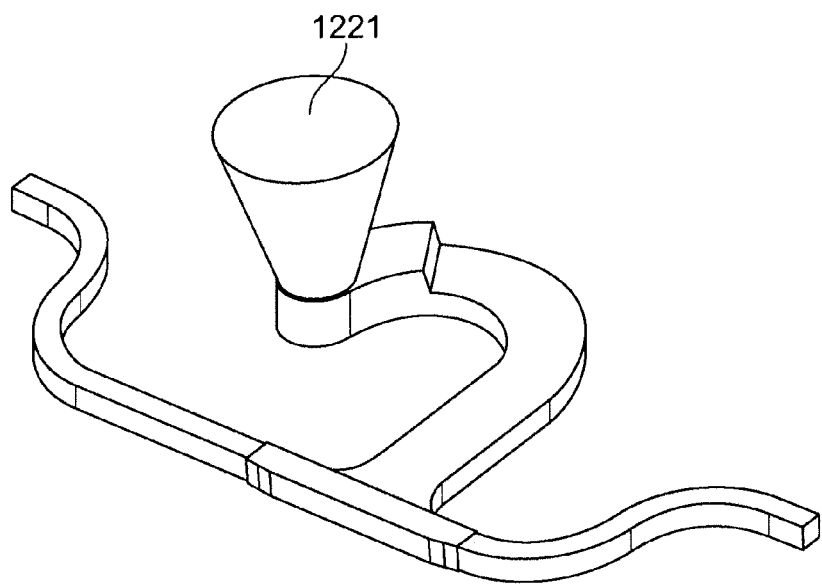

In various other embodiments, a valve for use with a microfluidic network can include a curved valve as shown in FIG. 12C, in order to reduce the effective cross-section of the valve, thereby enabling manufacture of cheaper dense microfluidic devices. Such a valve can function with a single valve loading hole and air chamber 1221 instead of a pair as shown in FIG. 12A.

Gates

Figure 12D:
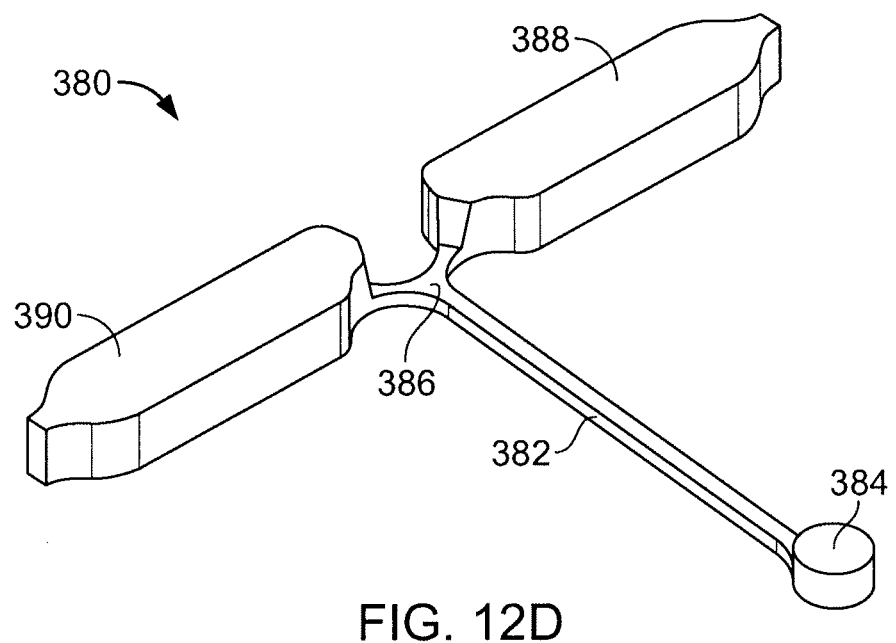

FIG. 12D shows an exemplary gate as may optionally be used in a microfluidic network herein. A gate can be a component that can have a closed state that does not allow material to pass along a channel from a position on one side of the gate to another side of the gate, and an open state that does allow material to pass along a channel from a position on one side of the gate to another side of the gate. Actuation of an open gate can transition the gate to a closed state in which material is not permitted to pass from one side of the gate (e.g., upstream of the gate) to the other side of the gate (e.g., downstream of the gate). Upon actuation, a closed gate can transition to an open state in which material is permitted to pass from one side of the gate (e.g., upstream of the gate) to the other side of the gate (e.g., downstream of the gate).

In various embodiments, a microfluidic network can include a narrow gate 380 as shown in FIG. 12D where a gate loading channel 382 used for loading wax from a wax loading hole 384 to a gate junction 386 can be narrower (e.g., approximately 150 µm wide and 100 microns deep). An upstream channel 388 as well as a downstream channel 390 of the gate junction 386 can be made wide (e.g., ~500 µm) and deep (e.g., ~500 µm) to help ensure the wax stops at the gate junction 386. The amount of gate material melted and moved out of the gate junction 386 may be minimized for optimal gate 380 opening. As an off-cartridge heater may be used to melt the thermally responsive substance in gate 380, a misalignment of the heater could cause the wax in the gate loading channel 382 to be melted as well. Therefore, narrowing the dimension of the loading channel may increase reliability of gate opening. In the case of excessive amounts of wax melted at the gate junction 386 and gate loading channel 382, the increased cross-sectional area of the downstream channel 390 adjacent to the gate junction 386 can prevent wax from clogging the downstream channel 390 during gate 380 opening. The dimensions of the upstream channel 388 at the gate junction 386 can be made similar to the downstream channel 390 to ensure correct wax loading during gate fabrication.

In various embodiments, the gate can be configured to minimize the effective area or footprint of the gate within the network and thus bent gate configurations, although not shown herein are consistent with the foregoing description.

Vents

In various embodiments, the microfluidic network can include at least one hydrophobic vent in addition to an end vent. A vent is a general outlet (hole) that may or may not be covered with a hydrophobic membrane. An exit hole is an example of a vent that need not be covered by a membrane.

A hydrophobic vent (e.g., a vent in FIG. 13) is a structure that permits gas to exit a channel while limiting (e.g., preventing) quantities of liquid from exiting the channel. Typically, hydrophobic vents include a layer of porous hydrophobic material (e.g., a porous filter such as a porous hydrophobic membrane from GE Osmonics, Minnetonka, Minn.) that defines a wall of the channel. As described elsewhere herein, hydrophobic vents can be used to position a microdroplet of sample at a desired location within a microfluidic network.

The hydrophobic vents of the present technology are preferably constructed so that the amount of air that escapes through them is maximized while minimizing the volume of the channel below the vent surface. Accordingly, it is preferable that the vent is constructed so as to have a hydrophobic membrane 1303 of large surface area and a shallow cross section of the microchannel below the vent surface.

Figure 13:
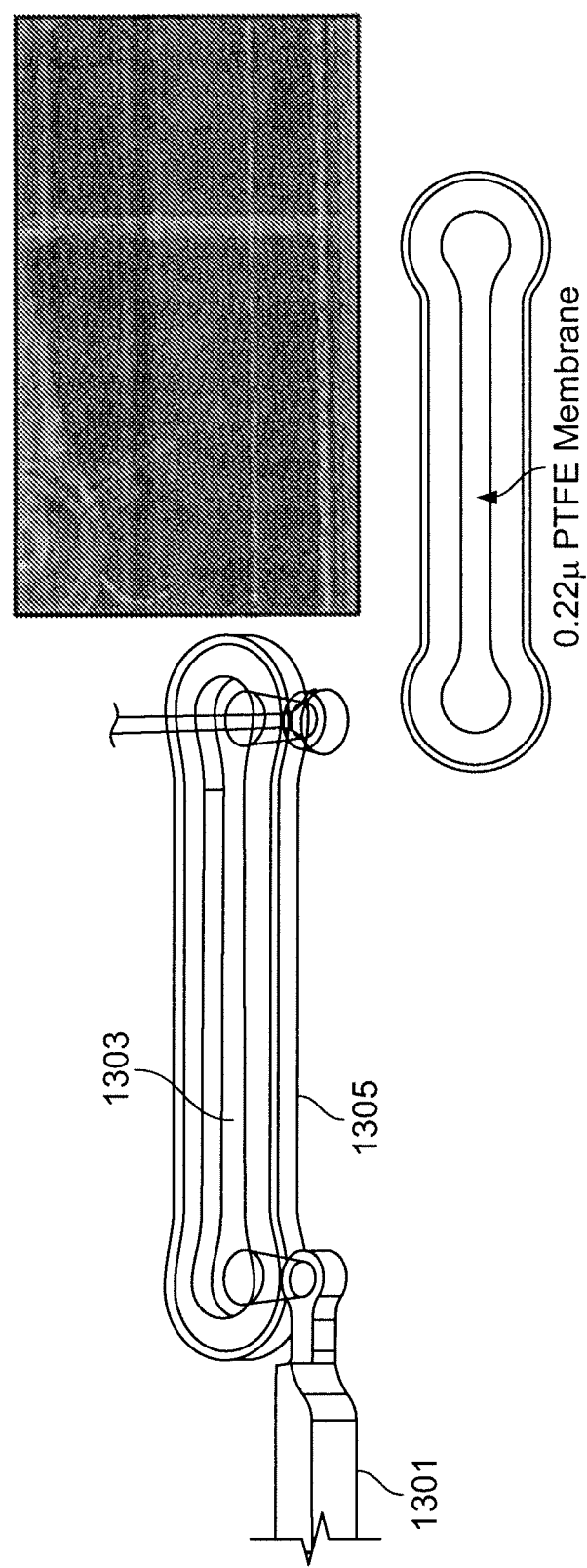
FIG. 13 shows an exemplary bubble vent.

Hydrophobic vents are useful for bubble removal and typically have a length of at least about 2.5 mm (e.g., at least about 5 mm, at least about 7.5 mm) along a channel 1305 (see FIG. 13). The length of the hydrophobic vent is typically at least about 5 times (e.g., at least about 10 times, at least about 20 times) larger than a depth of the channel within the hydrophobic vent. For example, in some embodiments, the channel depth within the hydrophobic vent is about 300 microns or less (e.g., about 250 microns or less, about 200 microns or less, about 150 microns or less).

The depth of the channel within the hydrophobic vent is typically about 75% or less (e.g., about 65% or less, about 60% or less) of the depth of the channel upstream 1301 and downstream (not shown) of the hydrophobic vent. For example, in some embodiments the channel depth within the hydrophobic vent is about 150 microns and the channel depth upstream and downstream of the hydrophobic vent is about 250 microns. Other dimensions are consistent with the description herein.

A width of the channel within the hydrophobic vent is typically at least about 25% wider (e.g., at least about 50% wider) than a width of the channel upstream from the vent and downstream from the vent. For example, in an exemplary embodiment, the width of the channel within the hydrophobic vent is about 400 microns, and the width of the channel upstream and downstream from the vent is about 250 microns. Other dimensions are consistent with the description herein.

The vent in FIG. 13 is shown in a linear configuration though it would be understood that it need not be so. A bent, kinked, curved, S-shaped, V-shaped, or U-shaped (as in item 208 FIG. 11) vent is also consistent with the manner of construction and operation described herein.

Heater Configurations to Ensure Uniform Heating of a Region

The microfluidic cartridges described herein are configured to position in a complementary receiving bay in an apparatus that contains a heater unit. The heater unit is configured to deliver heat to specific regions of the cartridge, including but not limited to one or more microfluidic components, at specific times. For example, the heat source is configured so that particular heating elements are situated adjacent to specific components of the microfluidic network of the cartridge. In certain embodiments, the apparatus uniformly controls the heating of a region of a microfluidic network. In an exemplary embodiment, multiple heaters can be configured to simultaneously and uniformly heat a single region, such as the PCR reaction chamber, of the microfluidic cartridge. In other embodiments, portions of different sample lanes are heated simultaneously and independently of one another.

Figure 14:
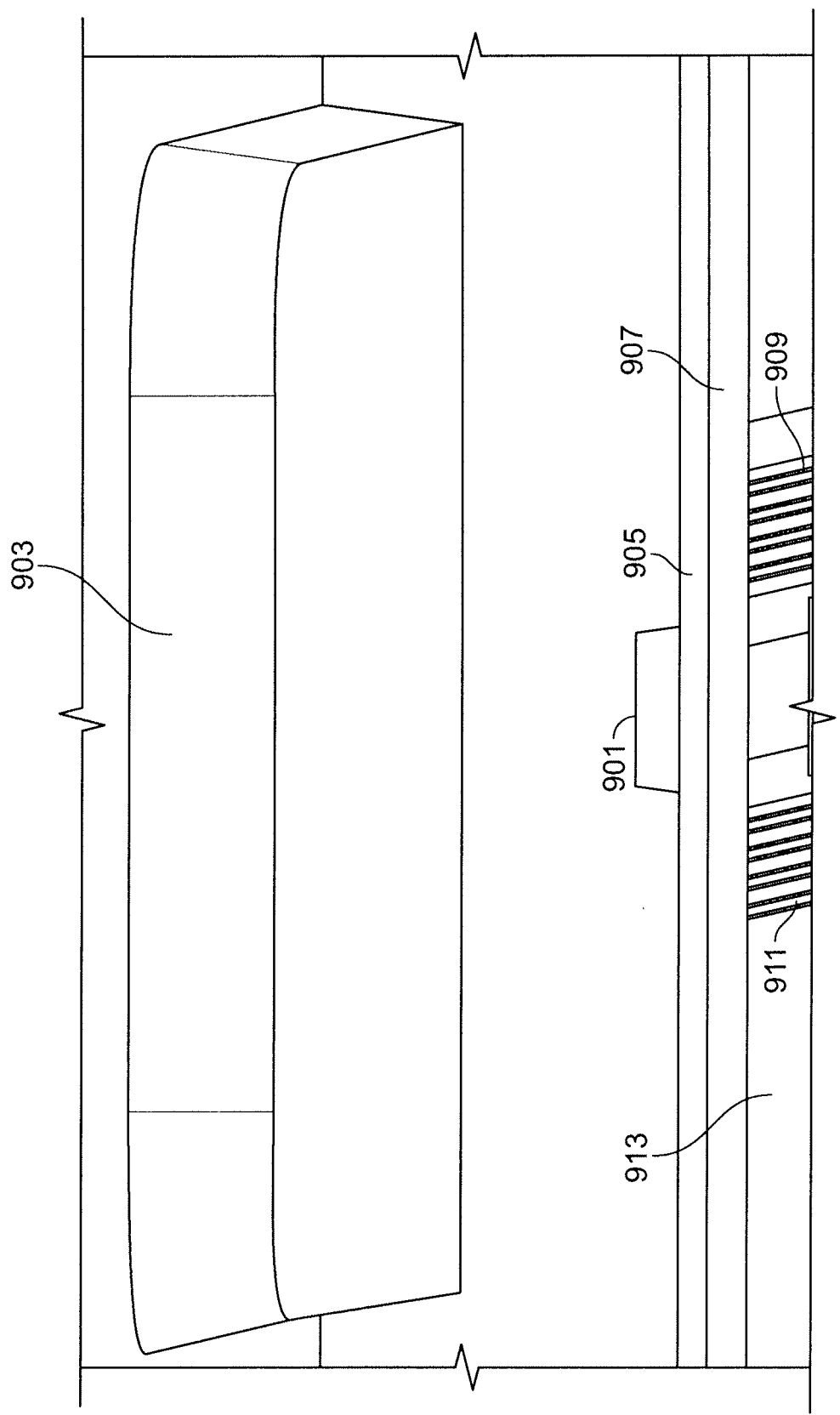
FIG. 14 shows a cross-section of a portion of a microfluidic cartridge, when in contact with a heater substrate.

FIG. 14 shows a cross-sectional view of an exemplary microfluidic cartridge to show the location of a PCR channel in relation to various heaters when the cartridge is placed in a suitable apparatus. The view in FIG. 14 is also referred to as a sectional-isometric view of the cartridge lying over a heater wafer. A window 903 above the PCR channel in the cartridge is shown in perspective view. PCR channel 901 (for example, 150µ deep×700µ wide), is shown in an upper layer of the cartridge. A laminate layer 905 of the cartridge (for example, 125µ thick) is directly under the PCR channel 901. As depicted, an optional further layer of thermal interface laminate 907 on the cartridge (for example, 125µ thick) lies directly under the laminate layer 905. Heaters 909, 911 are situated in a heater substrate layer 913 directly under the thermal interface laminate, shown in cross-section. In one embodiment the heaters are photolithographically defined and etched metal layers of gold (typically about 3,000 Å thick). Layers of 400 Å of TiW (not shown) are deposited on top and bottom of the gold layer to serve as an adhesion layer. The substrate 913 used is glass, fused silica or a quartz wafer having a thickness of 0.4 mm, 0.5 mm, 0.7 mm, or 1 mm. A thin electrically-insulative layer of 2 µm silicon oxide serves as an insulative layer on top of the metal layer. Additional thin electrically insulative layers such as 2-4 µm of Parylene may also be deposited on top of the silicon oxide surface. Two long heaters 909 and 911, as further described herein, run alongside the PCR channel.

Figure 15A:
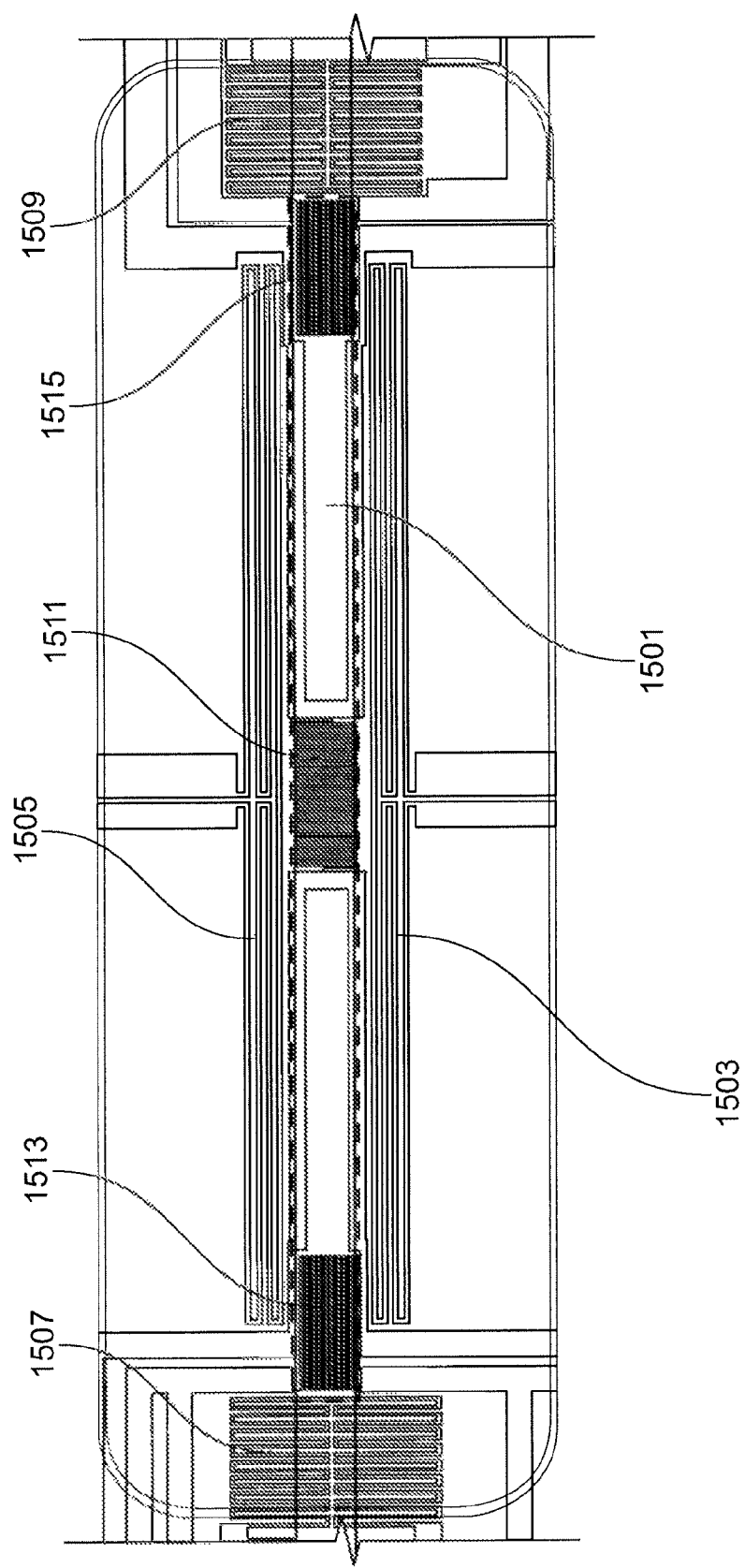
FIGS. 15A and 15B show a plan view of heater circuitry adjacent to a PCR reaction chamber.
Figure 15B:
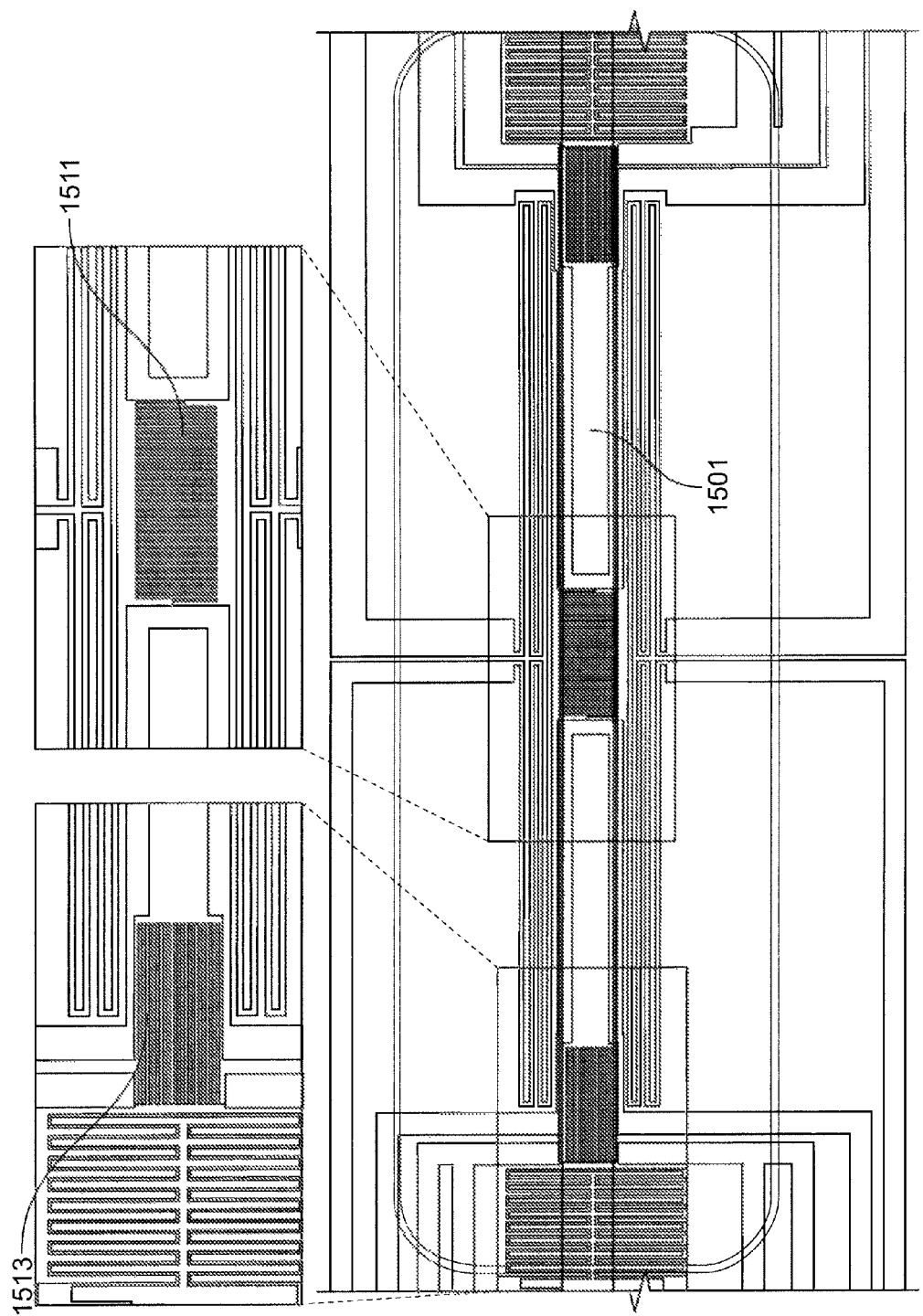

An exemplary heater array is shown in FIGS. 15A and 15B. Additional embodiments of heater arrays are described in U.S. patent application Ser. No. 11/940,315, entitled "Heater Unit for Microfluidic Diagnostic System" and filed on even date herewith, the specification of which is incorporated herein by reference in its entirety.

Referring to FIGS. 15A and 15B, an exemplary PCR reaction chamber 1501, typically having a volume ~1.6 µl, is configured with a long side and a short side, each with an associated heating element. The heater substrate therefore includes four heaters disposed along the sides of, and configured to heat, the PCR reaction chamber, as shown in the exemplary embodiment of FIG. 15A: long top heater 1505, long bottom heater 1503, short left heater 1507, and short right heater 1509. The small gap between long top heater 1505 and long bottom heater 1503 results in a negligible temperature gradient (less than 1° C. difference across the width of the PCR channel at any point along the length of the PCR reaction chamber) and therefore an effectively uniform temperature throughout the PCR reaction chamber. The heaters on the short edges of the PCR reactor provide heat to counteract the gradient created by the two long heaters from the center of the reactor to the edge of the reactor. It would be understood by one of ordinary skill in the art that still other configurations of one or more heater(s) situated about a PCR reaction chamber are consistent with the methods and apparatus described herein. For example, a 'long' side of the reaction chamber can be configured to be heated by two or more heaters. Specific orientations and configurations of heaters are used to create uniform zones of heating even on substrates having poor thermal conductivity because the poor thermal conductivity of glass, or quartz, polyimide, FR4, ceramic, or fused silica substrates is utilized to help in the independent operation of various microfluidic components such as valves and independent operation of the various PCR lanes. In FIG. 15B, various aspects of fine structure of heater elements are shown in inserts.

Generally, the heating of microfluidic components, such as a PCR reaction chamber, is controlled by passing currents through suitably configured microfabricated heaters. Under control of suitable circuitry, the lanes of a multi-lane cartridge can then be controlled independently of one another. This can lead to a greater energy efficiency of the apparatus, because not all heaters are heating at the same time, and a given heater is receiving current for only that fraction of the time when it is required to heat. Control systems and methods of controllably heating various heating elements are further described in U.S. patent application Ser. No. 11/940,315, filed Nov. 14, 2007 and entitled "Heater Unit for Microfluidic Diagnostic System".

Figure 15C:
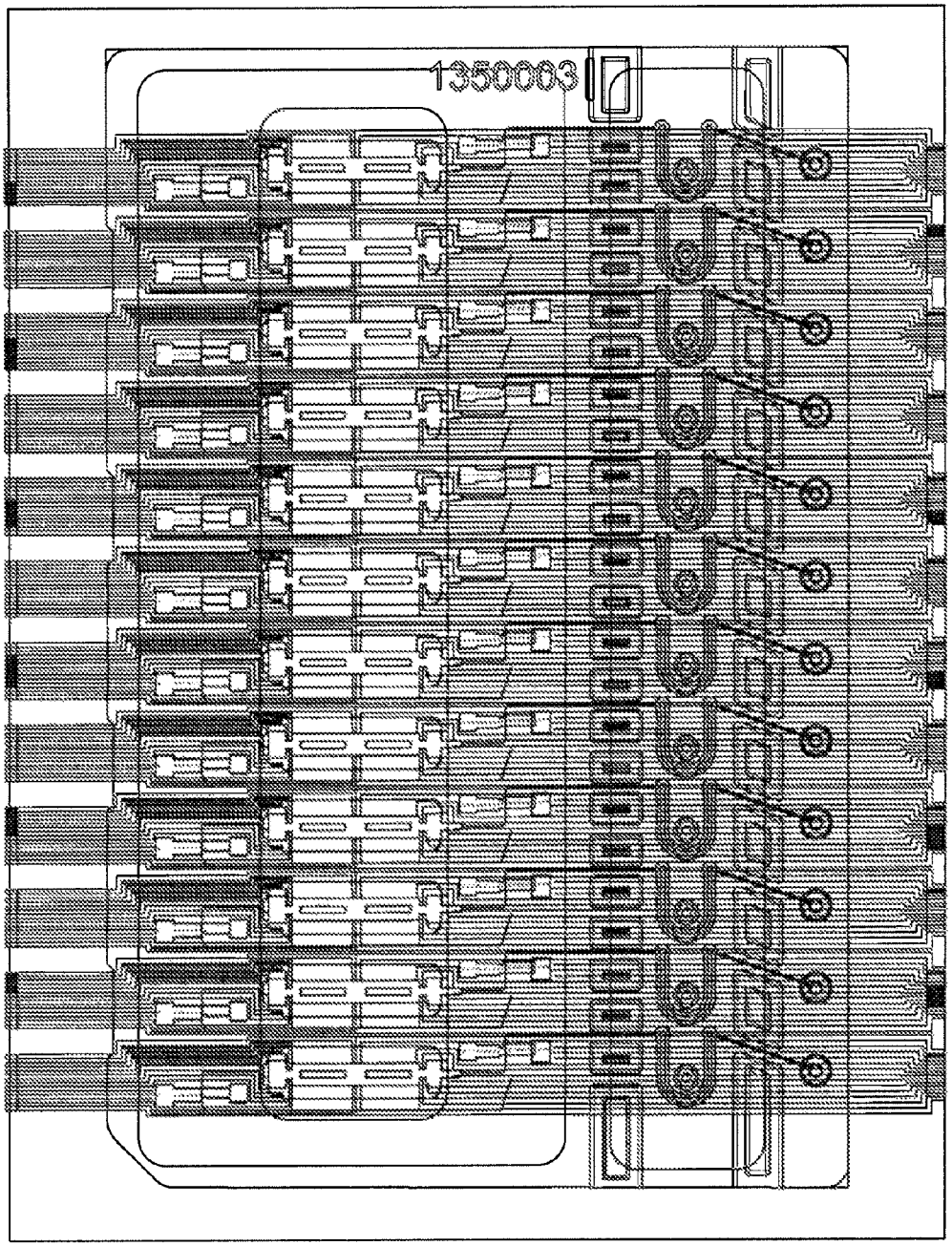
FIG. 15C shows an overlay of an array of heater elements on an exemplary multi-lane microfluidic cartridge, wherein various microfluidic networks are visible.

The configuration for uniform heating, shown in FIG. 15A for a single PCR reaction chamber, can be applied to a multi-lane PCR cartridge in which multiple independent PCR reactions occur. See, e.g., FIG. 15C, which shows an array of heater elements suitable to heat the cartridge of FIG. 1.

In other embodiments, as further described in U.S. patent application Ser. No. 11/940,315, filed Nov. 14, 2007 and entitled "Heater Unit for Microfluidic Diagnostic System", the heaters may have an associated temperature sensor, or may themselves function as sensors.

Use of Cutaways in Cartridge and Substrate to Improve Rate of Cooling During PCR Cycling During a PCR amplification of a nucleotide sample, a number of thermal cycles are carried out. For improved efficiency, the cooling between each application of heat is preferably as rapid as possible. Improved rate of cooling can be achieved with various modifications to the heating substrate and/or the cartridge, as shown in FIG. 16.

Figure 16:
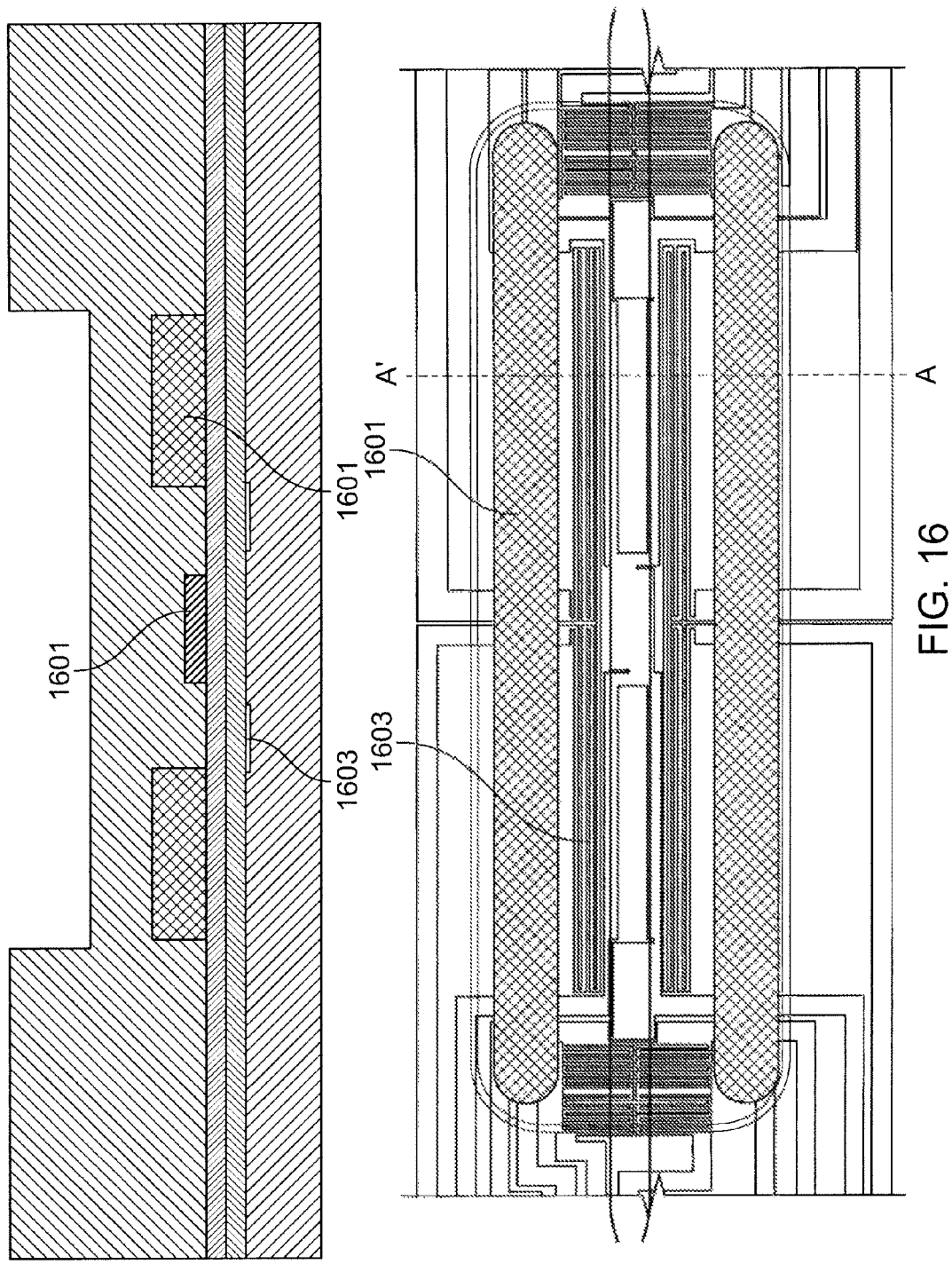
FIG. 16 shows various cut-away sections that can be used to improve cooling rates during PCR thermal cycling.

One way to achieve rapid cooling is to cutaway portions of the microfluidic cartridge substrate, as shown in FIG. 16. The upper panel of FIG. 16 is a cross-section of an exemplary microfluidic cartridge taken along the dashed line A-A' as marked on the lower panel of FIG. 16. PCR reaction chamber 1601, and representative heaters 1603 are shown. Also shown are two cutaway portions, one of which labeled 1601, that are situated alongside the heaters that are positioned along the long side of the PCR reaction chamber. Cutaway portions such as 1601 reduce the thermal mass of the cartridge, and also permit air to circulate within the cutaway portions. Both of these aspects permit heat to be conducted away quickly from the immediate vicinity of the PCR reaction chamber. Other configurations of cutouts, such as in shape, position, and number, are consistent with the present technology.

Another way to achieve rapid cooling is to cutaway portions of the heater substrate, and also to use ambient air cooling, as further described in U.S. patent application Ser. No. 11/940,315, filed Nov. 14, 2007 and entitled "Heater Unit for Microfluidic Diagnostic System".

Figure 17:
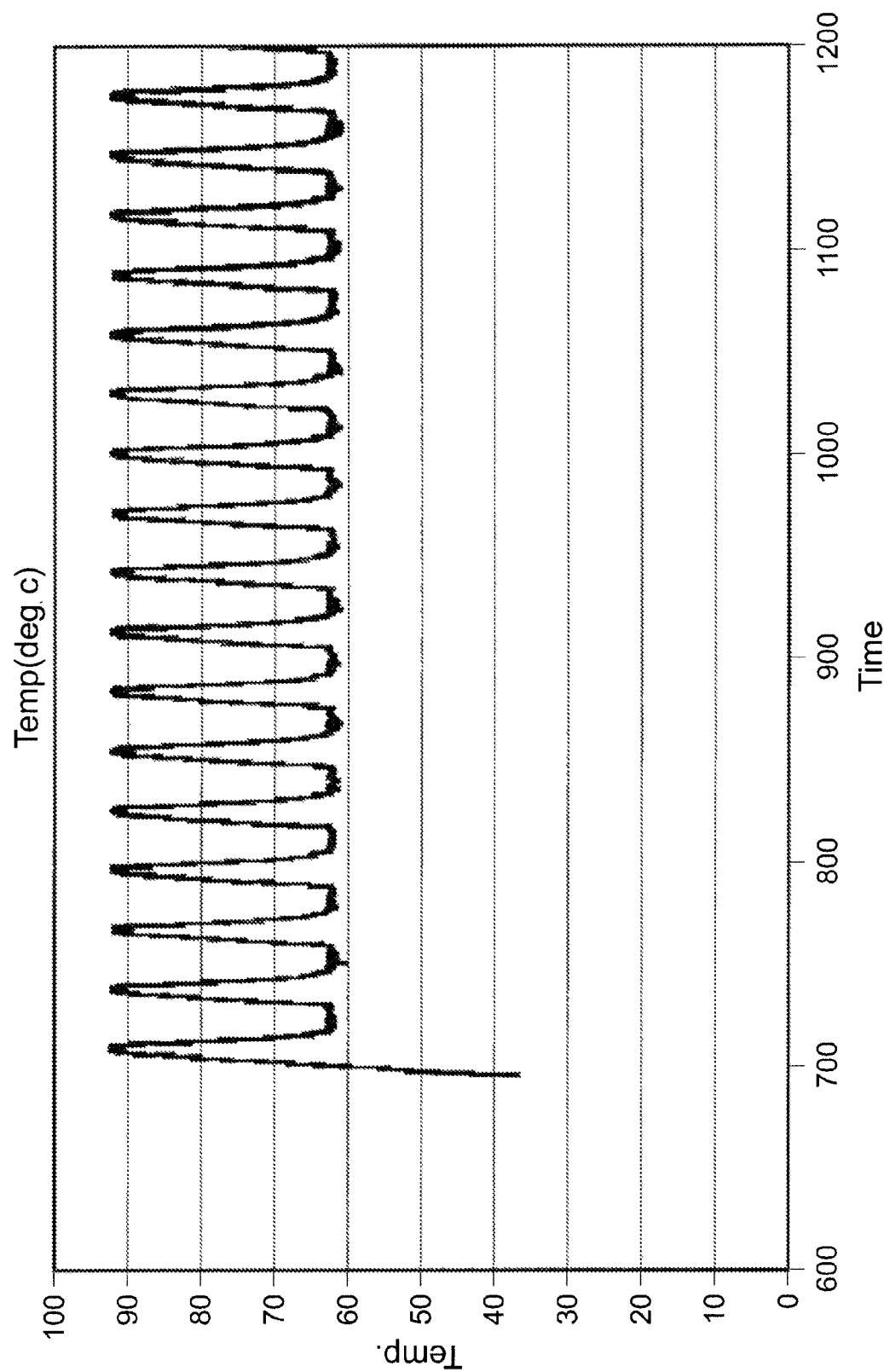
FIG. 17 shows a plot of temperature against time during a PCR process, as performed on a microfluidic cartridge as described herein.

An example of thermal cycling performance in a PCR reaction chamber obtained with a configuration as described herein, is shown in FIG. 17 for a protocol that is set to heat up the reaction mixture to 92° C., and maintain the temperature for 1 second, then cool to 62° C., and stay for 10 seconds. The cycle time shown is about 29 seconds, with 8 seconds required to heat from 62° C. and stabilize at 92° C., and 10 seconds required to cool from 92° C., and stabilize at 62° C. To minimize the overall time required for a PCR effective to produce detectable quantities of amplified material, it is important to minimize the time required for each cycle. Cycle times in the range 15-30 s, such as 18-25 s, and 20-22 s, are desirable. In general, an average PCR cycle time of 25 seconds as well as cycle times as low as 20 seconds are typical with the technology described herein. Using reaction volumes less than a microliter (such as a few hundred nanoliters or less) permits use of an associated smaller PCR chamber, and enables cycle times as low as 15 seconds.

Manufacturing Process for Cartridge

Figure 18:
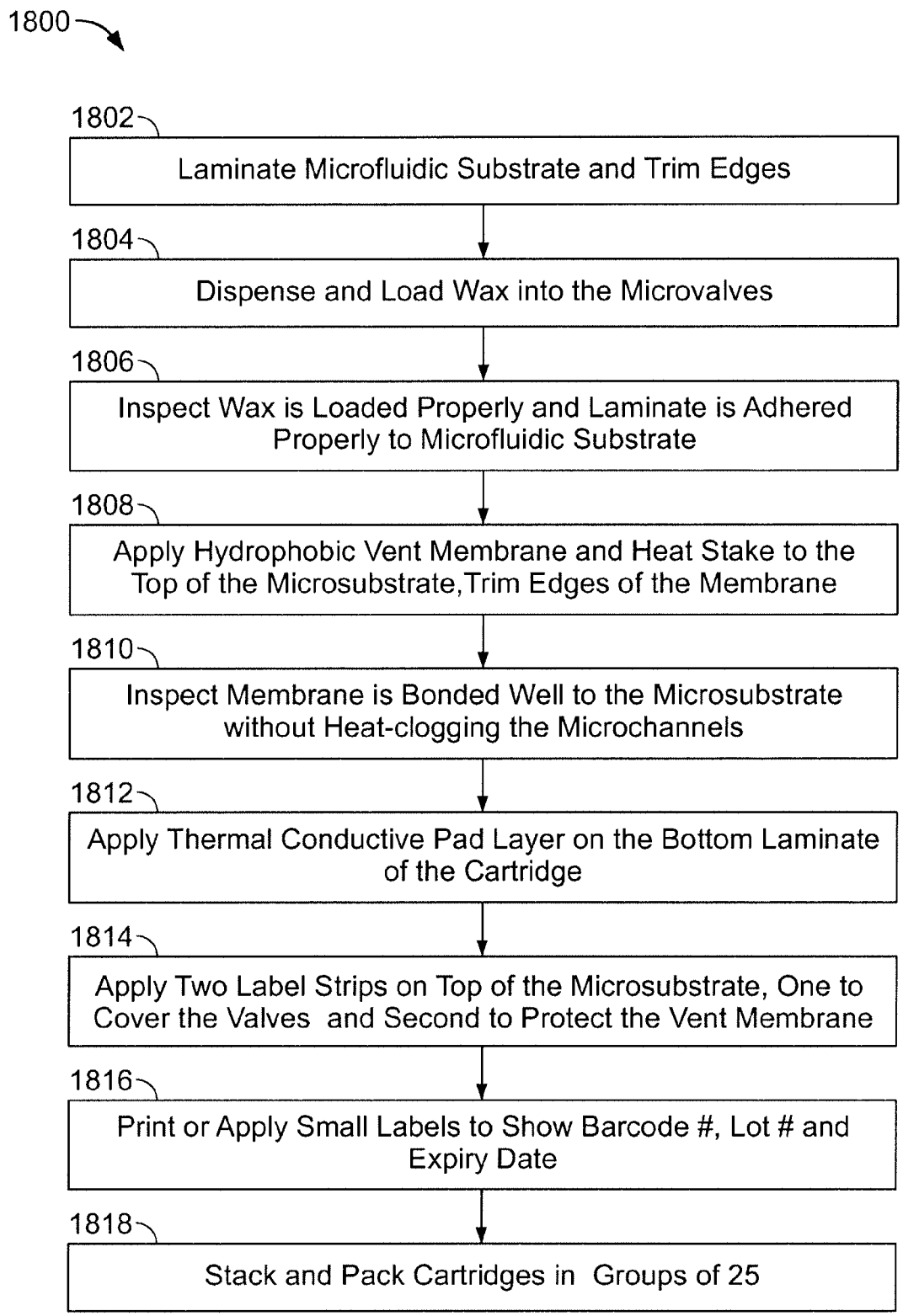
FIG. 18 shows an exemplary assembly process for a cartridge as further described herein.

FIG. 18 shows a flow-chart 1800 for an embodiment of an assembly process for an exemplary cartridge as shown in FIG. 4A herein. It would be understood by one of ordinary skill in the art, both that various steps may be performed in a different order from the order set forth in FIG. 18, and additionally that any given step may be carried out by alternative methods to those described in the figure. It would also be understood that, where separate serial steps are illustrated for carrying out two or more functions, such functions may be performed synchronously and combined into single steps and remain consistent with the overall process described herein.

At 1802, a laminate layer is applied to a microfluidic substrate that has previously been engineered, for example by injection molding, to have a microfluidic network constructed in it; edges are trimmed from the laminate where they spill over the bounds of the substrate.

At 1804, wax is dispensed and loaded into the microvalves of the microfluidic network in the microfluidic substrate. An exemplary process for carrying this out is further described herein.

At 1806, the substrate is inspected to ensure that wax from step 1804 is loaded properly and that the laminate from step 1802 adheres properly to it. If a substrate does not satisfy either or both of these tests, it is usually discarded. If substrates repeatedly fail either or both of these tests, then the wax dispensing, or laminate application steps, as applicable, are reviewed.

At 1808, a hydrophobic vent membrane is applied to, and heat bonded to, the top of the microfluidic substrate covering at least the one or more vent holes, and on the opposite face of the substrate from the laminate. Edges of the membrane that are in excess of the boundary of the substrate are trimmed.

At 1810, the assembly is inspected to ensure that the hydrophobic vent membrane is bonded well to the microfluidic substrate without heat-clogging the microfluidic channels. If any of the channels is blocked, or if the bond between the membrane and the substrate is imperfect, the assembly is discarded, and, in the case of repeated discard events, the foregoing process step 1808 is reviewed.

At 1812, optionally, a thermally conductive pad layer is applied to the bottom laminate of the cartridge.

At 1814, two label strips are applied to the top of the microfluidic substrate, one to cover the valves, and a second to protect the vent membranes. It would be understood that a single label strip may be devised to fulfill both of these roles.

At 1816, additional labels are printed or applied to show identifying characteristics, such as a barcode #, lot # and expiry date on the cartridge. Preferably one or more of these labels has a space and a writable surface that permits a user to make an identifying annotation on the label, by hand.

Optionally, at 1818, to facilitate transport and delivery to a customer, assembled and labeled cartridges are stacked, and cartridges packed into groups, such as groups of 25, or groups of 10, or groups of 20, or groups of 48 or 50. Preferably the packaging is via an inert and/or moisture-free medium.

Wax Loading in Valves

Figure 19A:
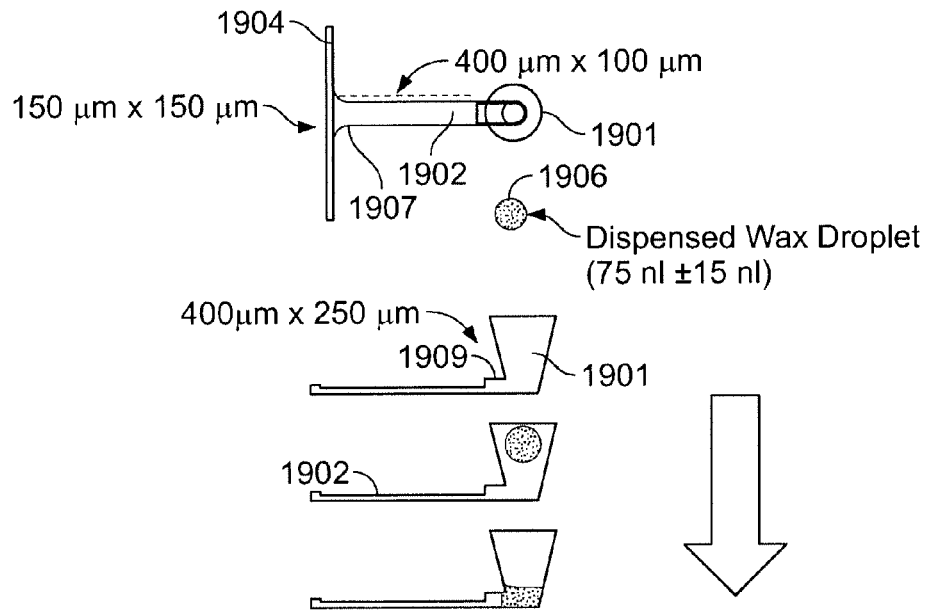
FIGS. 19A and 19B show exemplary deposition of wax droplets into microfluidic valves.
Figure 19B:
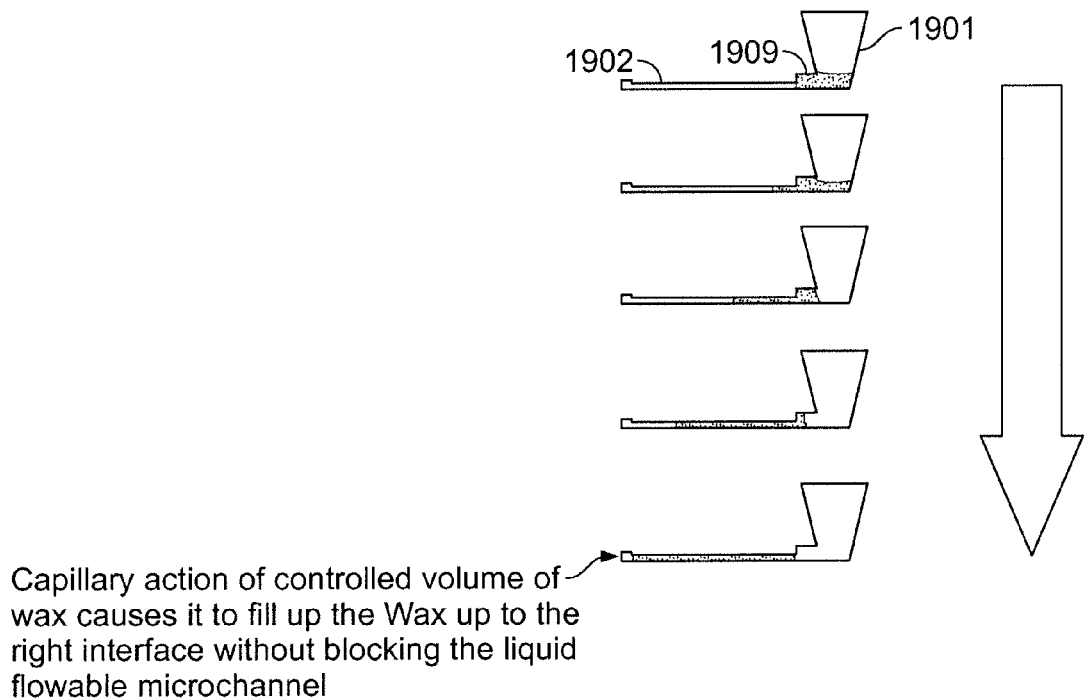

In general, a valve as shown in, e.g., FIGS. 12A-C, is constructed by depositing a precisely controlled amount of a TRS (such as wax) into a loading inlet machined in the microfluidic substrate. FIGS. 19A and 19B show how a combination of controlled hot drop dispensing into a heated microchannel device of the right dimensions and geometry is used to accurately load wax into a microchannel of a microfluidic cartridge to form a valve. The top of FIG. 19A shows a plan view of a valve inlet 1901 and loading channel 1902, connecting to a flow channel 1904. The lower portions of FIG. 19A show the progression of a dispensed wax droplet 1906 (having a volume of 75 nl±15 nl) through the inlet 1901 and into the loading channel 1902.

To accomplish those steps, a heated dispenser head can be accurately positioned over the inlet hole of the microchannel in the microfluidic device, and can dispense molten wax drops in volumes as small as 75 nanoliters with an accuracy of 20%. A suitable dispenser is also one that can deposit amounts smaller than 100 nl with a precision of +/−20%. The dispenser should also be capable of heating and maintaining the dispensing temperature of the TRS to be dispensed. For example, it may have a reservoir to hold the solution of TRS. It is also desirable that the dispense head can have freedom of movement at least in a horizontal (x-y) plane so that it can easily move to various locations of a microfluidic substrate and dispense volumes of TRS into valve inlets at such locations without having to be re-set, repositioned manually, or recalibrated in between each dispense operation.

The inlet hole of the microfluidic cartridge, or other microchannel device, is dimensioned in such a way that the droplet of 75 nl can be accurately propelled to the bottom of the inlet hole using, for example, compressed air, or in a manner similar to an inkjet printing method. The microfluidic cartridge is maintained at a temperature above the melting point of the wax thereby permitting the wax to stay in a molten state immediately after it is dispensed. After the drop falls to the bottom of the inlet hole 1901, the molten wax is drawn into the narrow channel by capillary action, as shown in the sequence of views in FIG. 19B. A shoulder between the inlet hole 1901 and the loading channel can facilitate motion of the TRS. The volume of the narrow section can be designed to be approximately equal to a maximum typical amount that is dispensed into the inlet hole. The narrow section can also be designed so that even though the wax dispensed may vary considerably between a minimum and a maximum shot size, the wax always fills up to, and stops at, the microchannel junction 1907 because the T-junction provides a higher cross section than that of the narrow section and thus reduces the capillary forces. Dimensions shown in FIG. 19A are exemplary.

PCR Reagent Mixtures

In various embodiments, the sample for introduction into a lane of the microfluidic cartridge can include a PCR reagent mixture comprising a polymerase enzyme and a plurality of nucleotides.

In various embodiments, preparation of a PCR-ready sample for use with an apparatus and cartridge as described herein can include contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid).

The PCR-ready sample can be prepared, for example, using the following steps: (1) collect sample in sample collection buffer, (2) transfer entire sample to lysis tube, mix, heat, and incubate for seven minutes, (3) place on magnetic rack, allow beads to separate, aspirate supernatant, (4) add 100 µl of Buffer 1, mix, place on magnetic rack, allow beads to separate, aspirate supernatant, (5) add 10 µl of Buffer 2, mix, place in high temperature heat block for 3 minutes, place on magnetic rack, allow beads to separate, transfer 5 µl supernatant, and (6) Add 5 µl of Buffer 3, transfer 1 to 10 µl of supernatant for PCR amplification and detection.

The PCR reagent mixture can be in the form of one or more lyophilized pellets and the steps by which the PCR-ready sample is prepared can involve reconstituting the PCR pellet by contacting it with liquid to create a PCR reagent mixture solution. In yet another embodiment, each of the PCR lanes may have dried down or lyophilized ASR reagents preloaded such that the user only needs to input prepared polynucleotide sample into the PCR. In another embodiment, the PCR lanes may have only the application-specific probes and primers pre-measured and pre-loaded, and the user inputs a sample mixed with the PCR reagents.

In various embodiments, the PCR-ready sample can include at least one probe that can be selective for a polynucleotide sequence, wherein the steps by which the PCR-ready sample is prepared involve contacting the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye.

In various embodiments, the PCR-ready sample further includes a sample buffer.

In various embodiments, the PCR-ready sample includes at least one probe that is selective for a polynucleotide sequence, e.g., the polynucleotide sequence that is characteristic of a pathogen selected from the group consisting of gram positive bacteria, gram negative bacteria, yeast, fungi, protozoa, and viruses.

In various embodiments, the PCR reagent mixture can further include a polymerase enzyme, a positive control plasmid and a fluorogenic hybridization probe selective for at least a portion of the plasmid.

In various embodiments, the probe can be selective for a polynucleotide sequence that is characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, wild animals, extinct organisms, bacteria, fungi, viruses, plants, and the like. The probe can also be selective for components of organisms that employ their own polynucleotides, for example mitochondria. In some embodiments, the probe is selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe is selective for organisms selected from the group consisting of gram positive bacteria, gram negative bacteria, yeast, fungi, protozoa, and viruses.

In various embodiments, the probe can be selective for a polynucleotide sequence that is characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus* (e.g., α, β or γ-hemolytic, Group A, B, C, D or G) such as *S. pyogenes, S. agalactiae; E. faecalis, E. durans*, and *E. faecium* (formerly *S. faecalis, S. durans, S. faecium*); nonenterococcal group D streptococci, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniae; S. pneumoniae; Neisseria*, e.g., *N. meningitides, N. gonorrhoeae, saprophytic Neisseria* sp; *Erysipelothrix*, e.g., *E. rhusiopathiae; Listeria* spp., e.g., *L. monocytogenes*, rarely *L. ivanovii* and *L. seeligeri; Bacillus*, e.g., *B. anthracis, B. cereus, B. subtilis, B. subtilus niger, B. thuringiensis; Nocardia asteroids; Legionella*, e.g., *L. pneumonophilia, Pneumocystis*, e.g., *P. carinii;* Enterobacteriaceae such as *Salmonella, Shigella, Escherichia* (e.g., *E. coli, E. coli*O157:H7); *Klebsiella, Enterobacter, Serratia, Proteus, Morganella, Providencia, Yersinia*, and the like, e.g., *Salmonella*, e.g., *S. typhi S. paratyphi* A, B (*S. schottmuelleri*), and C (*S. hirschfeldii*), *S. dublin S. choleraesuis, S. enteritidis, S. typhimurium, S. heidelberg, S. newport, S. infantis, S. agona, S. montevideo*, and *S. saint-paul; Shigella* e.g., subgroups: A, B, C, and D, such as *S. flexneri, S. sonnei, S. boydii, S. dysenteriae; Proteus* (*P. mirabilis, P. vulgaris*, and *P. myxofaciens*), *Morganella* (*M. morganii*); *Providencia* (*P. rettgeri, P. alcalifaciens*, and *P. stuartii*); *Yersinia*, e.g., *Y. pestis, Y. enterocolitica; Haemophilus*, e.g., *H. influenzae, H. parainfluenzae H. aphrophilus, H. ducreyi; Brucella*, e.g., *B. abortus, B. melitensis, B. suis, B. canis; Francisella*, e.g., *F. tularensis; Pseudomonas*, e.g., *P. aeruginosa, P. paucimobilis, P. putida, P. fluorescens, P. acidovorans, Burkholderia* (*Pseudomonas*) *pseudomallei, Burkholderia mallei, Burkholderia cepacia* and *Stenotrophomonas maltophilia; Campylobacter*, e.g., *C. fetus fetus, C. jejuni, C. pylori* (*Helicobacter pylori*); *Vibrio*, e.g., *V. cholerae, V. parahaemolyticus, V. mimicus, V. alginolyticus, V. hollisae, V. vulnificus*, and the nonagglutinable *vibrios; Clostridia*, e.g., *C. perfringens, C. tetani, C. difficile, C. botulinum; Actinomyces*, e.g., *A. israelii; Bacteroides*, e.g., *B. fragilis, B. thetaiotaomicron, B. distasonis, B. vulgatus, B. ovatus, B. caccae*, and *B. merdae; Prevotella*, e.g., *P. melaminogenica*; genus *Fusobacterium; Treponema*, e.g. *T. pallidum* subspecies *endemicum, T. pallidum* subspecies *pertenue, T. carateum*, and *T. pallidum* subspecies *pallidum*; genus *Borrelia*, e.g., *B burgdorferi*; genus *Leptospira; Streptobacillus*, e.g., *S. moniliformis; Spirillum*, e.g., *S. minus; Mycobacterium*, e.g., *M. tuberculosis, M. bovis, M. africanum, M. avium M. intracellulare, M. kansasii, M. xenopi, M. marinum, M. ulcerans*, the *M. fortuitum* complex (*M. fortuitum* and *M. chelonei*), *M. leprae, M. asiaticum, M. chelonei* subsp. *abscessus, M. fallax, M. fortuitum, M. malmoense, M. shimoidei, M. simiae, M. szulgai, M. xenopi; Mycoplasma*, e.g., *M. hominis, M. orale, M. salivarium, M.*

*fermentans, M. pneumoniae, M. bovis, M. tuberculosis, M. avium, M. leprae; Mycoplasma*, e.g., *M. genitalium; Ureaplasma*, e.g., *U. urealyticum; Trichomonas*, e.g., *T. vaginalis; Cryptococcus*, e.g., *C. neoformans; Histoplasma*, e.g., *H. capsulatum; Candida*, e.g., *C. albicans; Aspergillus* sp; *Coccidioides*, e.g., *C. immitis; Blastomyces*, e.g. *B. dermatitidis; Paracoccidioides*, e.g., *P. brasiliensis; Penicillium*, e.g., *P. marneffei; Sporothrix*, e.g., *S. schenckii; Rhizopus, Rhizomucor, Absidia*, and *Basidiobolus*; diseases caused by *Bipolaris, Cladophialophora, Cladosporium, Drechslera, Exophiala, Fonsecaea, Phialophora, Xylohypha, Ochroconis, Rhinocladiella, Scolecobasidium*, and *Wangiella; Trichosporon*, e.g., *T. beigelii; Blastoschizomyces*, e.g., *B. capitatus; Plasmodium*, e.g., *P. falciparum, P. vivax, P. ovale*, and *P. malariae; Babesia* sp; protozoa of the genus *Trypanosoma*, e.g., *T. cruzi; Leishmania*, e.g., *L. donovani, L. major L. tropica, L. mexicana, L. braziliensis, L. viannia braziliensis; Toxoplasma*, e.g., *T. gondii*; Amoebas of the genera *Naegleria* or *Acanthamoeba; Entamoeba histolytica; Giardia lamblia*; genus *Cryptosporidium*, e.g., *C. parvum; Isospora belli; Cyclospora cayetanensis; Ascaris lumbricoides; Trichuris trichiura; Ancylostoma duodenale* or *Necator americanus; Strongyloides stercoralis Toxocara*, e.g., *T. canis, T. cati; Baylisascaris*, e.g., *B. procyonis; Trichinella*, e.g., *T. spiralis; Dracunculus*, e.g., *D. medinensis*; genus *Filarioidea; Wuchereria bancrofti; Brugia*, e.g., *B. malayi*, or *B. timori; Onchocerca volvulus; Loa loa; Dirofilaria immitis*; genus *Schistosoma*, e.g., *S. japonicum, S. mansoni, S. mekongi, S. intercalatum, S. haematobium; Paragonimus*, e.g., *P. Westermani, P. Skriabini; Clonorchis sinensis; Fasciola hepatica; Opisthorchis* sp; *Fasciolopsis buski; Diphyllobothrium latum; Taenia*, e.g., *T. saginata, T. solium; Echinococcus*, e.g., *E. granulosus, E. multilocularis*; Picornaviruses, rhinoviruses echoviruses, coxsackieviruses, influenza virus; paramyxoviruses, e.g., types 1, 2, 3, and 4; adnoviruses; Herpesviruses, e.g., HSV-1 and HSV-2; varicella-zoster virus; human T-lymphotrophic virus (type I and type II); Arboviruses and Arenaviruses; Togaviridae, Flaviviridae, Bunyaviridae, Reoviridae; Flavivirus; Hantavirus; Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Smallpox (variola); retroviruses e.g., human immunodeficiency viruses 1 and 2; human papillomavirus [HPV] types 6, 11, 16, 18, 31, 33, and 35.

In various embodiments, the probe can be selective for a polynucleotide sequence that is characteristic of an organisms selected from the group consisting of *Pseudomonas aeruginosa, Proteus mirabilis, Klebsiella oxytoca, Klebsiella pneumoniae, Escherichia coli, Acinetobacter Baumannii, Serratia marcescens, Enterobacter aerogenes, Enterococcus faecium*, vancomycin-resistant enterococcus (VRE), *Staphylococcus aureus*, methecillin-resistant *Staphylococcus aureus*(MRSA), *Streptococcus viridans, Listeria monocytogenes, Enterococcus* spp., *Streptococcus* Group B, *Streptococcus* Group C, *Streptococcus* Group G, *Streptococcus* Group F, *Enterococcus faecalis, Streptococcus pneumoniae, Staphylococcus epidermidis, Gardenerella vaginalis, Micrococcus* sps., *Haemophilus influenzae, Neisseria gonorrhoeee, Moraxella catarrahlis, Salmonella* sps., *Chlamydia trachomatis, Peptostreptococcus productus, Peptostreptococcus anaerobius, Lactobacillus fermentum, Eubacterium lentum, Candida glabrata, Candida albicans, Chlamydia* spp., *Camplobacter* spp., *Salmonella* spp., smallpox (variola major), *Yersina Pestis*, Herpes Simplex Virus I (HSV I), and Herpes Simplex Virus II (HSV II).

In various embodiments, the probe can be selective for a polynucleotide sequence that is characteristic of Group B *Streptococcus*.

In various embodiments, a method of carrying out PCR on a sample can further include one of more of the following steps: heating the biological sample in the microfluidic cartridge; pressurizing the biological sample in the microfluidic cartridge at a pressure differential compared to ambient pressure of between about 20 kilopascals and 200 kilopascals, or in some embodiments, between about 70 kilopascals and 110 kilopascals.

In some embodiments, the method for sampling a polynucleotide can include the steps of: placing a microfluidic cartridge containing a PCR-ready sample in a receiving bay of a suitably configured apparatus; carrying out PCR on the sample under thermal cycling conditions suitable for creating PCR amplicons from the neutralized polynucleotide in the sample, the PCR-ready sample comprising a polymerase enzyme, a positive control plasmid, a fluorogenic hybridization probe selective for at least a portion of the plasmid, and a plurality of nucleotides; contacting the neutralized polynucleotide sample or a PCR amplicon thereof with the at least one fluorogenic probe that is selective for a polynucleotide sequence, wherein the probe is selective for a polynucleotide sequence that is characteristic of an organism selected from the group consisting of gram positive bacteria, gram negative bacteria, yeast, fungi, protozoa, and viruses; and detecting the fluorogenic probe, the presence of the organism for which the one fluorogenic probe is selective is determined.

Carrying out PCR on a PCR-ready sample can additionally include: independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, a method of using the apparatus and cartridge described herein can further include one or more of the following steps: determining the presence of a polynucleotide sequence in the biological sample, the polynucleotide sequence corresponding to the probe, if the probe is detected in the neutralized polynucleotide sample or a PCR amplicon thereof; determining that the sample was contaminated if the probe is detected in the negative control polynucleotide or a PCR amplicon thereof; and/or in some embodiments, wherein the PCR reagent mixture further comprises a positive control plasmid and a plasmid probe selective for at least a portion of the plasmid, the method further including determining that a PCR amplification has occurred if the plasmid probe is detected.

Kit

In various embodiments, the microfluidic cartridge as described herein can be provided in the form of a kit, wherein the kit can include a microfluidic cartridge, and a liquid transfer member (such as a syringe or a pipette). In various embodiments, the kit can further include instructions to employ the liquid transfer member to transfer a sample containing extracted nucleic acid from a sample container via a sample inlet to the microfluidic network on the microfluidic cartridge. In some embodiments, the microfluidic cartridge and the liquid transfer member can be sealed in a pouch with an inert gas.

Typically when transferring a sample from liquid dispenser, such as a pipette tip, to an inlet on the microfluidic cartridge, a volume of air is simultaneously introduced into the microfluidic network, the volume of air being between about 0.5 mL and about 5 mL. Presence of air in the microfluidic network, however, is not essential to operation of the cartridge described herein.

In various embodiments, the kit can further include at least one computer-readable label on the cartridge. The label can include, for example, a bar code, a radio frequency tag or one or more computer-readable characters. When used in conjunction with a similar computer-readable label on a sample container, such as a vial or a pouch, matching of diagnostic results with sample is thereby facilitated.

In some embodiments, a sample identifier of the apparatus described elsewhere herein is employed to read a label on the microfluidic cartridge and/or a label on the biological sample.

Overview of an Apparatus for Receiving a Microfluidic Cartridge

The present technology relates to a cartridge, complementary apparatus, and related methods for amplifying, and carrying out diagnostic analyses on, nucleotides from biological samples. The technology includes a disposable or reusable microfluidic cartridge containing multiple sample lanes capable of processing samples in parallel as described elsewhere herein, and a reusable apparatus that is configured to selectively actuate on-cartridge operations, to detect and analyze the products of the PCR amplification in each of the lanes separately, in all simultaneously, or in groups simultaneously, and, optionally, can display the progression of analyses and results thereof on a graphical user interface. Such a reusable apparatus is further described in U.S. patent application Ser. No. 11/985,577, entitled "Microfluidic System for Amplifying and Detecting Polynucleotides in Parallel" and filed on Nov. 14, 2007, and which is incorporated herein by reference in its entirety.

Figure 20:
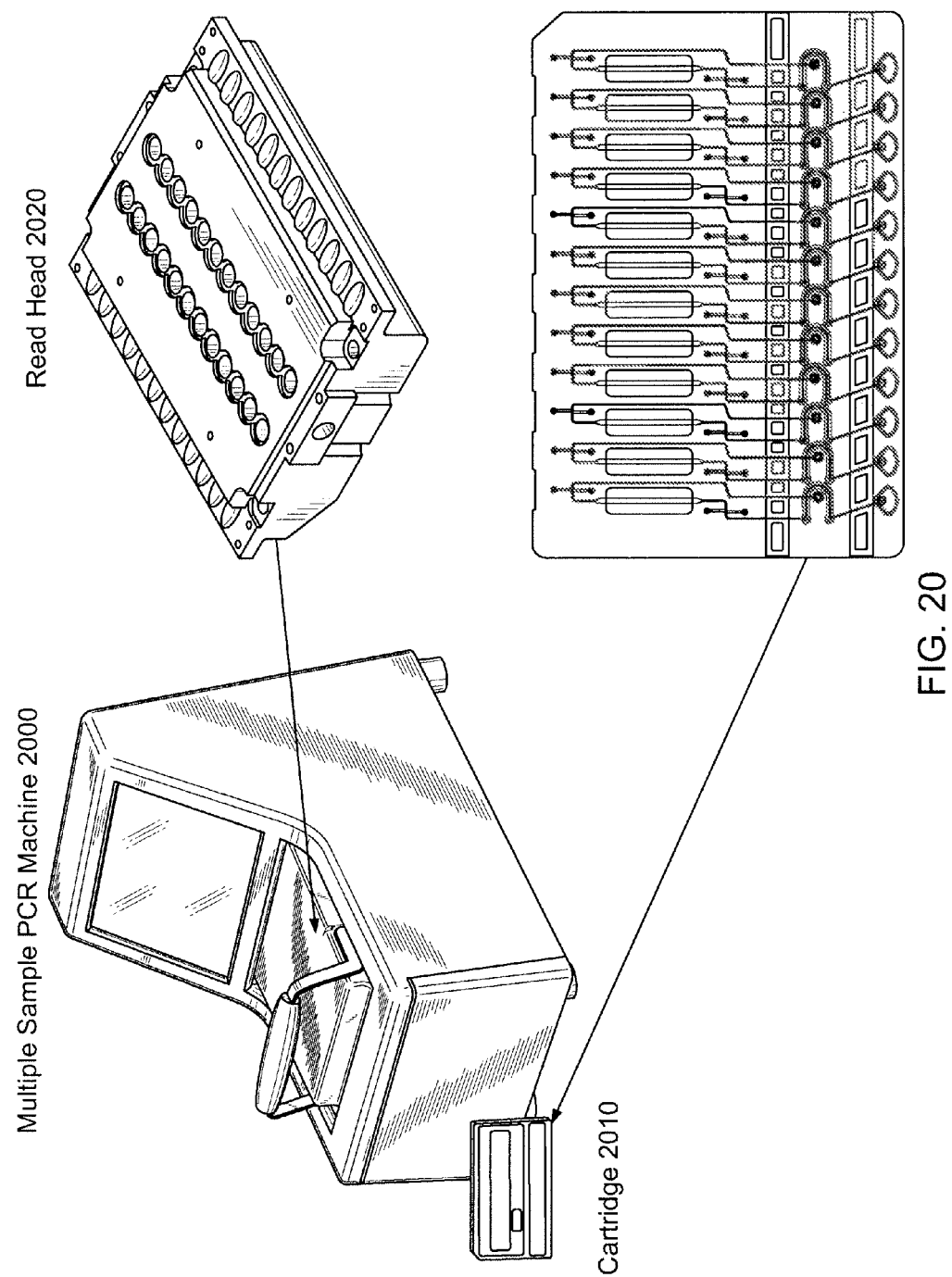
FIG. 20 shows an exemplary apparatus, a microfluidic cartridge, and a read head contains a detector, as further described herein.

FIG. 20 shows a perspective view of an exemplary apparatus 2000 consistent with those described herein, as well as various components thereof, such as exemplary cartridge 2010 that contains multiple sample lanes, and exemplary read head 2020 that contains detection apparatus for reading signals from cartridge 2010. The apparatus 2000 of FIG. 20 is able to carry out real-time PCR on a number of samples in cartridge 2010 simultaneously or serially. Preferably the number of samples is 12 samples, as illustrated with exemplary cartridge 2010, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) is prepared, as further described elsewhere (see, e.g., U.S. patent application publication 2006-0166233, incorporated herein by reference), prior to introduction into cartridge 200.

In some embodiments, an apparatus includes: a receiving bay configured to selectively receive a microfluidic cartridge as described herein; at least one heat source thermally coupled to the receiving bay; and a processor coupled to the heat source, wherein the heat source is configured to selectively heat individual regions of individual sample lanes in the cartridge, and the processor is configured to control application of heat to the individual sample lanes, separately, in all simultaneously, or in groups simultaneously; at least one detector configured to detect one or more polynucleotides or a probe thereof in a sample in one or more of the individual sample lanes, separately or simultaneously; and a processor coupled to the detector to control the detector and to receive signals from the detector.

Figure 21:
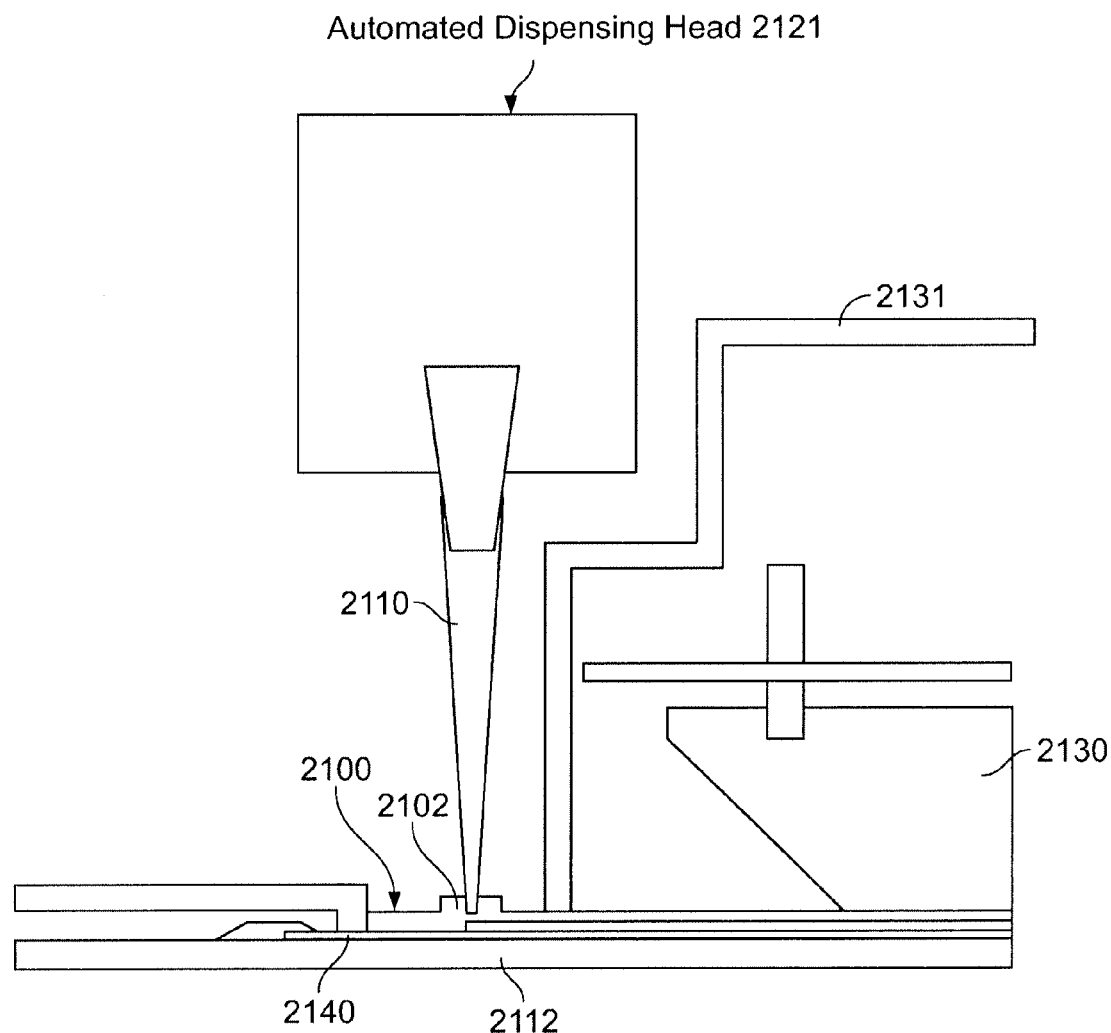
FIG. 21 shows a cross-section of a pipetting head and a cartridge in position in a microfluidic apparatus.

FIG. 21 shows a schematic cross-sectional view of a part of an apparatus as described herein, showing input of sample into a cartridge 2100 via a pipette 10 (such as a disposable pipette) and an inlet 202. Cartridge 2100 is situated in a suitably configured receiving bay 2112. Inlet 2102 is preferably configured to receive a pipette or the bottom end of a PCR tube and thereby accept sample for analysis with minimum waste, and with minimum introduction of air. Cartridge 2100 is disposed on top of and in contact with a heater substrate 2140. Read head 2130 is positioned above cartridge 2100 and a cover for optics 2131 restricts the amount of ambient light that can be detected by the read head.

Figure 22:
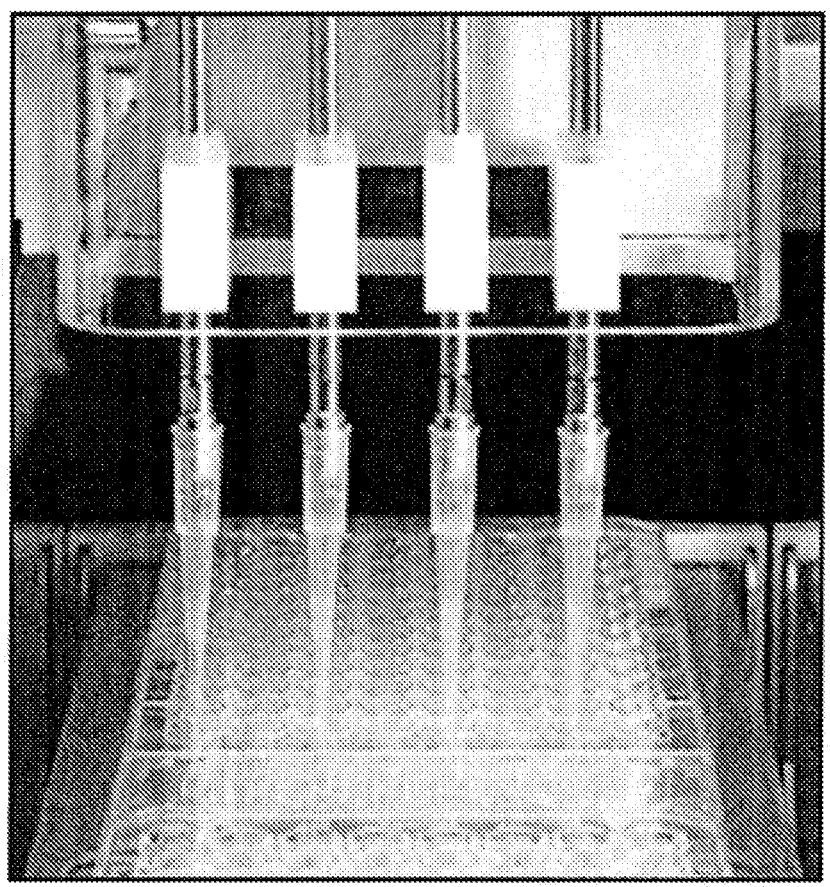
FIG. 22 shows introduction of a PCR-ready sample into a cartridge, situated in an instrument.

FIG. 22 shows an example of 4-pipette head used for attaching disposable pipette tips, prior to dispensing PCR-ready sample into a cartridge as further described herein.

The receiving bay is a portion of the apparatus that is configured to selectively receive the microfluidic cartridge. For example, the receiving bay and the microfluidic cartridge can be complementary in shape so that the microfluidic cartridge is selectively received in, e.g., a single orientation. The microfluidic cartridge can have a registration member that fits into a complementary feature of the receiving bay. The registration member can be, for example, a cut-out on an edge of the cartridge, such as a corner that is cut-off, or one or more notches or grooves that are made on one or more of the sides in a distinctive pattern that prevents a cartridge from being loaded into the bay in more than one distinct orientation. By selectively receiving the cartridge, the receiving bay can help a user to place the cartridge so that the apparatus can properly operate on the cartridge. The cartridge can be designed to be slightly smaller than the dimensions of the receiving bay, for example by approximately 200-300 microns, for easy placement and removal of the cartridge.

The receiving bay can also be configured so that various components of the apparatus that operate on the microfluidic cartridge (heat sources, detectors, force members, and the like) are positioned to properly operate thereon. For example, a contact heat source can be positioned in the receiving bay such that it can be thermally coupled to one or more distinct locations on a microfluidic cartridge that is selectively received in the bay. Microheaters in the heater module as further described elsewhere herein were aligned with corresponding heat-requiring microcomponents (such as valves, pumps, gates, reaction chambers, etc). The microheaters can be designed to be slightly bigger than the heat requiring microfluidic components so that even though the cartridge may be off-centered from the heater, the individual components can still function effectively.

As further described elsewhere herein, the lower surface of the cartridge can have a layer of mechanically compliant heat transfer laminate that can enable thermal contact between the microfluidic substrate and the microheater substrate of the heater module. A minimal pressure of 1 psi can be employed for reliable operation of the thermal valves, gates and pumps present in the microfluidic cartridge.

In various embodiments of the apparatus, the apparatus can further include a sensor coupled to the processor, the sensor configured to sense whether the microfluidic cartridge is selectively received.

The heat source can be, for example, a heat source such as a resistive heater or network of resistive heaters. In preferred embodiments, the at least one heat source can be a contact heat source selected from a resistive heater (or network thereof), a radiator, a fluidic heat exchanger and a Peltier device. The contact heat source can be configured at the receiving bay to be thermally coupled to one or more distinct locations of a microfluidic cartridge received in the receiving bay, whereby the distinct locations are selectively heated. The contact heat source typically includes a plurality of contact heat sources, each configured at the receiving bay to be independently thermally coupled to a different distinct location in a microfluidic cartridge received therein, whereby the distinct locations are independently heated. The contact heat sources can be configured to be in direct physical contact with one or more distinct locations of a microfluidic cartridge received in the bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 mm$^2$ about 225 mm (typically between about 1 mm$^2$ and about 100 mm$^2$, or in some embodiments between about 5 mm and about 50 mm$^2$). Various configurations of heat sources are further described in U.S. patent application Ser. No. 11/940,315, entitled "Heater Unit for Microfluidic Diagnostic System" and filed on even date herewith.

In various embodiments, the heat source is disposed in a heating module that is configured to be removable from the apparatus.

In various embodiments, the apparatus can include a compliant layer at the contact heat source configured to thermally couple the contact heat source with at least a portion of a microfluidic cartridge received in the receiving bay. The compliant layer can have a thickness of between about 0.05 and about 2 millimeters and a Shore hardness of between about 25 and about 100. Such a compliant layer may not be required if the instrument is able to reliably press the cartridge over the heater surface with a minimum contact pressure of say 1 psi over the entirety of the cartridge.

The detector can be, for example, an optical detector. For example, the detector can include a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample. The detector can also be configured to detect the presence or absence of sample in a PCR reaction chamber in a given sample lane, and to condition initiation of thermocycling upon affirmative detection of presence of the sample. Further description of suitably configured detectors are described in U.S. patent application Ser. No. 11/940,321, filed on Nov. 14, 2007 and entitled "Fluorescence Detector for Microfluidic Diagnostic System", incorporated herein by reference.

Although the various depictions therein show a heater substrate disposed underneath a microfluidic substrate, and a detector disposed on top of it, it would be understood that an inverted arrangement would work equally as well. In such an embodiment, the heater would be forced down onto the microfluidic substrate, making contact therewith, and the detector would be mounted underneath the substrate, disposed to collect light directed downwards towards it.

In another preferred embodiment (not shown in the FIGs. herein), a cartridge and apparatus are configured so that the read-head does not cover the sample inlets, thereby permitting loading of separate samples while other samples are undergoing PCR thermocycling.

In various embodiments, the apparatus can further include an analysis port. The analysis port can be configured to allow an external sample analyzer to analyze a sample in the microfluidic cartridge. For example, the analysis port can be a hole or window in the apparatus which can accept an optical detection probe that can analyze a sample or progress of PCR in situ in the microfluidic cartridge. In some embodiments, the analysis port can be configured to direct a sample from the microfluidic cartridge to an external sample analyzer; for example, the analysis port can include a conduit in fluid communication with the microfluidic cartridge that directs a liquid sample containing an amplified polynucleotide to a chromatography apparatus, an optical spectrometer, a mass spectrometer, or the like.

In various embodiments, the apparatus can further include one or more force members configured to apply force to at least a portion of a microfluidic cartridge received in the receiving bay. The one or more force members are configured to apply force to thermally couple the at least one heat source to at least a portion of the microfluidic cartridge. The application of force is important to ensure consistent thermal contact between the heater wafer and the PCR reactor and microvalves in the microfluidic cartridge.

The apparatus preferably also includes a processor, comprising microprocessor circuitry, in communication with, for example, the input device and a display, that accepts a user's instructions and controls analysis of samples.

In various embodiments, the apparatus can further include a lid at the receiving bay, the lid being operable to at least partially exclude ambient light from the receiving bay.

In various embodiments, the apparatus can further include at least one input device coupled to the processor, the input device being selected from the group consisting of a keyboard, a touch-sensitive surface, a microphone, and a mouse.

In various embodiments, the apparatus can further include at least one sample identifier coupled to the processor, the sample identifier being selected from an optical scanner such as an optical character reader, a bar code reader, or a radio frequency tag reader. For example, the sample identifier can be a handheld bar code reader.

In various embodiments, the apparatus can further include at least one data storage medium coupled to the processor, the medium selected from: a hard disk drive, an optical disk drive, or one or more removable storage media such as a CD-R, CD-RW, USB-drive, or flash memory card.

In various embodiments, the apparatus can further include at least one output coupled to the processor, the output being selected from a display, a printer, and a speaker, the coupling being either directly through a directly dedicated printer cable, or wirelessly, or via a network connection.

The apparatus further optionally comprises a display that communicates information to a user of the system. Such information includes but is not limited to: the current status of the system; progress of PCR thermocycling; and a warning message in case of malfunction of either system or cartridge. The display is preferably used in conjunction with an external input device as elsewhere described herein, through which a user may communicate instructions to apparatus 100. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or bar-code reader, for ensuring that a user of the system is in fact authorized to do so, according to pre-loaded identifying characteristics of authorized users. An input device may additionally—and simultaneously—function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

The apparatus may further include a computer network connection that permits extraction of data to a remote location, such as a personal computer, personal digital assistant, or network storage device such as computer server or disk farm. The network connection can be a communications interface selected from the group consisting of: a serial connection, a parallel connection, a wireless network connection, and a wired network connection such as an ethernet or cable connection, wherein the communications interface is in communication with at least the processor. The computer network connection may utilize, e.g., ethernet, firewire, or USB connectivity. The apparatus may further be configured to permit a user to e-mail results of an analysis directly to some other party, such as a healthcare provider, or a diagnostic facility, or a patient.

In various embodiments, there is an associated computer program product includes computer readable instructions thereon for operating the apparatus and for accepting instructions from a user.

In various embodiments, the computer program product can include one or more instructions to cause the system to: output an indicator of the placement of the microfluidic cartridge in the receiving bay; read a sample label or a microfluidic cartridge label; output directions for a user to input a sample identifier; output directions for a user to load a sample transfer member with the PCR-ready sample; output directions for a user to introduce the PCR-ready sample into the microfluidic cartridge; output directions for a user to place the microfluidic cartridge in the receiving bay; output directions for a user to close the lid to operate the force member; output directions for a user to pressurize the PCR-ready sample in the microfluidic cartridge by injecting the PCR-ready sample with a volume of air between about 0.5 mL and about 5 mL; and output status information for sample progress from one or more lanes of the cartridge.

In various embodiments, the computer program product can include one or more instructions to cause the system to: heat the PCR ready-sample under thermal cycling conditions suitable for creating PCR amplicons from the neutralized polynucleotide; contact the neutralized polynucleotide sample or a PCR amplicon thereof with at least one probe that is selective for a polynucleotide sequence; independently contact each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; contact the neutralized polynucleotide sample or a PCR amplicon thereof and the negative control polynucleotide or a PCR amplicon thereof with at least one probe that is selective for a polynucleotide sequence; output a determination of the presence of a polynucleotide sequence in the biological sample, the polynucleotide sequence corresponding to the probe, if the probe is detected in the neutralized polynucleotide sample or a PCR amplicon thereof; and/or output a determination of a contaminated result if the probe is detected in the negative control polynucleotide or a PCR amplicon thereof.

Apparatus 100 may optionally comprise one or more stabilizing feet that cause the body of the device to be elevated above a surface on which system 100 is disposed, thereby permitting ventilation underneath system 100, and also providing a user with an improved ability to lift system 100.

EXAMPLES

Example 1

48 Lane Cartridge

Figure 23:
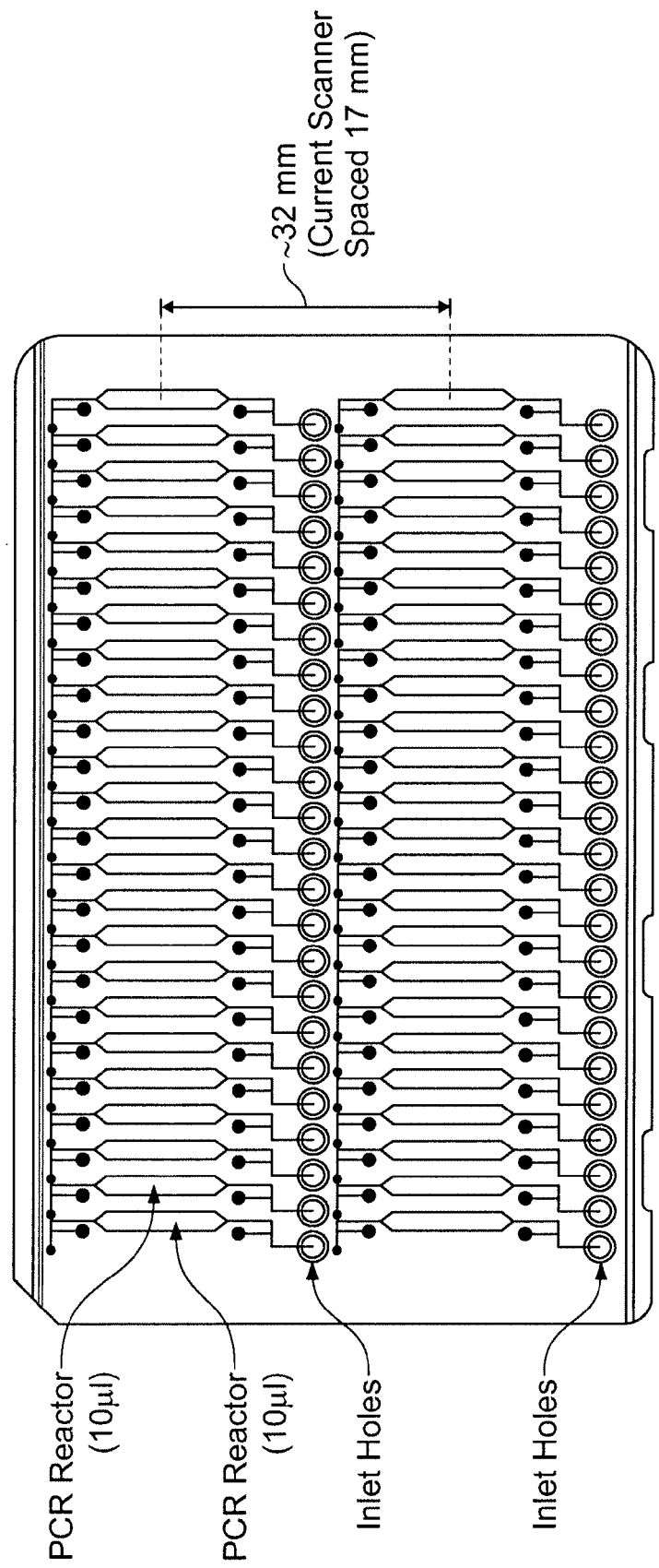
FIG. 23 shows an exemplary 48-lane cartridge.

FIG. 23 shows an exemplary 48-lane cartridge for carrying out PCR independently on 48 samples, and with a reaction volume of 10 microliter each. The area occupied by the entire cartridge is approximately 3.5 inches (8.9 cm) by 4.25 inches (10.8 cm). The sample lanes are organized as two groups of 24 each. The adjacent sample lanes in each of the two rows of 24 are spaced apart 4 mm (center-to-center). Trenches between the PCR lanes may be cut in order to isolate the heating of each PCR channel from those adjacent to it. This may be accomplished by etching, milling, controlled cutting, etc., during fabrication of the cartridge.

Figure 24:
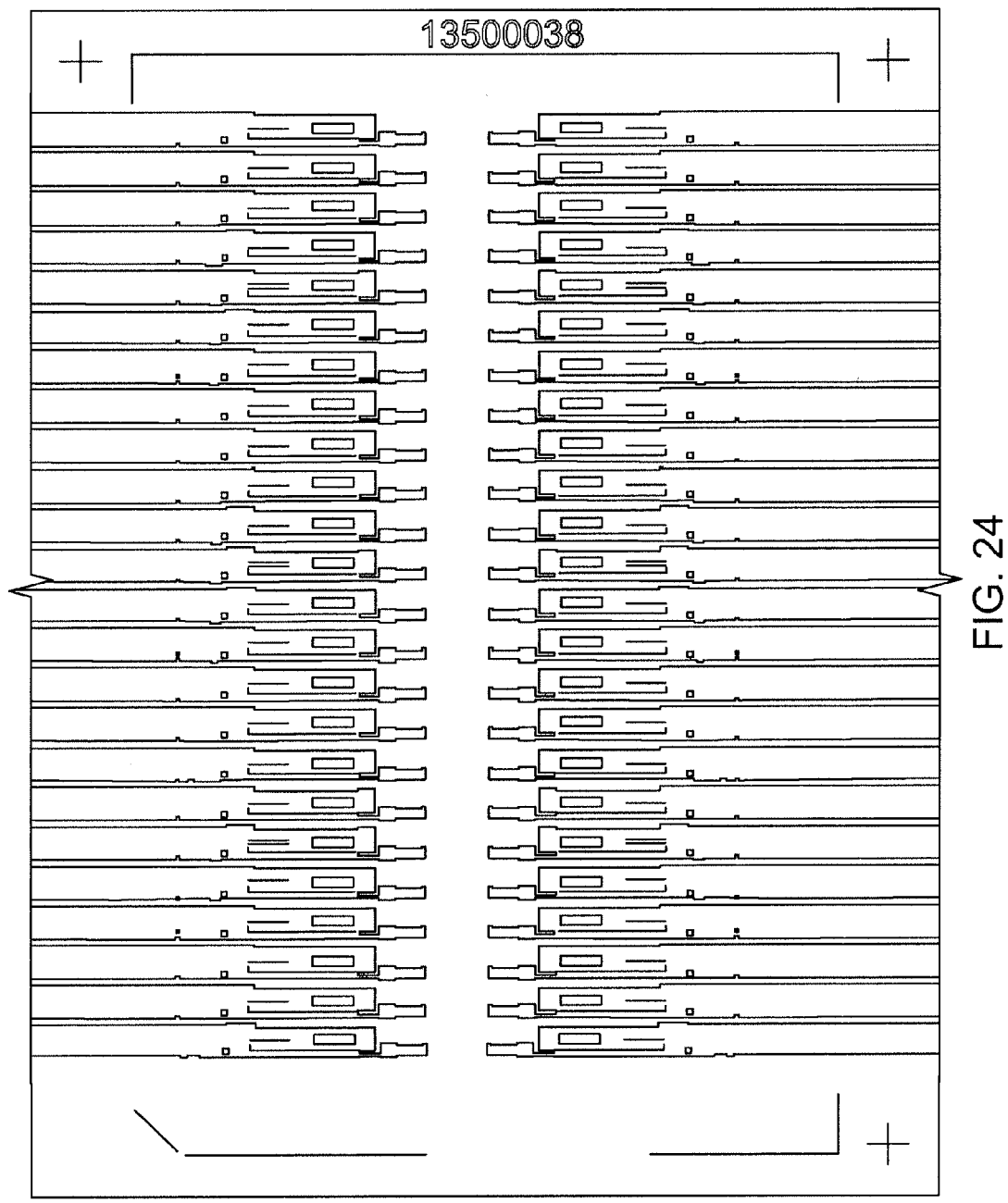
FIG. 24 shows a heater configuration used for actuating the 48-lane PCR cartridge of FIG. 23.

FIG. 24 shows a heater design used for actuating the 48 lane PCR cartridge of FIG. 23. The heating of each sample lane can be independently controlled.

Example 2

PCR Cartridge with Post-PCR Retrieval Capability

Figure 25A:
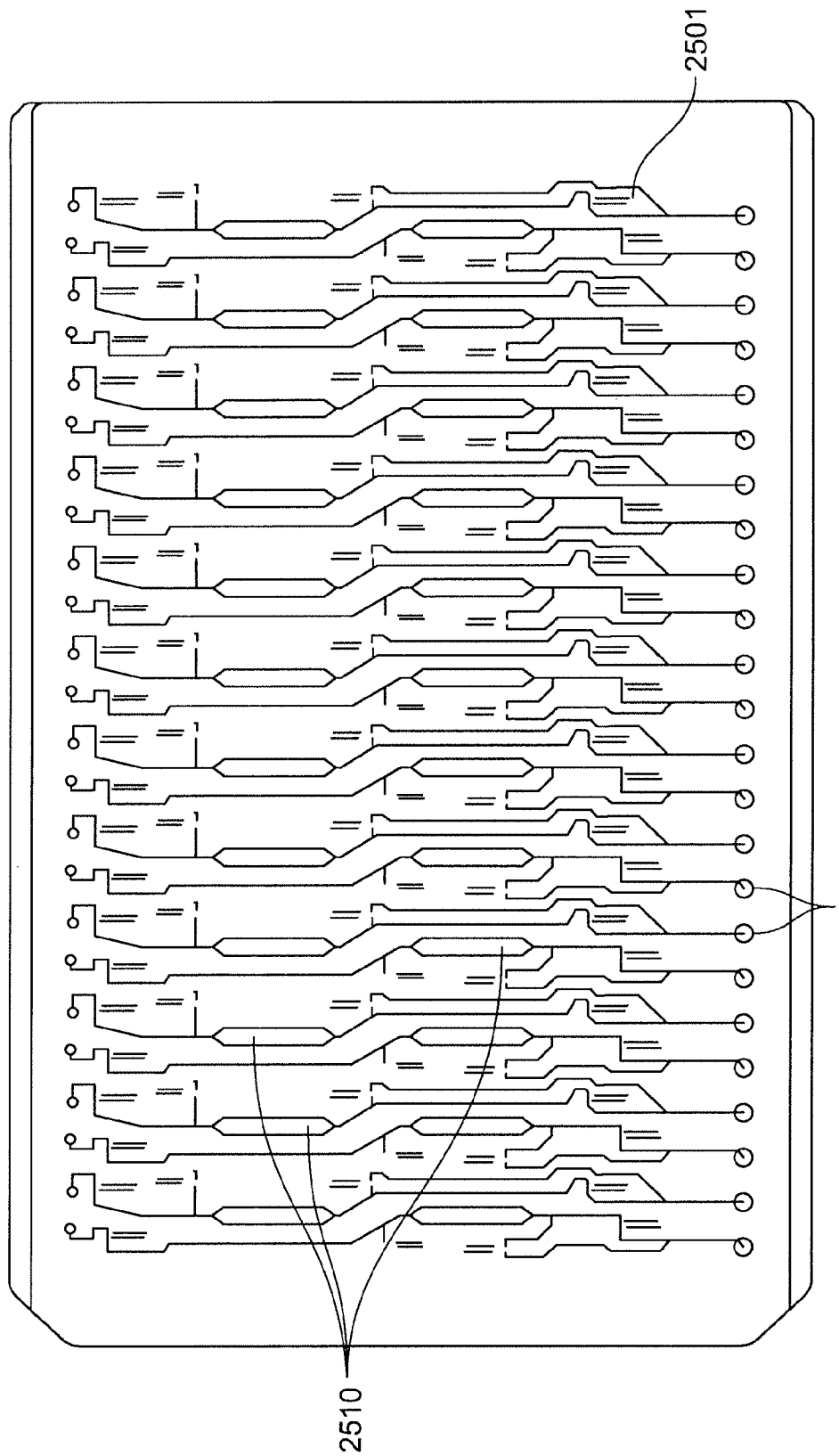
FIGS. 25A and 25B respectively show an exemplary cartridge and lane configuration for a cartridge that permits retrieval of amplified sample.
Figure 25B:
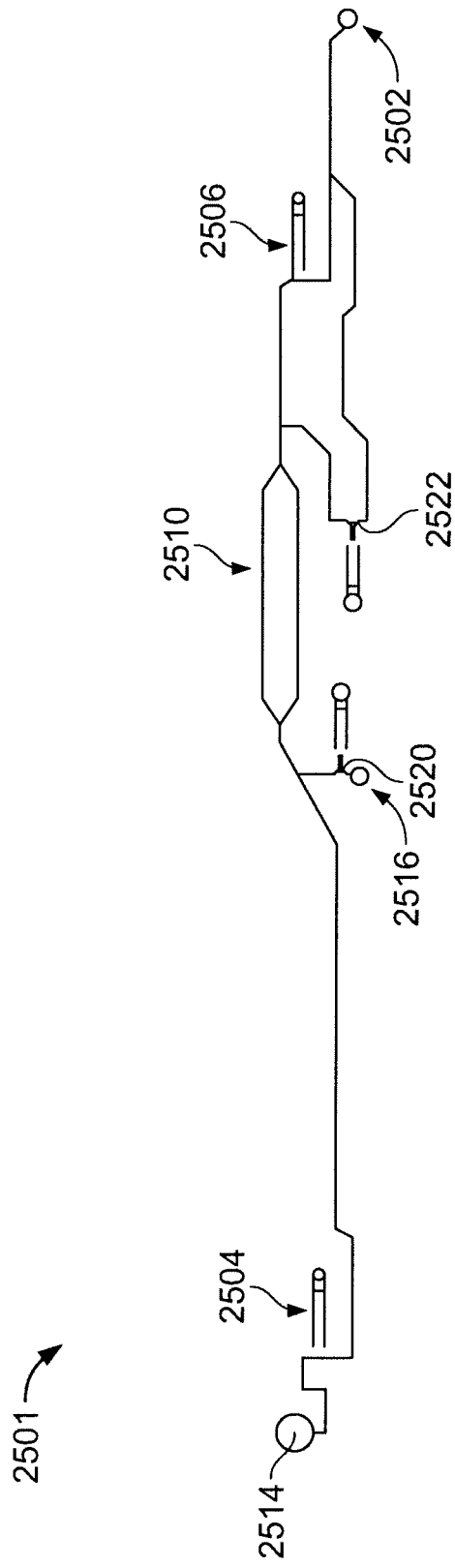

Many applications such as genotyping, sequencing, multiple analyte detection (microarray, electrochemical sensing) require post-PCR sample retrieval and subsequent analysis of the retrieved sample in a different instrument. The cartridge of this example, of which a 24 lane embodiment is shown in FIG. 25A, with a sample lane layout illustrated in FIG. 25B, accommodates such a retrieval capability. Each lane in the cartridge of FIG. 25A independently permits sample retrieval. The configuration of the lane of FIG. 25B is different from that of, e.g., FIG. 6 at least because of the presence of 2 gates and the alternative channel from the reactor, via Gate 1, to the inlet. Such features permit effective sample retrieval.

Sample DNA mixed with PCR enzymes is input into a sample lane 2501 through the inlet hole 2502 in the microfluidic network described below. The valves 2506, 2504 (valves 1 and 2) are initially open while the gates 2522, 2520 (gates 1 and 2) are closed, enabling the reaction mix to fill up the PCR reactor 2510 with the excess air venting out through vent hole 1 (label 2514). The valves 1 and 2 are then closed to seal off the reaction mixture. Thermocycling is initiated to conduct the PCR reaction within the PCR reactor. After the reaction is completed, a pipette is mechanically interfaced with the inlet hole 2502 and suction force applied to the pipette. Gates 1 and 2 are opened to enable the reacted sample to exit the PCR reactor and enter the pipette. This controlled opening of the PCR device will also prevent post-PCR contamination of the apparatus in which the cartridge resides as there is minimal exposure of the PCR product with the atmosphere.

It will be understood that reactions other than PCR can easily be performed in the cartridge of this example.

Example 3

12-Lane Cartridge

The 12 channel cartridge of this example is the same basic design that is described and shown in FIG. 3, with the following modifications: the volume of the PCR reactor is increased from 2 μl to 4.5 μl, leading to an increase in the acceptable input volume from 4 μl to 6 μl. Increasing the reaction volume facilitates detection from even dilute samples (wherein the target DNA concentration may be low). In order to detect DNA in a reactor of say 1 microliter volume, there should be a minimum of 1-2 copies of the DNA in the 1 microliter for positive identification, i.e., the concentration should not be less than around 1-2 copies/microliter. Increasing the reaction volume to say 5 microliters will reduce the minimum acceptable starting DNA concentration by 5 fold. The inlet holes are moved a few millimeters away from the edge of the cartridge to allow room for a 2 mm alignment ledge in the cartridge. A similar alignment ledge is also included on the other edge of the cartridge. The alignment ledge permits the cartridges to be stacked during storage (or within a multi-cartridge spring-loader) without the hydrophobic vent of one cartridge coming into contact with a surface of an adjacent cartridge.

Example 4

24-Lane Cartridge

This 24-lane cartridge has two rows of 12 sample lanes. Each lane has: a liquid inlet port, that interfaces with a disposable pipette; a 4 microliter PCR reaction chamber (1.5 mm wide, 300 microns deep and approximately 10 mm long), and two microvalves on either side of the PCR reactor and outlet vent. Microvalves are normally open, and close the channel on actuation. The outlet holes enable extra liquid (~1 μl) to be contained in the fluidic channel in case more than 6 μl of fluid is dispensed into the cartridge. Thus, the cartridge of this example does not require a bubble vent as it will be used in an automated PCR machine having a reliable, precision liquid dispenser.

The inlet holes of the cartridge of this example are made conical in shape and have a diameter of 3-6 mm at the top to ensure that pipette tips can be easily landed by an automated fluid dispensing head into the conical hole, with some tolerance. There is also an optional raised annulus around the top of the holes. Once the pipette tip lands within the cone, the conical shape guides the pipette and mechanically seals to provide error free dispensing into, or withdrawal of fluid from, the cartridge. The bigger the holes, the better it is to align with the pipette, however, given the opposing need to maximize the number of inlet ports within the width of the cartridge as well as to maintain the pitch between holes compatible with the inter-pipette distance, the holes cannot be too big. In this design, the inter-pipette tip distance is 18 mm and the distance between the loading holes in the cartridge is 6 mm. So lanes 1, 4, 7, 11 are pipetted into during one dispensing operation that utilizes four pipette tips; lanes 2, 5, 8 and 12 in the next, and so on and so forth.

The height of the conical holes is kept lower than the height of the ledges on the edges of the cartridge to ensure the cartridges can be stacked on the ledges. The ledges on the two long edges of the cartridge enable stacking of the cartridges with minimal surface contact between two stacked cartridges and also help guide the cartridge into the reader from a spring-loader, where used.

Example 5

12-Lane Cartridge

This 12-lane cartridge has 12 sample lanes in parallel, as shown in FIG. 1. Each lane has: a liquid inlet port that interfaces with a disposable pipette; a bubble vent; a PCR reaction chamber, and two microvalves on either side of the PCR reactor and outlet vent. Microvalves are normally open, and close the channel on actuation. The reaction volume is in the range 1-10 μl so that the number of copies of DNA will be sufficient for detection. Such a volume also permits the PCR reaction volume to be similar to release volume from a sample preparation procedure.

Example 6

Kit

Figure 26A:
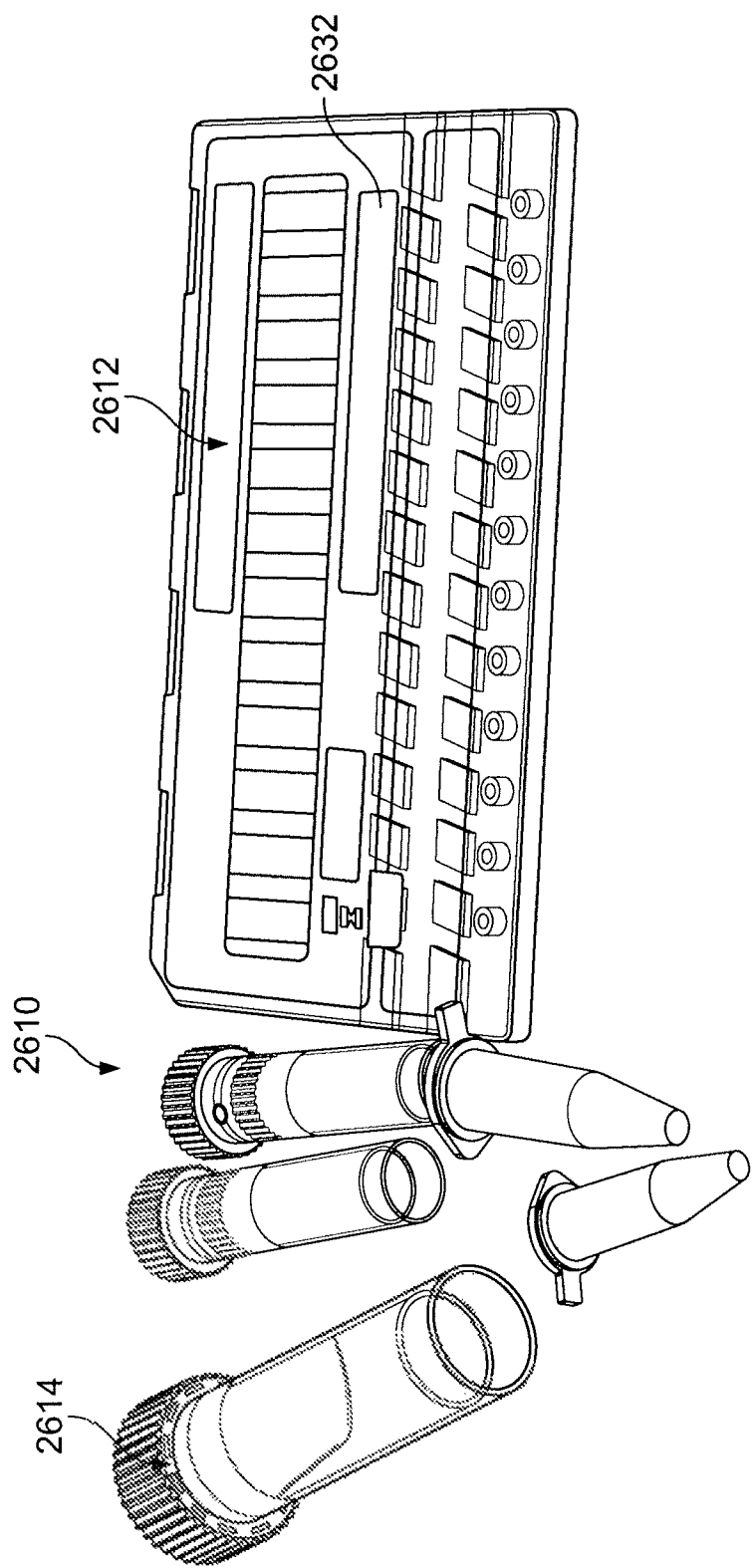
FIG. 26A shows components of a kit, including an exemplary cartridge and reagents.
Figure 26B:
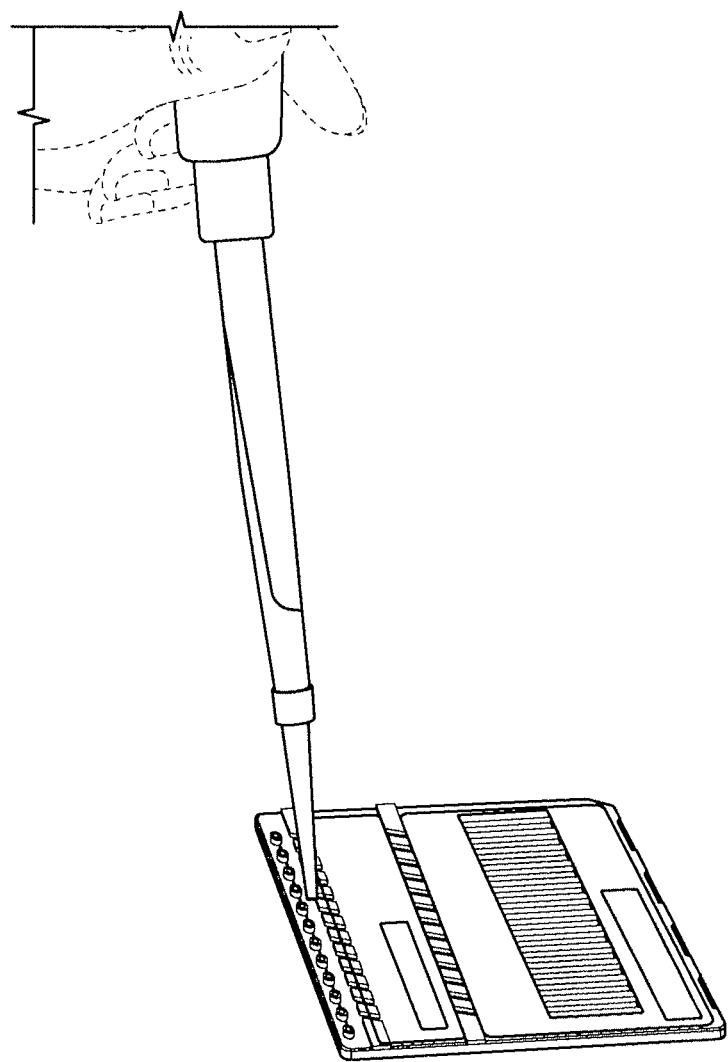
FIG. 26B shows manual action of pipetting a PCR solution into PCR lanes of the cartridge.

FIG. 26 shows a representative sample kit 2610 that includes a microfluidic cartridge 2612 with a barcode label 2632, and one or more sample containers 2614 each also optionally having a barcode label.

Figure 27:
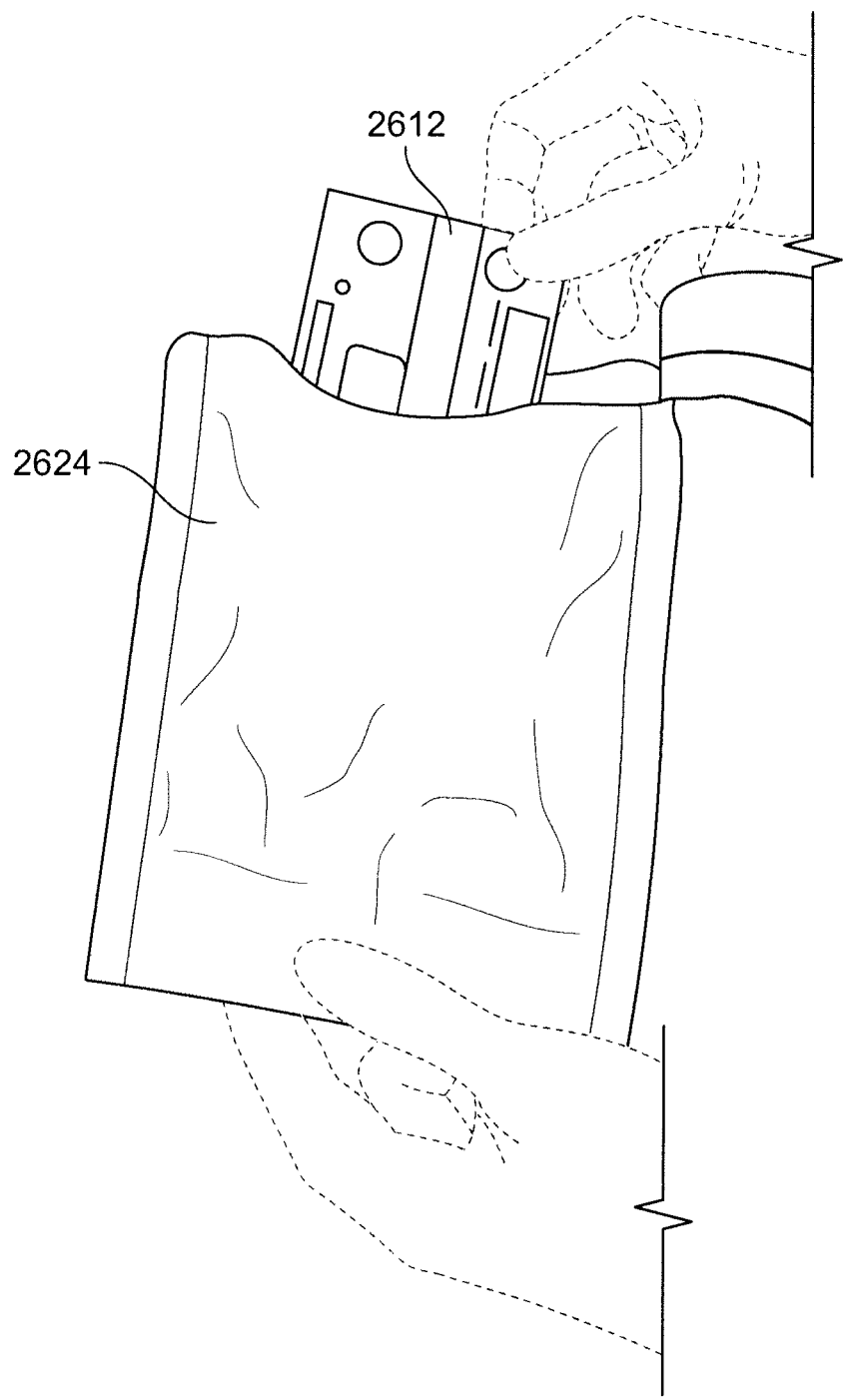
FIG. 27 shows an exemplary cartridge partially removed from a sealed pouch.

FIG. 27 shows that one or more components of the sample kit, for example, microfluidic cartridge 2612, can be packaged in a sealed pouch 2624. The pouch can be hermetically sealed with an inert gas such as argon, nitrogen, or others.

The barcode labels of both cartridge and sample container can be read with a bar code reader prior to use.

Example 7

Apparatus and Process for Wax Loading of Valves

Exemplary Wax-Deposition Process

Figure 28A:
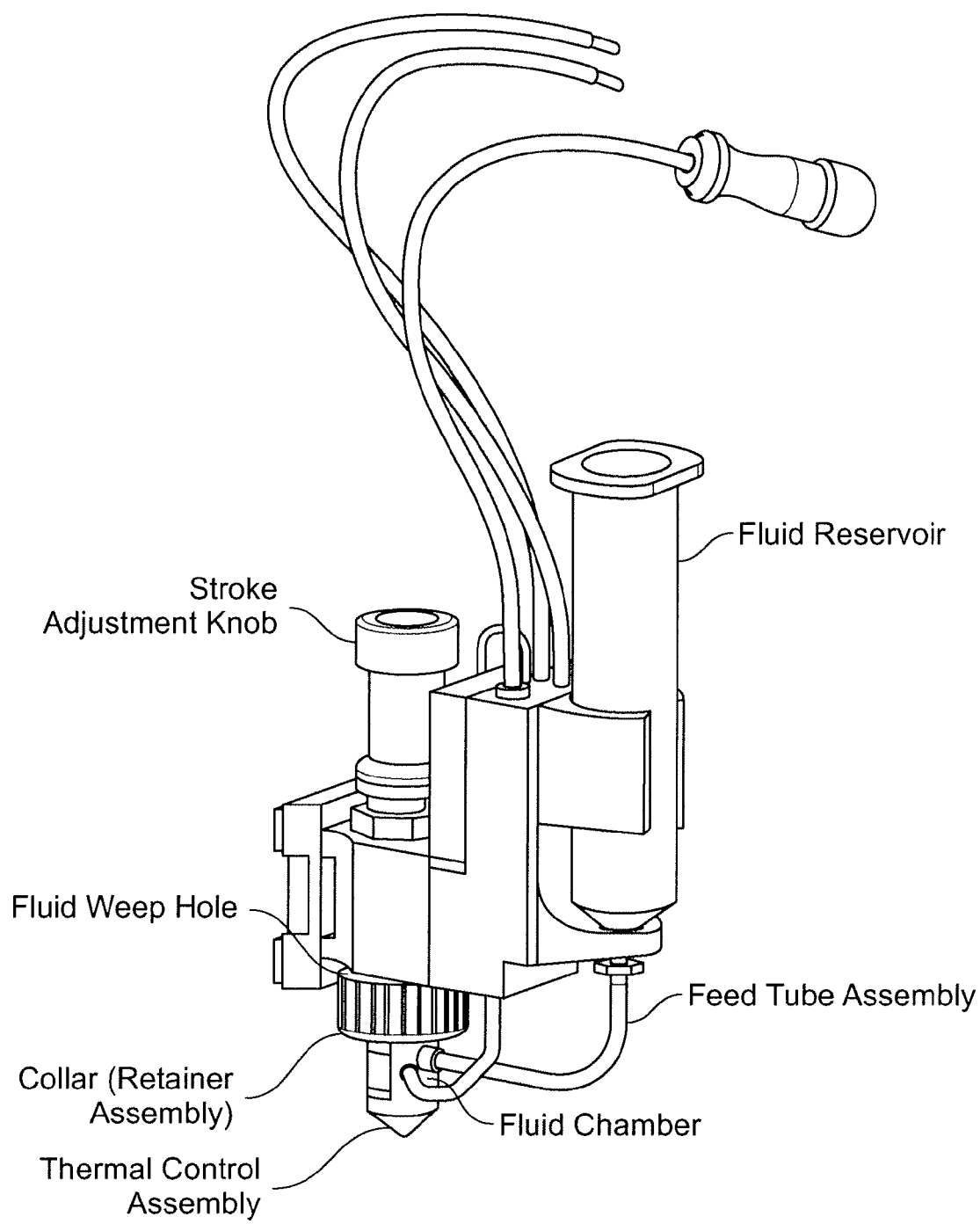
FIGS. 28A and 28B show exemplary apparatus for carrying out wax deposition.
Figure 28B:
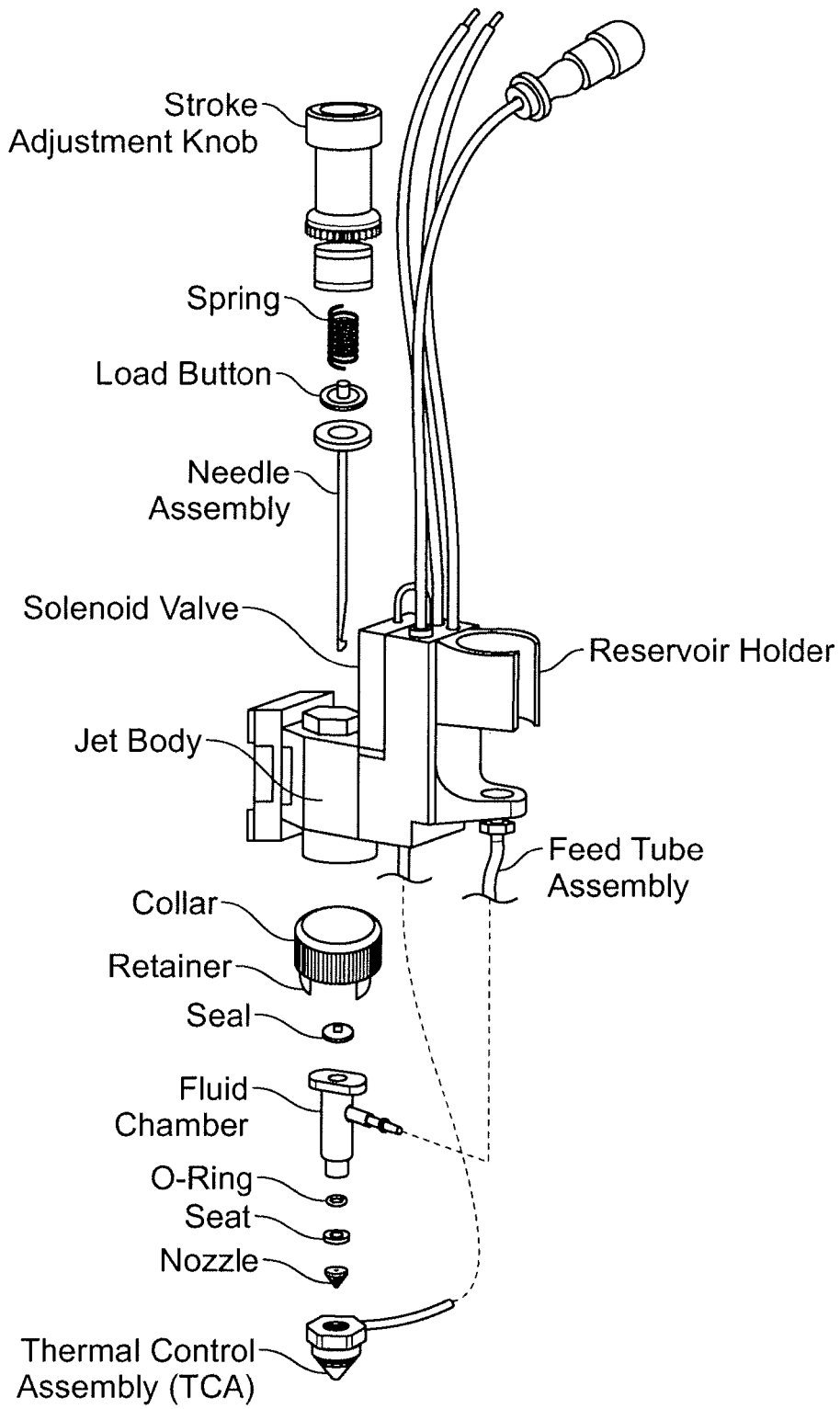

Deposition of wax in valves of the microfluidic network, as at step 1804 of FIG. 18 may be carried out with the exemplary equipment shown in FIGS. 28A and 28B. The DispenseJet Series DJ-9000 (available from Asymtek, Carlsbad, Calif.) is a non-contact dispenser suitable for this purpose that provides rapid delivery and high-precision volumetric control for various fluids, including surface mount adhesive, underfill, encapsulants, conformal coating, UV adhesives, and silver epoxy. The DJ-9000 jets in tight spaces as small as 200 micrometers and creates fillet wet-out widths as small as 300 micrometers on the dispensed side of a substrate such as a die. It dispenses fluid either as discrete dots or a rapid succession of dots to form a 100-micron (4 mil) diameter stream of fluid from the nozzle. It is fully compatible with other commercially available dispensing systems such as the Asymtek Century C-718/C-720, Millennium M-2000, and Axiom X-1000 Series Dispensing Systems.

A DJ-9000 is manufactured under quality control standards that aim to provide precise and reliable performance. Representative specifications of the apparatus are as follows.

| Characteristic | Specification |
|---|---|
| Size | Width: 35 mm<br>Height: 110 mm<br>Depth: 100 mm |

-continued

| Characteristic | Specification |
| --- | --- |
| Weight | 400 grams - dry |
| Feed Tube Assembly | Nylon -Fitting<br>Polyurethane - Tube |
| Fluid Chamber | Type 303 Stainless Steel |
| Seat and Nozzle | 300/400 Series S/S, Carbide |
| Needle Assembly | 52100 Bearing Steel - Shaft<br>Hard Chrome Plate<br>Carbide - Tip |
| Fluid Seal | PEEK/Stainless Steel |
| Fluid Chamber 0-Ring | Ethylene Propylene |
| Jet Body | 6061-T6 Aluminum<br>Nickel Plated |
| Needle Assembly Bearings | PEEK |
| Thermal Control Body | 6061-T6 Aluminum<br>Nickel Plated |
| Reservoir Holder | Acetyl |
| Reservoir Size | 5, 10, or 30 cc (0.17, 0.34,<br>or 1.0 oz) |
| Feed Tube Assembly Fitting | Female Luer per ANSI/HIMA<br>MD70.1-1983 |
| Maximum Cycle Frequency | 200 Hz. |
| Minimum Valve Air Pressure | 5.5 bar (80 psi) |
| Operating Noise Level | 70 db* |
| Solenoid | 24 VDC, 12.7 Watts |
| Thermal Control Heater | 24 VDC, 14.7 Watts, 40 ohms |
| Thermal Control RTD | 100 ohm, platinum |
| Maximum Heater Set Point | 80° C. |

*At Maximum Cycle Rate

An exploded view of this apparatus is shown in FIG. 28B.

Theory of Operation of DJ-9000

The DJ-9000 has a normally closed, air-actuated, spring-return mechanism, which uses momentum transfer principles to expel precise volumes of material. Pressurized air is regulated by a high-speed solenoid to retract a needle assembly from the seat. Fluid, fed into the fluid chamber, flows over the seat. When the air is exhausted, the needle travels rapidly to the closed position, displacing fluid through the seat and nozzle in the form of a droplet. Multiple droplets fired in succession can be used to form larger dispense volumes and lines when combined with the motion of a dispenser robot.

The equipment has various adjustable features: The following features affect performance of the DJ-9000 and are typically adjusted to fit specific process conditions.

Fluid Pressure should be set so that fluid fills to the seat, but should not be influential in pushing the fluid through the seat and nozzle. In general, higher fluid pressure results in a larger volume of material jetted.

The Stroke Adjustment controls the travel distance of the Needle Assembly. The control is turned counterclockwise to increase needle assembly travel, or turned clockwise to decrease travel. An increase of travel distance will often result in a larger volume of material jetted.

The Solenoid Valve controls the valve operation. When energized, it allows air in the jet air chamber to compress a spring and thereby raise the Needle Assembly. When de-energized, the air is released and the spring forces the piston down so that the needle tip contacts the seat.

The seat and nozzle geometry are typically the main factors controlling dispensed material volume. The seat and nozzle size are determined based on the application and fluid properties. Other parameters are adjusted in accordance with seat and nozzle choices. Available seat and nozzle sizes are listed in the table hereinbelow.

Thermal Control Assembly: Fluid temperature often influences fluid viscosity and flow characteristics. The DJ-9000 is equipped with a Thermal Control Assembly that assures a constant fluid temperature.

Dot and Line Parameters: In addition to the DJ-9000 hardware configuration and settings, Dot and Line Parameters are set in a software program (referred to as FmNT) to control the size and quality of dots and lines dispensed.

Example 7

24-Lane Cartridge

Figure 29A:
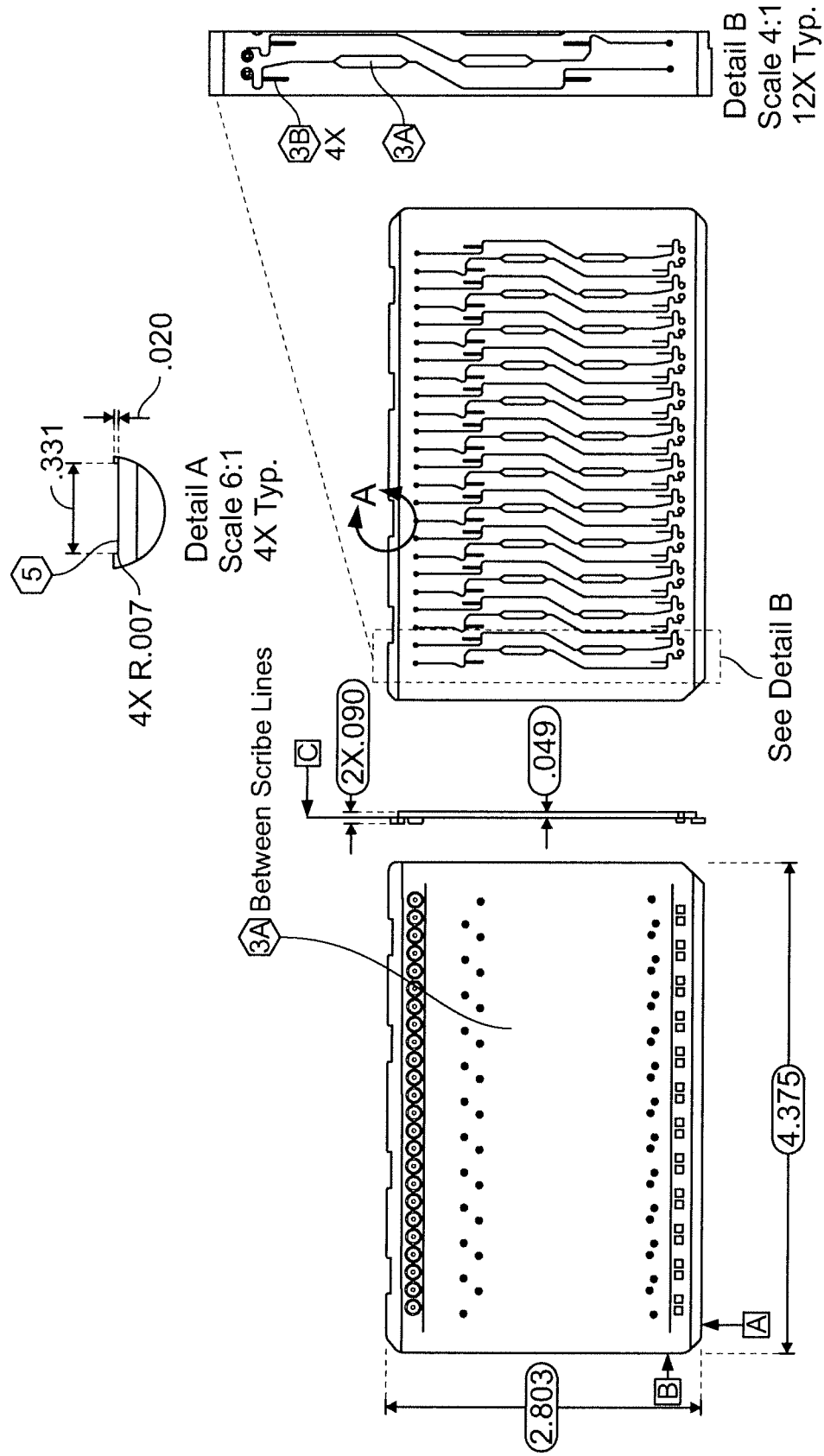
FIGS. 29A-29C show an exemplary 24-lane cartridge in plan view, perspective views, and cross-section, respectively.
Figure 29B:
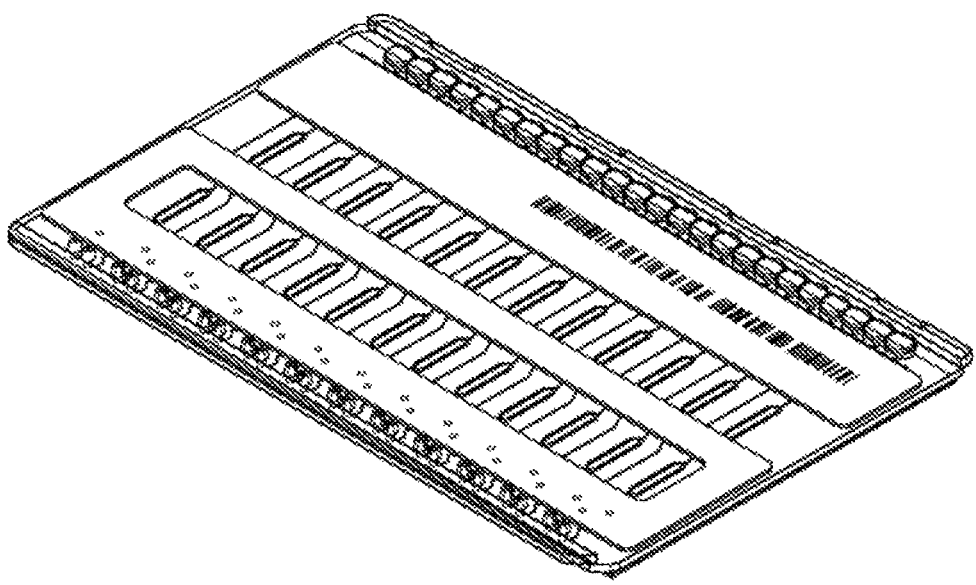
Figure 29C:
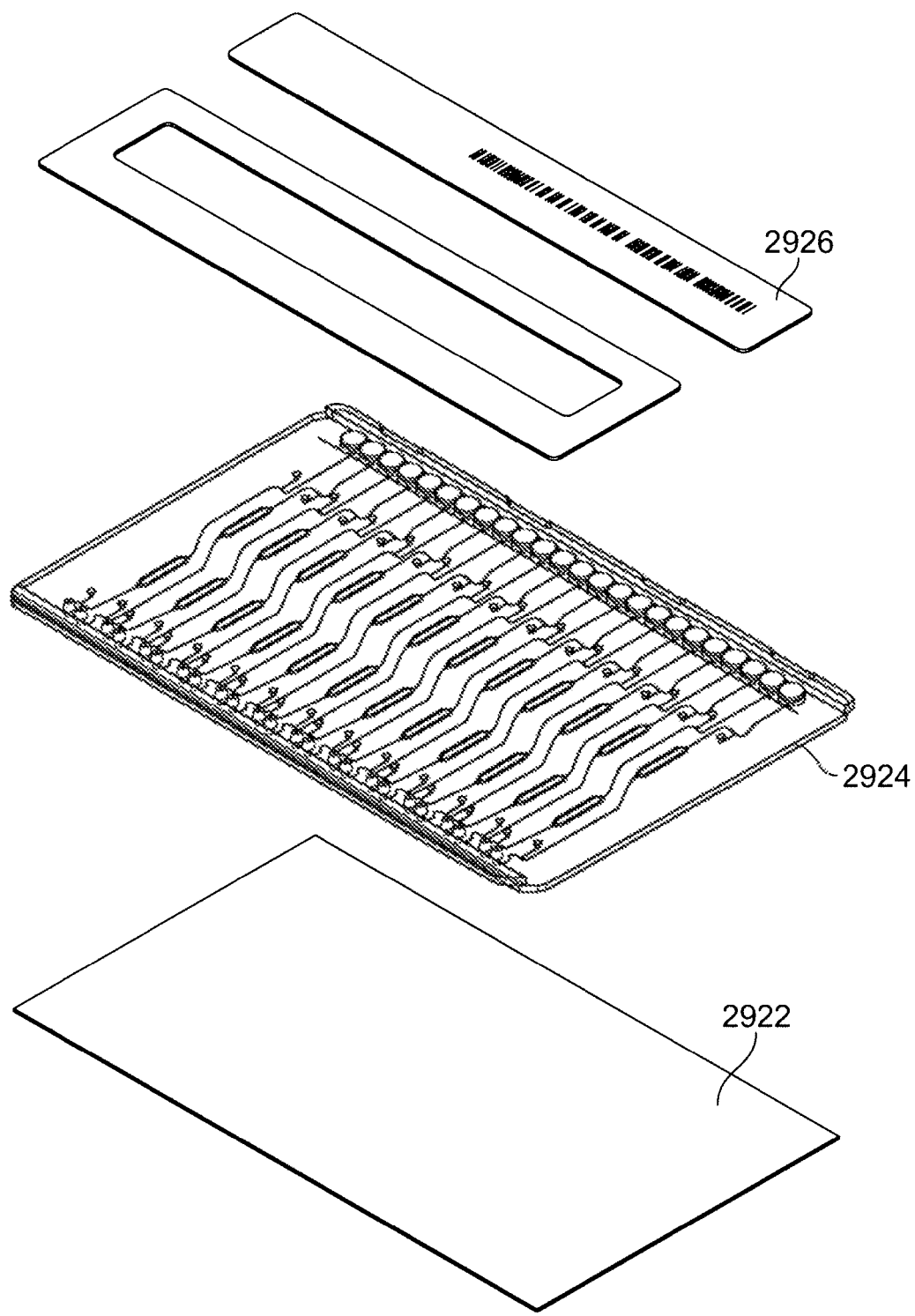

FIGS. 29A-29C show an exemplary 24-lane cartridge having three layers in its construction in which there is no hydrophobic membrane, and no thermally compliant layer. The three layers are a laminate 2922, a microfluidic substrate 2924, and a label 2926. A typical reaction vol. is 4.5 µl in each lane from 2 rows of 12 lanes. No bubble-removal vents are utilized and instead of a hydrophobic end vent, there is just a hole. This is consistent with use of an accurate pipetting system. There is no thermally compliant/conductive layer for situations where enough pressure can be reliably applied to the cartridge that effective thermal contact with the microfluidic substrate can be made without requiring the additional layer. The absence of two layers from the construction saves manufacturing costs.

Example 8

96-Lane Cartridge

Figure 30A:
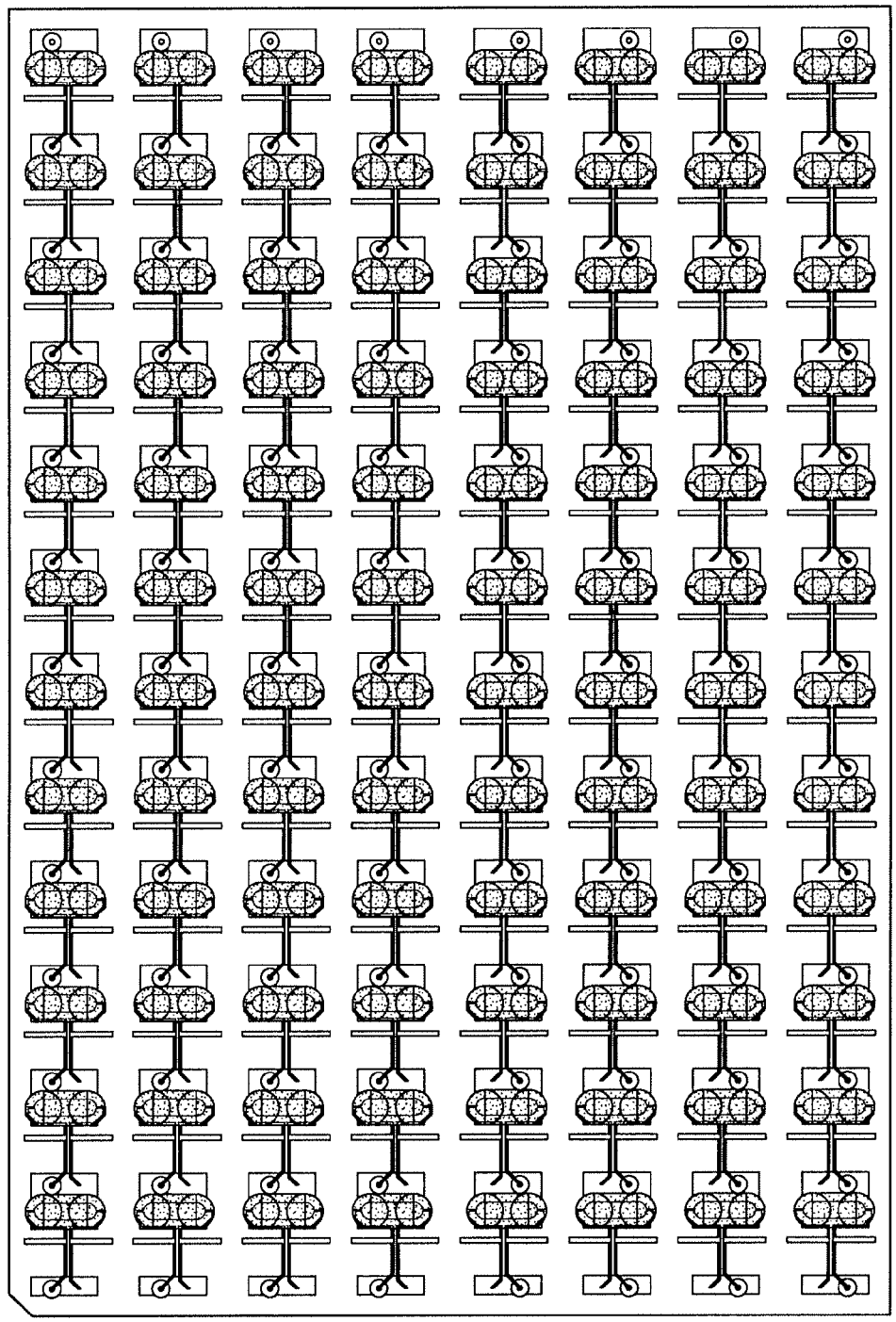
FIGS. 30A-30D show aspects of a 96-lane cartridge.
Figure 30B:
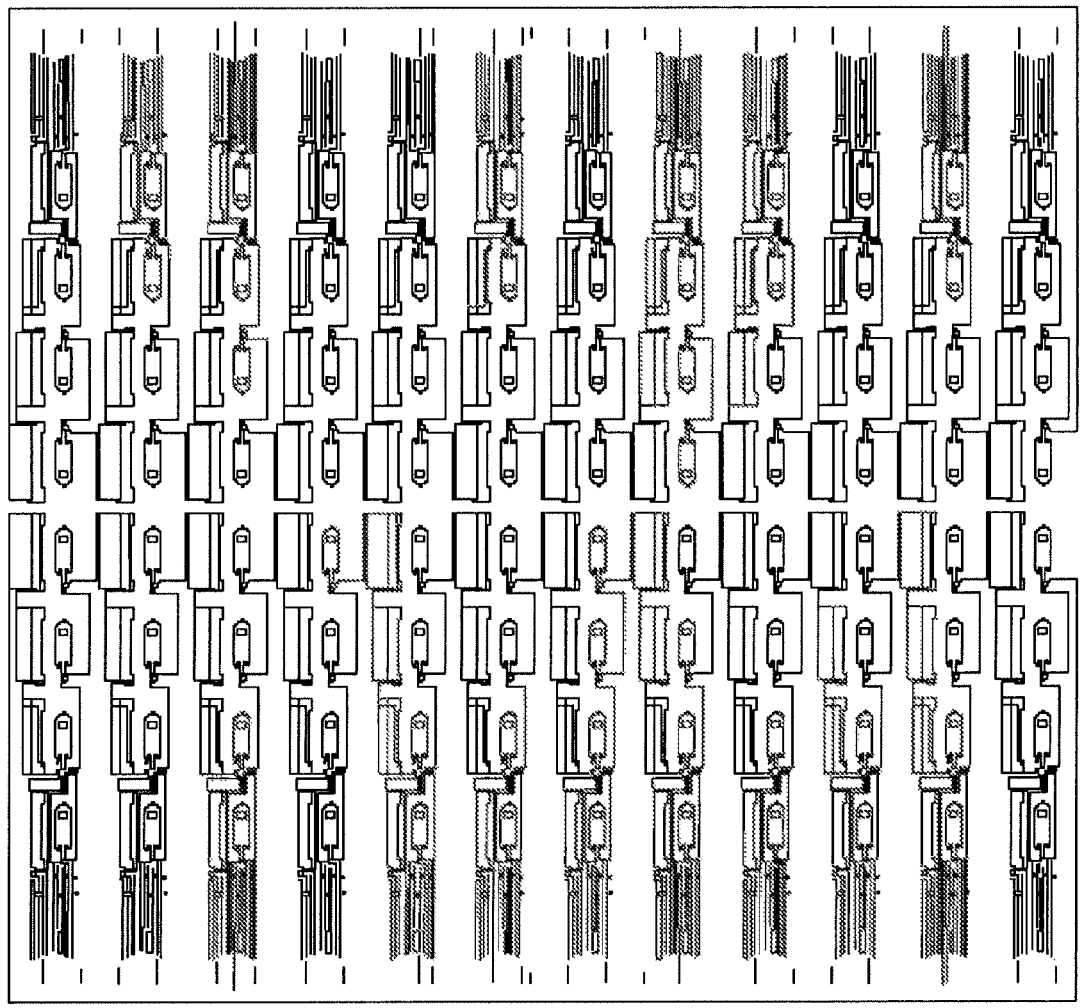
Figure 30C:
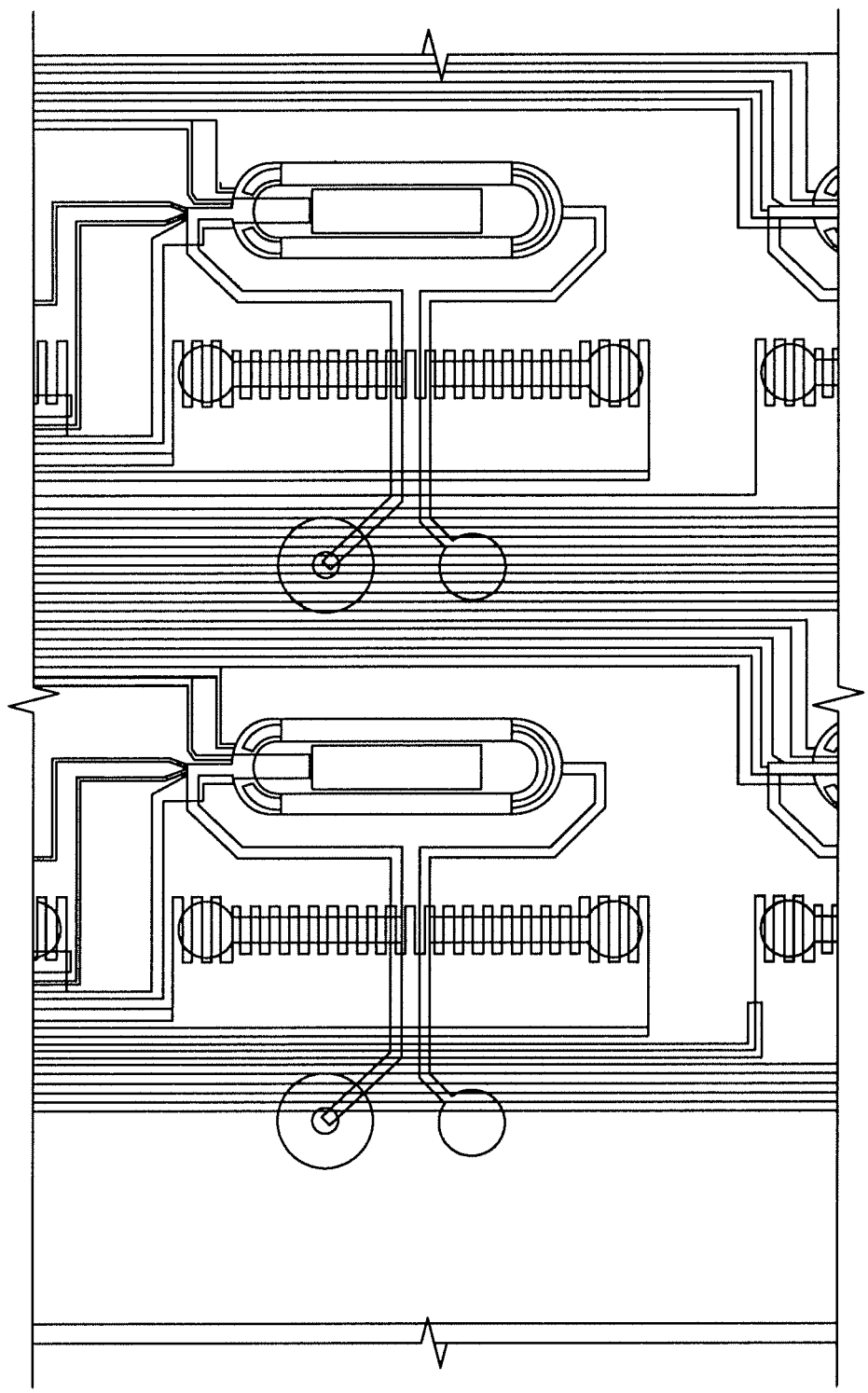
Figure 30D:
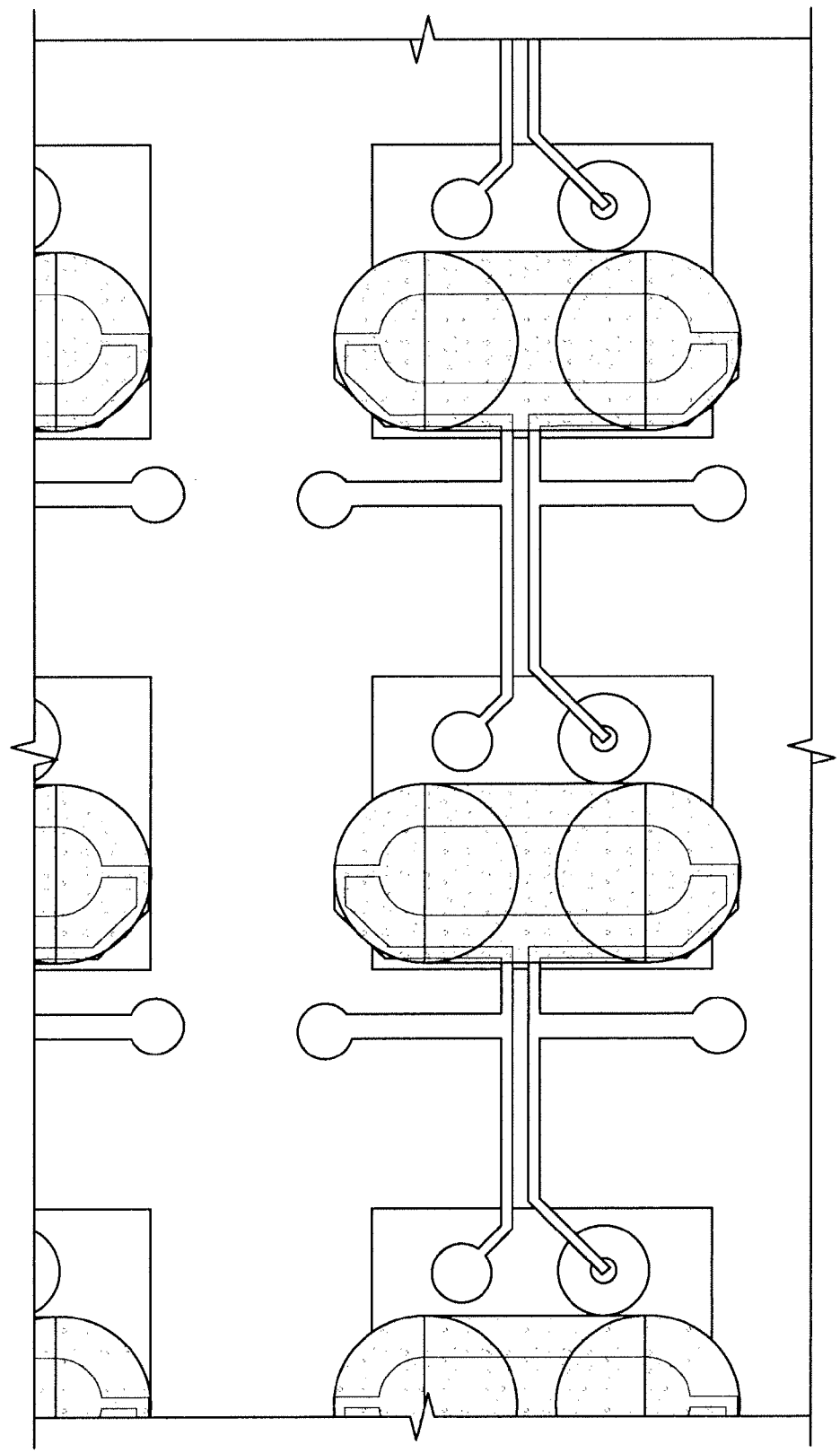

FIGS. 30A-D show aspects of a 96-lane cartridge design, including complementary heater configurations. (FIG. 30A shows cartridge design; 30B shows heater design in a single metal layer; 30C shows individual PCR channels overlaid with heater configurations; 30D shows individual PCR lanes.) In the embodiment shown, liquid sample is loaded without air bubbles as the lanes do not have any vents. Two or more Mux can be utilized for controlling all 96 PCR channels.

Such an arrangement lends itself to whole area imaging (e.g., by a CCD) for detection instead of optical based methods using diodes and lenses.

Example 9

Real-Time PCR

Figure 31:
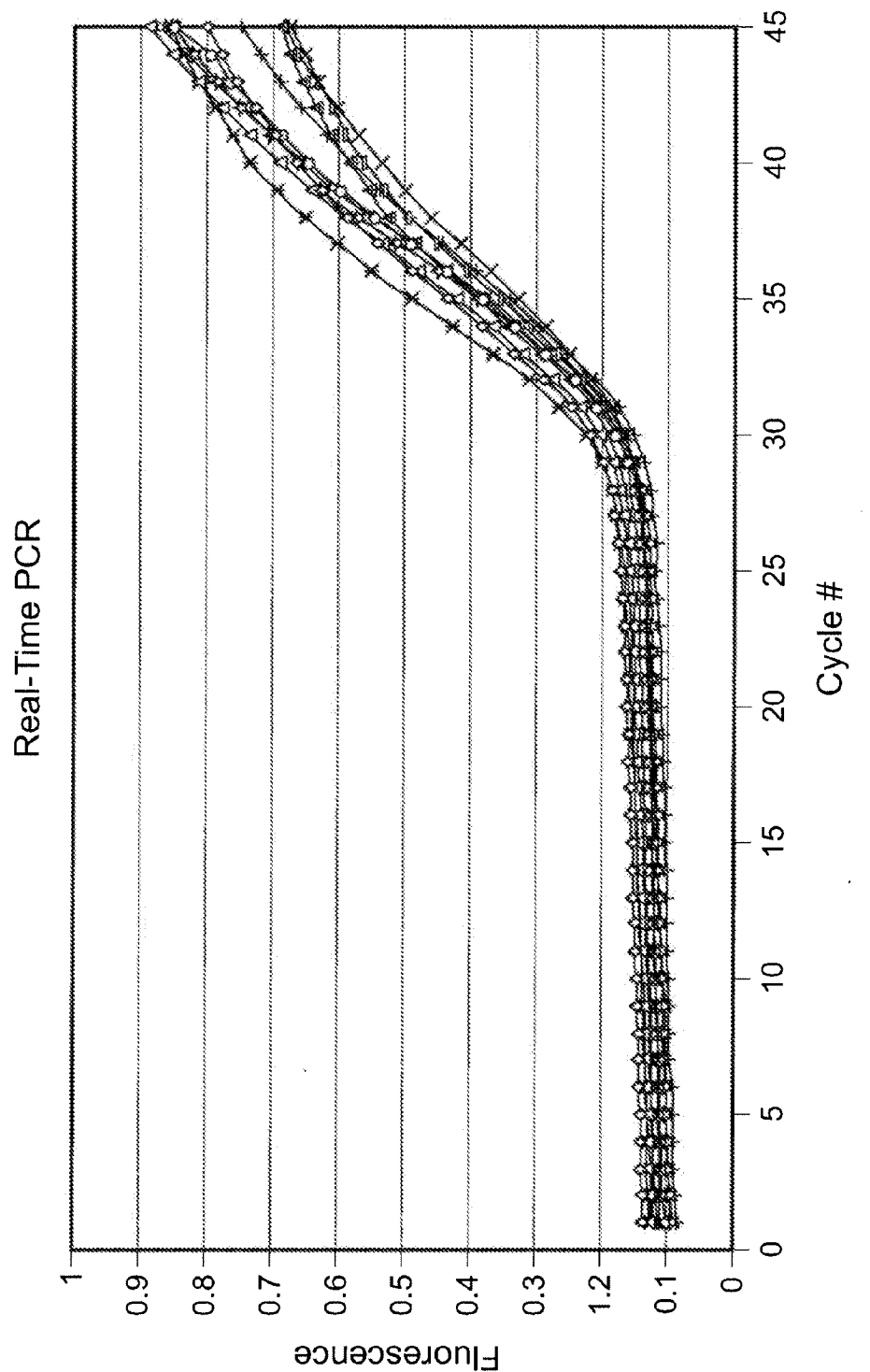
FIG. 31 shows a real-time PCR trace.

FIG. 31 shows a trace of real-time PCR carried out on multiple samples in parallel with an apparatus and microfluidic network as described herein. The PCR curves are standard plots that are representative of fluorescence from 12 different PCR lanes as a function of cycle number.

The foregoing description is intended to illustrate various aspects of the present technology. It is not intended that the examples presented herein limit the scope of the present technology. The technology now being fully described, it will be apparent to one of ordinary skill in the art that many changes and modifications can be made thereto without departing from the spirit or scope of the appended claims.

What is claimed:

1. A microfluidic cartridge comprising a microfluidic substrate layer, the microfluidic substrate layer comprising:
    a first reaction chamber;
    a second reaction chamber;
    a first inlet port for introducing a first sample onto the microfluidic substrate layer, the first inlet port formed in a surface of the microfluidic substrate layer and in fluid communication with the first reaction chamber;
    a second inlet port for introducing a second sample onto the microfluidic substrate layer, the second inlet port spaced apart from the first inlet port on the surface of the microfluidic substrate layer, the second inlet port in fluid communication with the second reaction chamber;
a first outlet, in fluid communication with the first reaction chamber;
a second outlet, in fluid communication with the second reaction chamber;
a first set of microfluidic valves configured to isolate the first reaction chamber from the first inlet port and the first outlet; and
a second set of microfluidic valves configured to isolate the second reaction chamber from the second inlet port and the second outlet independent of the isolation of the first reaction chamber by the first set of microfluidic valves,
wherein the isolation effected by the first and the second set of microfluidic valves prevents movement of fluid into and out of the first and the second reaction chambers, wherein the first set of microfluidic valves comprises a first microfluidic valve spatially separated from the first inlet port and a second microfluidic valve spatially separated from the first outlet, and wherein the second set of microfluidic valves comprises a first microfluidic valve spatially separated from the second inlet port and a second microfluidic valve spatially separated from the second outlet, and wherein each of the first and second reaction chambers, the first and second inlet ports, the first and second outlets, and the first and second sets of microfluidic valves are all formed in the microfluidic substrate layer.

2. The microfluidic cartridge of claim 1, wherein the first reaction chamber and the second reaction chamber are configured to amplify one or more polynucleotides independently of the other chamber.

3. The microfluidic cartridge of claim 1, wherein the first outlet comprises a first vent and the second outlet comprises a second vent.

4. The microfluidic cartridge of claim 1, wherein the first inlet port and the second inlet port are configured to accept a sample from a pipette tip.

5. The microfluidic cartridge of claim 1, configured to carry out real-time PCR in at least one of the reaction chambers.

6. The microfluidic cartridge of claim 1, wherein the first inlet port and the second inlet port are spaced apart from one another to permit simultaneous loading from a multiple-pipette head dispenser.

7. The microfluidic cartridge of claim 1, wherein the first set of microfluidic valves and the second set of microfluidic valves comprise a temperature responsive substance that melts upon heating and seals the first and the second reaction chambers.

8. The microfluidic substrate of claim 1, wherein the first and second reaction chambers and the first and second sets of microfluidic valves are formed in a first side of the microfluidic substrate layer, and wherein the first and second inlet ports and the first and second outlets are formed in a second side of the microfluidic substrate layer opposite the first side.

9. A method of carrying out PCR independently on a plurality of polynucleotide-containing samples, the method comprising:
introducing the plurality of samples into the microfluidic cartridge of claim 1, wherein the cartridge has a plurality of reaction chambers comprising the first reaction chamber and the second reaction chamber, the plurality of reaction chambers configured to permit thermal cycling of the plurality of samples independently of one another;
moving the plurality of samples into the respective plurality of reaction chambers;
isolating the plurality of reaction chambers; and
amplifying polynucleotides contained with the plurality of samples, by application of successive heating and cooling cycles to the reaction chambers.

10. A microfluidic substrate, comprising:
a plurality of sample lanes, wherein each of the plurality of sample lanes comprises a microfluidic network having, in fluid communication with one another:
an inlet;
a first valve and a second valve;
a first channel leading from the inlet, via the first valve, to a reaction chamber; and
a second channel leading from the reaction chamber, via the second valve, to a vent,
wherein the first valve and the second valve are configured to isolate the reaction chamber from the inlet and the vent to prevent movement of fluid into or out of the reaction chamber, wherein the first valve is spatially separated from the inlet and the second valve is spatially separated from the vent, wherein the reaction chamber, the first channel, and the second channel are formed in a first side of the microfluidic substrate, wherein the inlet and the vent are formed in a second side of the microfluidic substrate opposite the first side, and wherein the first valve in each of the plurality of sample lanes is operated independently of any other first valve.

11. The microfluidic substrate of claim 10, additionally comprising:
a third channel leading from the inlet to the reaction chamber, wherein a gate is positioned in the third channel, and wherein the gate is configured to open the third channel to permit material from the reaction chamber to be removed via the inlet.

12. The microfluidic substrate of claim 10, wherein each of the plurality of sample lanes is configured to amplify one or more polynucleotides independently of the other lanes.

13. The microfluidic substrate of claim 10, wherein each of the plurality of sample lanes further compiises a bubble vent.

14. The microfluidic substrate of claim 10, wherein the inlet is configured to accept sample from a pipette tip.

15. The microfluidic substrate of claim 10, configured to carry out real-time PCR in at least one of the reaction chambers.

16. The microfluidic substrate of claim 10, wherein the inlets of the respective plurality of sample lanes are spaced apart from one another to permit simultaneous loading from a multiple-pipette head dispenser.

17. The microfluidic substrate of claim 10, wherein the first and second valves comprise a temperature responsive substance that melts upon heating and seals the reaction chamber.

18. The microfluidic substrate of claim 10, wherein the second valve in each of the plurality of sample lanes is operated independently of any other second valve.

19. A microfluidic cartridge comprising the microfluidic substrate of claim 10.

20. The microfluidic cartridge of claim 19, further comprising a registration member that ensures that the cartridge is received by a complementary diagnostic apparatus in a single orientation.

21. The microfluidic cartridge of claim 19, wherein each of the microfluidic networks, including the reaction chamber, the inlet, and the valves for isolating the reaction chamber, is defined in a single substrate.

22. The microfluidic cartridge of claim 21, wherein the substrate is a rigid substrate and impervious to air or liquid, and entry or exit of air or liquid during operation of the cartridge is only possible through the inlet or a vent.

* * * * *